(12) United States Patent
Otvos et al.

(10) Patent No.: US 9,361,429 B2
(45) Date of Patent: Jun. 7, 2016

(54) MULTI-PARAMETER DIABETES RISK EVALUATIONS

(71) Applicant: LipoScience, Inc., Raleigh, NC (US)

(72) Inventors: James D. Otvos, Cary, NC (US); Irina Y. Shalaurova, Cary, NC (US); Dennis W. Bennett, Shorewood, WI (US); Justyna E. Wolak-Dinsmore, Durham, NC (US); Thomas M. O'Connell, Chapel Hill, NC (US); Kelly Mercier, Durham, NC (US)

(73) Assignee: LIPOSCIENCE, INC., Raleigh, NC (US)

( * ) Notice: Subject to any disclaimer, the term of this patent is extended or adjusted under 35 U.S.C. 154(b) by 0 days.

(21) Appl. No.: 13/830,784

(22) Filed: Mar. 14, 2013

(65) Prior Publication Data

US 2013/0332082 A1  Dec. 12, 2013

Related U.S. Application Data

(60) Provisional application No. 61/657,315, filed on Jun. 8, 2012, provisional application No. 61/711,471, filed on Oct. 9, 2012, provisional application No. 61/739,305, filed on Dec. 19, 2012.

(51) Int. Cl.

| | |
|---|---|
| *G01N 33/48* | (2006.01) |
| *G01N 33/50* | (2006.01) |
| *G06F 19/00* | (2011.01) |
| *G01R 33/46* | (2006.01) |
| *G06F 17/10* | (2006.01) |
| *G01N 24/08* | (2006.01) |
| *G01R 33/465* | (2006.01) |
| *A61B 5/00* | (2006.01) |
| *A61B 5/055* | (2006.01) |

(52) U.S. Cl.
CPC .......... *G06F 19/3431* (2013.01); *A61B 5/4842* (2013.01); *A61B 5/7275* (2013.01); *G01N 24/08* (2013.01); *G01R 33/46* (2013.01); *G01R 33/465* (2013.01); *G06F 17/10* (2013.01); *G06F 19/34* (2013.01); *G06F 19/3437* (2013.01); *A61B 5/055* (2013.01)

(58) Field of Classification Search
None
See application file for complete search history.

(56) References Cited

U.S. PATENT DOCUMENTS

| | | | |
|---|---|---|---|
| 6,518,069 B1 | 2/2003 | Otvos et al. | |
| 6,576,471 B2 | 6/2003 | Otvos | |
| 7,181,348 B2 | 2/2007 | Wishart et al. | |
| 7,191,069 B2 | 3/2007 | Wishart et al. | |
| 7,373,256 B2 | 5/2008 | Nicholson et al. | |
| 7,491,543 B2 | 2/2009 | Barzilai | |
| 7,550,260 B2 | 6/2009 | Kaddurah-Daouk et al. | |
| 7,629,315 B2 * | 12/2009 | Zhao ............................. | 514/1.1 |
| 7,723,050 B2 | 5/2010 | Urdea et al. | |
| 7,923,253 B2 | 4/2011 | Metz et al. | |
| 7,927,878 B2 | 4/2011 | Kremer et al. | |
| 8,119,358 B2 | 2/2012 | Urdea et al. | |
| 8,187,830 B2 | 5/2012 | Hu et al. | |
| 8,367,359 B1 | 2/2013 | Adams et al. | |
| 8,386,187 B2 | 2/2013 | Otvos | |
| 8,409,816 B2 | 4/2013 | Urdea et al. | |
| 8,420,337 B2 | 4/2013 | Heinecke et al. | |
| 8,476,008 B2 | 7/2013 | Nagalla et al. | |
| 2005/0222504 A1 | 10/2005 | Otvos et al. | |
| 2008/0026378 A1 | 1/2008 | Bottazzo et al. | |
| 2008/0300170 A1 | 12/2008 | Gelber et al. | |
| 2009/0061475 A1 | 3/2009 | Berggren | |
| 2009/0286324 A1 | 11/2009 | Metz et al. | |
| 2010/0100334 A1 | 4/2010 | Otvos | |
| 2011/0004453 A1 | 1/2011 | Engelsen et al. | |
| 2011/0311650 A1 | 12/2011 | Wang et al. | |
| 2012/0122981 A1 | 5/2012 | Hu | |
| 2012/0309030 A1 | 12/2012 | McKenna et al. | |
| 2012/0328594 A1 | 12/2012 | McKenna et al. | |
| 2013/0177544 A1 | 7/2013 | Stoll et al. | |
| 2015/0127267 A1 | 5/2015 | Otvos et al. | |
| 2015/0149095 A1 | 5/2015 | Otvos et al. | |

FOREIGN PATENT DOCUMENTS

| | | |
|---|---|---|
| CN | 104520699 | 4/2015 |
| WO | WO 2011/153271 A1 | 12/2011 |
| WO | WO 2012/045773 A1 | 4/2012 |
| WO | WO 2013185014 | 12/2013 |

OTHER PUBLICATIONS

International Search Report and Written Opinion for corresponding PCT Application No. PCT/US2013/044679, Date of mailing Oct. 28, 2013.
Bell et al., Assignment of resonances for 'acute-phase' glycoproteins in high resolution proton NMR spectra of human blood plasma, Feb. 1987, 215(2): 311-315.
Nicholson et al., Proton-nuclear-magnetic-resonance studies of serum, plasma and urine from fasting normal and diabetic subjects, *Biochemical Journal* 1984, 217: 365-375.
Lanza et al., Quantitative Metabolomics by $^1$H-NMR and LC-MS/MS Confirms Altered Metabolic Pathways in Diabetes, *PloS one* 2010, 5(5), e10538: 1-10.
Vitols et al., Correcting Lineshapes in NMR Spectra, Chenomx 2006.
Wang et al., Metabolic profiles and the risk of developing diabetes, *Nature* 2011, 17(4): 448-453.
Barclay et al., "Glycemic index, glycemic load, and chronic disease risk—a meta-analysis of observational studies", The American Journal of Clinical Nutrition, 87(3), 2008, pp. 627-637.
Lu et al., "Evaluation of risk equations for prediction of short-term coronary heart disease events in patients with long-standing type 2 diabetes: the Translating Research into Action for Diabetes (TRIAD) study", BMC Endocrine disorders, 12 (Article No. 12), 2012, pp. 1-10.
O'Connell, "The complex role of branched chain amino acids in diabetes and cancer", Metabolites, 3(4), 2013, pp. 931-945.
Patent Cooperation Treaty, International Preliminary Report on Patentability, International Application No. PCT/US2013/44679, dated Dec. 18, 2014, 13 pages.
Patent Cooperation Treaty, International Search Report and Written Opinion, International Application No. PCT/US2015/10184, dated Mar. 31, 2015, 12 pages.

* cited by examiner

*Primary Examiner* — Russell S Negin
(74) *Attorney, Agent, or Firm* — Kilpatrick Townsend & Stockton LLP

(57) ABSTRACT

Methods, systems and circuits evaluate a subject's risk of developing type 2 diabetes or developing or having prediabetes using at least one defined mathematical model of risk of progression that can stratify risk for patients having the same glucose measurement. The model may include NMR derived measurements of GlycA and a plurality of selected lipoprotein components of at least one biosample of the subject.

52 Claims, 26 Drawing Sheets

| COMPONENT ID | COMPONENT CLASS | CHEMICAL SHIFT (PPM) | COMPONENT ID | COMPONENT CLASS | CHEMICAL SHIFT (PPM) | COMPONENT ID | COMPONENT CLASS | CHEMICAL SHIFT (PPM) |
|---|---|---|---|---|---|---|---|---|
| AA1 | METABOLITE A | 1.875040 | VLDL7 | VLDL | 1.966840 | GLYC21 | | 2.019880 |
| AA2 | METABOLITE A | 1.876400 | VLDL8 | VLDL | 1.968200 | GLYC22 | | 2.021240 |
| AA3 | METABOLITE A | 1.876400 | VLDL9 | VLDL | 1.969560 | GLYC23 | | 2.022600 |
| AA4 | METABOLITE A | 1.876400 | VLDL10 | VLDL | 1.970920 | GLYC24 | | 2.023960 |
| AA5 | METABOLITE A | 1.877760 | VLDL11 | VLDL | 1.971600 | GLYC25 | | 2.025320 |
| AA6 | METABOLITE A | 1.879120 | VLDL12 | VLDL | 1.973640 | GLYC26 | | 2.026680 |
| AA7 | METABOLITE A | 1.880480 | VLDL13 | VLDL | 1.975000 | GLYC27 | | 2.028040 |
| HDL1 | HDL | 1.915840 | VLDL14 | VLDL | 1.976360 | GLYC28 | | 2.029400 |
| HDL2 | HDL | 1.918560 | VLDL15 | VLDL | 1.975680 | GLYC29 | | 2.030760 |
| HDL3 | HDL | 1.919240 | VLDL16 | VLDL | 1.977040 | GLYC30 | | 2.032120 |
| HDL4 | HDL | 1.919920 | CHY1 | CHYLOS | 1.978400 | GLYC31 | | 2.034840 |
| HDL5 | HDL | 1.920600 | CHY2 | CHYLOS | 1.979080 | GLYC32 | | 2.037560 |
| HDL6 | HDL | 1.921280 | CHY3 | CHYLOS | 1.979760 | GLYC33 | | 2.040280 |
| HDL7 | HDL | 1.925360 | CHY4 | CHYLOS | 1.980440 | GLYC34 | | 2.043000 |
| HDL8 | HDL | 1.928760 | CHY5 | CHYLOS | 1.981120 | GLYC35 | | 2.045720 |
| HDL9 | HDL | 1.930800 | CHY6 | CHYLOS | 1.981800 | GLYC36 | | 2.048440 |
| HDL10 | HDL | 1.933520 | CHY7 | CHYLOS | 1.982480 | GLYC37 | | 2.051160 |
| HDL11 | HDL | 1.934880 | CHY8 | CHYLOS | 1.983160 | GLYC38 | | 2.053880 |
| HDL12 | HDL | 1.936240 | CHY9 | CHYLOS | 1.983840 | GLYC39 | | 2.056600 |
| HDL13 | HDL | 1.936920 | CHY10 | CHYLOS | 1.984520 | GLYC40 | | 2.059320 |
| HDL14 | HDL | 1.937600 | CHY11 | CHYLOS | 1.985200 | GLYC41 | | 2.062040 |
| HDL15 | HDL | 1.938280 | CHY12 | CHYLOS | 1.985880 | GLYC42 | | 2.064760 |
| HDL16 | HDL | 1.938960 | GLYC1 | | 1.992680 | GLYC43 | | 2.067480 |
| HDL17 | HDL | 1.939640 | GLYC2 | | 1.994040 | GLYC44 | | 2.070200 |
| HDL18 | HDL | 1.941000 | GLYC3 | | 1.995400 | GLYC45 | | 2.072920 |
| HDL19 | HDL | 1.941680 | GLYC4 | | 1.996760 | GLYC46 | | 2.075640 |
| HDL20 | HDL | 1.943040 | GLYC5 | | 1.998120 | PROTEIN | | |
| LDL1 | LDL | 1.947800 | GLYC6 | | 1.999480 | | | |
| LDL2 | LDL | 1.948480 | GLYC7 | | 2.000840 | | | |
| LDL3 | LDL | 1.949160 | GLYC8 | | 2.002200 | | | |
| LDL4 | LDL | 1.949840 | GLYC9 | | 2.003560 | | | |
| LDL5 | LDL | 1.950520 | GLYC10 | | 2.004920 | | | |
| LDL6 | LDL | 1.951200 | GLYC11 | | 2.006280 | | | |
| LDL7 | LDL | 1.952560 | GLYC12 | | 2.007640 | | | |
| LDL8 | LDL | 1.953920 | GLYC13 | | 2.009000 | | | |
| LDL9 | LDL | 1.955280 | GLYC14 | | 2.010360 | | | |
| VLDL1 | VLDL | 1.960040 | GLYC15 | | 2.011720 | | | |
| VLDL2 | VLDL | 1.961400 | GLYC16 | | 2.013080 | | | |
| VLDL3 | VLDL | 1.962760 | GLYC17 | | 2.014440 | | | |
| VLDL4 | VLDL | 1.964120 | GLYC18 | | 2.015800 | | | |
| VLDL5 | VLDL | 1.965480 | GLYC19 | | 2.017160 | | | |
| VLDL6 | VLDL | 1.966160 | GLYC20 | | 2.018520 | | | |

FIG. 7D

SPECTRAL OVERLAP FROM LIPOPROTEINS (ESPECIALLY VLDL/CHYLOS) COMPLICATES ANALYSIS OF SAMPLES WITH HIGH TRIGLYCERIDES (TG)

USE OF DIFFERENT PROTEIN COMPONENTS IN THE GlycA DECONVOLUTION MODEL GIVES
DIFFERENT GlycA CONCENTRATIONS AND DIFFERENT GlycA ASSOCIATIONS WITH CHD
EVENTS AND ALL-CAUSE DEATH IN MESA

| PROTEIN COMPONENT USED IN FITTING MODEL | GlycA CONCENTRATION | CHD EVENT PREDICTION | | ALL-CAUSE DEATH PREDICTION | |
|---|---|---|---|---|---|
| | µmol/L | $\chi^2$ | p | $\chi^2$ | p |
| PROTEIN #1 | 342 | 13.1 | 0.0003 | 23.1 | <0.0001 |
| PROTEIN #2 | 186 | 12.7 | 0.0004 | 11.2 | 0.0008 |
| PROTEIN #3 | 162 | 10.9 | 0.0003 | 7.4 | 0.007 |

FIG. 9A

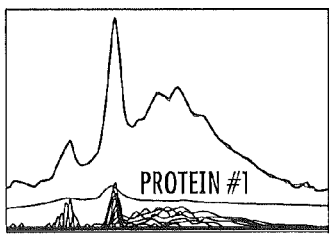

FIG. 9B

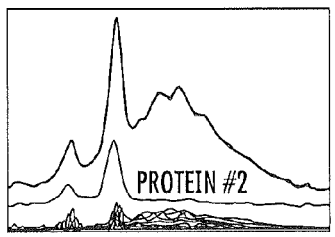

FIG. 9C

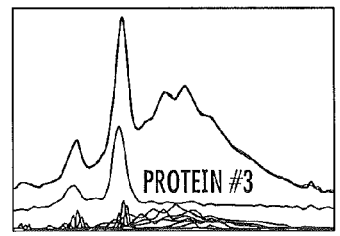

FIG. 9D

GlycA CONVERSION FACTOR GIVES
CONCENTRATION OF GLYCOPROTEIN N-ACETYL METHYL GROUPS 1 GlycA/B UNIT = 17.8 µmol/L

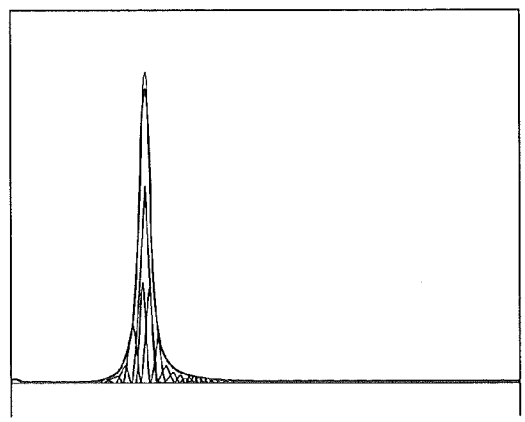

FIG. 10

PROSPECTIVE ASSOCIATIONS OF NMR-MEASURED GlycA AND VALINE LEVELS AND HS-CRP WITH SELECTED DISEASE OUTCOMES IN MESA (n~5680)

|  | GlycA | | hs-CRP | | VALINE | | GlycA+VALINE |
| --- | --- | --- | --- | --- | --- | --- | --- |
|  | $\chi^2$ | p | $\chi^2$ | p | $\chi^2$ | p | $\chi^2$ |
| CHD EVENTS (N=289) | 7.0 | 0.007 | 3.1 | ns | 0.3 | ns | 7.8 |
| ALL-CAUSE DEATH (N=346) | 24.8 | <0.0001 | 13.9 | 0.0003 | 14.4 | 0.0002 | 36.7 |
| CONGESTIVE HEART FAILURE (N=149) | 2.5 | ns | 2.9 | ns | 12.3 | 0.0006 | 14.1 |
| STROKE (N=117) | 1.3 | ns | 0 | ns | 0 | ns | 1.4 |
| CHRONIC KIDNEY DISEASE (N=181) | 29.3 | <0.0001 | 3.4 | 0.05 | 2.9 | ns | 31.0 |
| COPD (N=120) | 20.5 | <0.0001 | 3.6 | 0.03 | 6.7 | 0.01 | 26.3 |
| CANCER (N=440) | 8.0 | 0.004 | 3.0 | ns | 3.8 | 0.05 | 11.3 |
| ASTHMA (N=154) | 3.5 | 0.06 | 1.6 | ns | 2.0 | ns | 6.2 |
| DEMENTIA (N=71) | 5.8 | 0.01 | 0 | ns | 3.9 | 0.05 | 10.0 |
| DIABETES (N=493) | 10.3 | 0.001 | 4.7 | 0.04 | 29.0 | <0.0001 | 40.3 |

FIG. 13

CHARACTERISTICS OF MESA SUBJECTS BY GlycA QUARTILE

|  | GlycA QUARTILE | | | |
| --- | --- | --- | --- | --- |
|  | 1 | 2 | 3 | 4 |
| GlycA | 21.6 | 25.8 | 29.3 | 35.3 |
| hsCRP (mg/L) | 1.3 | 2.2 | 3.8 | 7.6 |
| SMOKING (%) | 9 | 11 | 13 | 17 |
| HYPERTENSION (%) | 34 | 41 | 47 | 55 |
| DIABETES (%) | 8.1 | 10.8 | 12.8 | 18.8 |
| MetSyn (%) | 20 | 31 | 39 | 55 |
| LP-IR SCORE | 35 | 44 | 46 | 52 |

FIG. 14

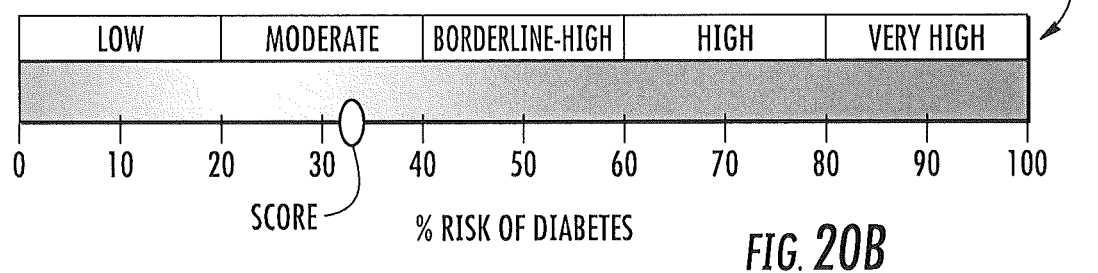
FIG. 20A
FIG. 20B
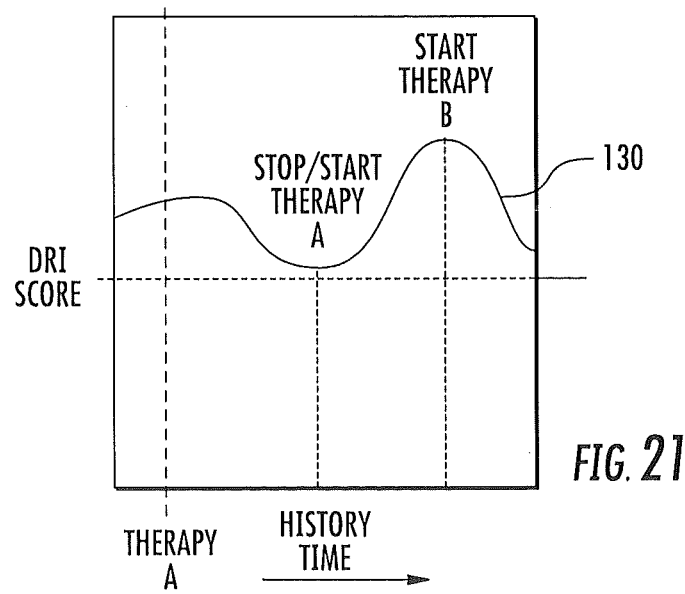
FIG. 21

OPTION #2

FPG: 108 mg/dL
DRI SCORE: 32% RISK OF DEVELOPING T2D OVER NEXT 5 YEARS

OPTION #2

FPG: 108 mg/dL
DRI SCORE: 32% RISK OF DEVELOPING T2D OVER NEXT 5 YEARS

| DRIp | IRAS | | | GLUCOSE SUBGROUP-SPECIFIC QUINTILES | | | | | | | | |
|---|---|---|---|---|---|---|---|---|---|---|---|---|
| GLUCOSE=<90 mg/dL | | | | GLUCOSE=90-110 mg/dL | | | | GLUCOSE>110 mg/dL | | | | |
| QUINTILES | N | NEW DIABETES | % | Q5/Q1 | QUINTILES | N | NEW DIABETES | % | Q5/Q1 | QUINTILES | N | NEW DIABETES | % | Q5/Q1 |
| 1 | 47 | 0 | 1.0 | | 1 | 122 | 7 | 5.7 | | 1 | 27 | 4 | 14.8 | |
| 2 | 50 | 2 | 4.0 | | 2 | 118 | 11 | 9.3 | | 2 | 25 | 8 | 32.0 | |
| 3 | 49 | 1 | 2.0 | | 3 | 122 | 15 | 12.3 | | 3 | 28 | 9 | 32.1 | |
| 4 | 50 | 3 | 6.0 | | 4 | 122 | 17 | 13.9 | | 4 | 25 | 10 | 40.0 | |
| 5 | 49 | 3 | 6.1 | 6.1 | 5 | 121 | 29 | 24.0 | 4.2 | 5 | 27 | 15 | 55.6 | 3.8 |
| Σ | 245 | 9 | 3.7 | | Σ | 605 | 79 | 13.1 | | Σ | 132 | 46 | 34.8 | |

| DRIp | MESA | | | GLUCOSE SUBGROUP-SPECIFIC QUINTILES | | | | | | | | |
|---|---|---|---|---|---|---|---|---|---|---|---|---|
| GLUCOSE<90 mg/dL (1) | | | | GLUCOSE 90-110 mg/dL (2) | | | | GLUCOSE >110 mg/dL | | | | |
| QUINTILES | N | NEW DIABETES | % | Q5/Q1 | QUINTILES | N | NEW DIABETES | % | Q5/Q1 | QUINTILES | N | NEW DIABETES | % | Q5/Q1 |
| 1 | 522 | 6 | 1.1 | | 1 | 424 | 11 | 2.6 | | 1 | 46 | 25 | 54.3 | |
| 2 | 553 | 4 | 0.7 | | 2 | 395 | 22 | 5.6 | | 2 | 46 | 21 | 45.7 | |
| 3 | 548 | 8 | 1.5 | | 3 | 407 | 41 | 10.1 | | 3 | 47 | 28 | 59.6 | |
| 4 | 549 | 20 | 3.6 | | 4 | 403 | 44 | 10.9 | | 4 | 46 | 32 | 69.6 | |
| 5 | 543 | 22 | 4.1 | 3.5 | 5 | 409 | 92 | 22.5 | 8.7 | 5 | 47 | 35 | 74.5 | 1.4 |
| Σ | 2715 | 60 | 2.2 | | Σ | 2038 | 210 | 10.3 | | Σ | 232 | 141 | 60.8 | |

| DRIp | MESA | | | GLUCOSE SUBGROUP-SPECIFIC QUINTILES FROM MESA | | | | | | | | |
|---|---|---|---|---|---|---|---|---|---|---|---|---|
| GLUCOSE=<90 mg/dL | | | | GLUCOSE=90-110 mg/dL | | | | GLUCOSE>110 mg/dL | | | | |
| QUINTILES | N | NEW DIABETES | % | Q5/Q1 | QUINTILES | N | NEW DIABETES | % | Q5/Q1 | QUINTILES | N | NEW DIABETES | % | Q5/Q1 |
| 1 | 23 | 0 | 1.0 | | 1 | 77 | 5 | 6.5 | | 1 | 28 | 4 | 14.3 | |
| 2 | 24 | 0 | 0.0 | | 2 | 74 | 4 | 5.4 | | 2 | 21 | 8 | 38.1 | |
| 3 | 44 | 2 | 4.5 | | 3 | 105 | 11 | 10.5 | | 3 | 25 | 9 | 36.0 | |
| 4 | 55 | 1 | 1.8 | | 4 | 118 | 13 | 11.0 | | 4 | 27 | 10 | 37.0 | |
| 5 | 99 | 6 | 6.1 | 6.1 | 5 | 231 | 46 | 19.9 | 3.1 | 5 | 31 | 15 | 48.4 | 3.4 |
| Σ | 245 | 9 | 3.7 | | Σ | 605 | 79 | 13.1 | | Σ | 132 | 46 | 34.8 | |

FIG. 27

| DRI-NMR IRAS | | | | | GLUCOSE SUBGROUP-SPECIFIC QUINTILES | | | | | | | | | |
|---|---|---|---|---|---|---|---|---|---|---|---|---|---|---|
| GLUCOSE=<90 mg/dL | | | | | GLUCOSE=90-110 mg/dL | | | | | GLUCOSE> 110 mg/dL | | | | |
| QUINTILES | N | NEW DIABETES | % | Q5/Q1 | QUINTILES | N | NEW DIABETES | % | Q5/Q1 | QUINTILES | N | NEW DIABETES | % | Q5/Q1 |
| 1 | 59 | 1 | 1.7 | | 1 | 120 | 10 | 8.3 | | 1 | 26 | 6 | 23.1 | |
| 2 | 51 | 1 | 2.0 | | 2 | 122 | 13 | 10.7 | | 2 | 27 | 7 | 25.9 | |
| 3 | 52 | 3 | 5.8 | | 3 | 120 | 14 | 11.7 | | 3 | 27 | 8 | 29.6 | |
| 4 | 46 | 1 | 2.2 | | 4 | 122 | 23 | 18.9 | | 4 | 26 | 11 | 42.3 | |
| 5 | 37 | 3 | 8.1 | 4.8 | 5 | 121 | 19 | 15.7 | 1.9 | 5 | 26 | 14 | 53.8 | 2.3 |
| Σ | 245 | 9 | 3.7 | | Σ | 605 | 79 | 13.1 | | Σ | 132 | 46 | 34.8 | |

| DRI-NMR MESA | | | | | GLUCOSE SUBGROUP-SPECIFIC QUINTILES | | | | | | | | | |
|---|---|---|---|---|---|---|---|---|---|---|---|---|---|---|
| GLUCOSE <90 mg/dL (1) | | | | | GLUCOSE 90-110 mg/dL | | | | | GLUCOSE>110 mg/dL | | | | |
| QUINTILES | N | NEW DIABETES | % | Q5/Q1 | QUINTILES | N | NEW DIABETES | % | Q5/Q1 | QUINTILES | N | NEW DIABETES | % | Q5/Q1 |
| 1 | 546 | 6 | 1.1 | | 1 | 405 | 13 | 3.2 | | 1 | 46 | 26 | 56.5 | |
| 2 | 538 | 5 | 0.9 | | 2 | 408 | 39 | 9.6 | | 2 | 47 | 26 | 55.3 | |
| 3 | 546 | 11 | 2.0 | | 3 | 411 | 37 | 9.0 | | 3 | 47 | 29 | 61.7 | |
| 4 | 542 | 17 | 3.1 | | 4 | 405 | 58 | 14.3 | | 4 | 45 | 30 | 66.7 | |
| 5 | 543 | 21 | 3.9 | 3.5 | 5 | 409 | 63 | 15.4 | 4.8 | 5 | 47 | 30 | 63.8 | 1.1 |
| Σ | 2715 | 60 | 2.2 | | Σ | 2038 | 210 | 10.3 | | Σ | 232 | 141 | 60.8 | |

| DRI-NMR IRAS | | | | | GLUCOSE SUBGROUP-SPECIFIC QUINTILES FROM MESA | | | | | | | | | |
|---|---|---|---|---|---|---|---|---|---|---|---|---|---|---|
| GLUCOSE=<90 mg/dL (1) | | | | | GLUCOSE=90-110 mg/dL (2) | | | | | GLUCOSE>110 mg/dL | | | | |
| QUINTILES | N | NEW DIABETES | % | Q5/Q1 | QUINTILES | N | NEW DIABETES | % | Q5/Q1 | QUINTILES | N | NEW DIABETES | % | Q5/Q1 |
| 1 | 39 | 0 | 1.0 | | 1 | 96 | 7 | 7.3 | | 1 | 25 | 5 | 20.0 | |
| 2 | 28 | 1 | 3.6 | | 2 | 96 | 8 | 8.3 | | 2 | 27 | 8 | 29.6 | |
| 3 | 41 | 1 | 2.4 | | 3 | 90 | 14 | 15.6 | | 3 | 16 | 2 | 12.5 | |
| 4 | 61 | 4 | 6.6 | | 4 | 140 | 19 | 13.6 | | 4 | 23 | 10 | 43.5 | |
| 5 | 79 | 3 | 3.9 | 3.9 | 5 | 183 | 31 | 16.9 | 2.3 | 5 | 41 | 21 | 51.2 | 2.6 |
| Σ | 245 | 9 | 3.7 | | Σ | 605 | 79 | 13.1 | | Σ | 132 | 46 | 34.8 | |

FIG. 28

MULTI-PARAMETER DIABETES RISK EVALUATIONS

RELATED APPLICATIONS

This application claims the benefit of and priority to U.S. Provisional Application Ser. No. 61/657,315, filed Jun. 8, 2012, U.S. Provisional Application Ser. No. 61/711,471, filed Oct. 9, 2012 and U.S. Provisional Application Ser. No. 61/739,305, filed Dec. 19, 2012, the contents of which are hereby incorporated by reference as if recited in full herein.

FIELD OF THE INVENTION

The present invention relates generally to analysis of in vitro biosamples. The invention may be particularly suitable for NMR analysis of in vitro biosamples.

BACKGROUND OF THE INVENTION

Type 2 diabetes mellitus (T2DM or "diabetes") is one of the most costly and burdensome chronic diseases in the U.S. and other countries. The defining feature of T2DM is hyperglycemia, a reflection of impaired carbohydrate (glucose) utilization resulting from a defective or deficient insulin secretory response. T2DM is a late manifestation of metabolic derangements that begin many years earlier. Its cause is believed to be a progressive increase in insulin resistance coupled with deteriorating β-cell function. So long as the pancreatic β-cells are able to secrete enough insulin to compensate for the progressive resistance of target tissues to insulin's hypoglycemic effects, the patient is able to maintain normal fasting glucose levels. Hyperglycemia and the transition to T2DM occur as a consequence of progressive β-cell dysfunction which leads to failure to maintain hypersecretion of insulin in the face of increasing insulin resistance.

Type 2 diabetes has been traditionally diagnosed by the detection of elevated levels of glucose (sugar) in the blood (hyperglycemia). While hyperglycemia defines diabetes, it is a very late stage development in the chain of events that lead from insulin resistance to full-blown diabetes. Accordingly, it would be desirable to have a way of identifying whether or not a subject is at risk for developing Type 2 diabetes (i.e., is predisposed to the condition) prior to the development of the classic symptoms, such as hyperglycemia. Earlier detection of indicators of the disease (e.g., detection before glucose levels are elevated enough to be considered hyperglycemia) may lead to more effective treatment of the disease, if not actual prevention of the onset of the disease.

The most direct and accurate methods for assessing insulin resistance are laborious and time-consuming, and thus impractical for clinical application. The "gold standard" among these research methods is the hyperinsulinemic euglycemic clamp, which quantifies the maximal glucose disposal rate (GDR, inversely proportional to insulin resistance) during the clamp. Another arduous research method which is somewhat less reproducible (CV 14-30%) is the frequently sampled intravenous glucose tolerance test (IVGTT) with minimal model analysis, which measures insulin sensitivity ($S_i$), the inverse of insulin resistance.

Risk of progression to Type 2 diabetes is currently assessed primarily by fasting glucose, with concentrations 100-125 mg/dL defining a high-risk "pre-diabetes" condition and for which T2DM is currently defined in patients having fasting plasma glucose levels at 126 mg/dL and above. However, the actual risk of individual patients with pre-diabetes (those at risk of developing T2DM in the future) varies widely.

NMR spectroscopy has been used to concurrently measure low density lipoproteins (LDL), high density lipoproteins (HDL), and very low density lipoproteins (VLDL), as LDL, HDL and VLDL particle subclasses from in vitro blood plasma or serum samples. See, U.S. Pat. Nos. 4,933,844 and 6,617,167, the contents of which are hereby incorporated by reference as if recited in full herein. U.S. Pat. No. 6,518,069 to Otvos et al. describes NMR derived measurements of glucose and/or certain lipoprotein values to assess a patient's risk of developing T2DM.

Generally stated, to evaluate the lipoproteins in a blood plasma and/or serum sample, the amplitudes of a plurality of NMR spectroscopy derived signals within a chemical shift region of NMR spectra are derived by deconvolution of the composite methyl signal envelope to yield subclass concentrations. The subclasses are represented by many (typically over 60) discrete contributing subclass signals associated with NMR frequency and lipoprotein diameter. The NMR evaluations can interrogate the NMR signals to produce concentrations of different subpopulations, typically seventy-three discrete subpopulations, 27 for VLDL, 20 for LDL and 26 for HDL. These sub-populations can be further characterized as associated with a particular size range within the VLDL, LDL or HDL subclasses.

An advanced lipoprotein test panel, such as the LIPOPROFILE® lipoprotein test, available from LipoScience, Raleigh, N.C., has typically included a total high density lipoprotein particle (HDL-P) measurement (e.g., HDL-P number) that sums the concentration of all the HDL subclasses and a total low density lipoprotein particle (LDL-P) measurement that sums the concentration of all the LDL subclasses (e.g., LDL-P number). The LDL-P and HDL-P numbers represent the concentration of those respective particles in concentration units such as nmol/L. LipoScience has also developed a lipoprotein-based insulin resistance and sensitivity index (the "LP-IR™" index) as described in U.S. Pat. No. 8,386,187, the contents of which are hereby incorporated by reference as if recited in full herein.

Despite the foregoing, there remains a need for evaluations that can predict or assess a person's risk of developing type 2 diabetes before the onset of the disease.

SUMMARY

Embodiments of the invention provide risk assessments of a subject's risk of having prediabetes and/or developing type-2 diabetes in the future using a multi-parameter (multi-variate) model of defined predictive biomarkers.

The multi-variate risk progression model can include at least one defined lipoprotein component, at least one defined branched chain amino acid and at least one inflammatory biomarker.

The multi-variate model can be used for assessing patients for or during clinical trials, during a therapy or therapies, for drug development, and/or to identify or monitor anti-obesity drugs or other drug therapy candidates.

The multi-variate model can include at least one of the following: NMR measurements of GlycA, valine, and a plurality of lipoprotein components (e.g., subclasses) using the same NMR spectrums.

Embodiments of the invention include, methods, circuits, NMR spectrometers or NMR analyzers, and processors that evaluate a future risk of developing diabetes and/or risk stratification for those having "prediabetes" by evaluating NMR spectra of an in vitro blood plasma or serum patient sample using a defined multi-component risk progression model and NMR signal having a peak centered at about 2.00 ppm for GlycA.

The diabetes risk index can be calculated using a mathematical model of risk that generates a single score representing future risk of developing type 2 diabetes in a range from 0-100%.

The diabetes risk index can include lipoprotein components and at least one of GlycA and valine.

The lipoprotein components can include at least one of (i) a ratio of medium to total high density lipoprotein particle (HDL-P) number and (ii) VLDL size.

Yet other embodiments are directed to a patient report that includes a diabetes risk index (DRI) showing a percentage from 0-100 of risk of diabetes conversion rate over a 1, 2, 3, 4, 5, 6, or 7 year risk window based on a FPG level and an associated quartile or quintile of the patient's DRI risk score relative to a defined population. The patient report can include the patient's risk and a comparative risk of a population with a lower or higher quartile or quintile DRI score and the same FPG.

The DRI risk score can be calculated using a plurality of NMR derived measurements including: lipoprotein measurements, a measure of GlycA in µmol/L and/or arbitrary units, and optionally a measure of valine in µmol/L and/or arbitrary units.

Embodiments of the invention include a method of evaluating a subject's risk of developing type 2 diabetes and/or of having prediabetes. The methods include programmatically calculating a diabetes risk index score of a subject using at least one defined mathematical model of risk of developing type 2 diabetes that includes at least one lipoprotein component, at least one branched chain amino acid and at least one inflammatory biomarker obtained from at least one in vitro biosample of the subject.

In some embodiments, the at least one defined mathematical model of risk may include NMR derived measurements of a plurality of selected lipoprotein components of the at least one biosample of the subject, and NMR measurements of at least one of GlycA and valine. The defined mathematical risk model may include only NMR derived measurements of a subject's in vitro blood plasma or serum biosample.

In some embodiments, the method may include programmatically defining at least two different mathematical models of risk of developing type 2 diabetes, the at least two different mathematical models including one for subjects on a statin therapy that includes lipoprotein components that are statin insensitive and one for subjects not on a statin therapy with at least one different lipoprotein component.

In some embodiments, the method may include programmatically defining at least two different mathematical models of risk of developing type 2 diabetes. The at least two different mathematical models can have different lipoprotein components including one for fasting biosamples and one for non-fasting biosamples.

In some embodiments, the method may include programmatically generating a report with a graph of risk of progression to type 2 diabetes in the future over a 1-7 year period versus ranges of fasting glucose levels and a quartile of risk associated with the diabetes risk index score. In some embodiments, the graph shows references of at least first (low) and fourth (high) quartile DRI scores based on a defined population to thereby allow for ease of identifying or understanding risk stratification.

In some embodiments, the method can include programmatically evaluating a fasting blood glucose measurement of the subject using at least one in vitro biosample. The diabetes risk index score can be a numerical score within a defined score range, with scores associated with a fourth quartile (4Q) or fifth quintile (5Q) of a population norm reflecting an increased or high risk of developing type 2 diabetes within 5-7 years. The method can include programmatically identifying respective subjects that are at increased risk of developing type 2 diabetes prior to onset of type-2 diabetes when fasting blood glucose levels are between 90-110 mg/dL and the diabetes risk score is in the 4Q or 5Q range.

In some embodiments, the method may include evaluating a fasting blood glucose measurement of the subject, wherein the diabetes risk index score is a numerical score within a defined score range, with scores associated with a fourth quartile (4Q) or fifth quintile (5Q) of a population norm reflecting an increased or high risk of developing type 2 diabetes within 5-7 years.

The method can include programmatically identifying respective subjects that are at increased risk of developing type 2 diabetes prior to onset of type-2 diabetes when fasting blood glucose (FPG) levels are between 90-125 mg/dL. The programmatically identifying can be carried out to stratify risk in subjects having the same FPG and a different diabetes risk score.

In some embodiments, the method can include, before the programmatic calculation, placing a blood plasma or serum sample of the subject in an NMR spectrometer; obtaining at least one NMR spectrum of the sample; deconvolving the obtained at least one NMR spectrum; and calculating NMR derived measurements of GlycA and a plurality of selected lipoprotein parameters based on the deconvolved at least one NMR spectrum. The calculating step may be carried out to also calculate a measurement of branched chain amino acid valine.

In some embodiments, the diabetes risk index score may have a defined numerical range. The method can include programmatically generating a report that identifies a respective subject as at risk of developing prediabetes if a fasting blood plasma or serum glucose value is between about 90-99 mg/dl and the diabetes risk index is in a fourth quartile or fifth quintile of a population norm.

In some embodiments, the defined at least one mathematical model may include NMR measurements of GlycA and a plurality of selected lipoprotein components using lipoprotein subclasses, sizes and concentrations measured from an in vitro blood plasma or serum biosample.

In some embodiments, the at least one defined mathematical model may be selected lipoprotein components comprising at least two of the following: large VLDL subclass particle number, medium VLDL subclass particle number, total HDL subclass particle number, medium HDL subclass particle number and VLDL particle size.

The selected lipoprotein components may include all of the listed lipoprotein components.

In some embodiments, the at least one defined mathematical model may include a ratio of medium HDL-P to total HDL-P.

The at least one defined mathematical model may, in some embodiments, include VLDL subclass particle size (vsz3), a ratio of medium HDL-P to total HDL-P (HMP_HDLP) multiplied by GlycA and a ratio of VLDL size by a sum of large VLDL-P and medium VLDL-P.

Before the programmatic calculation, in some embodiments, the method may include electronically obtaining a composite NMR spectrum of a GlycA fitting region of the biosample of the subject, wherein the GlycA fitting region extends from 1.845 ppm to 2.080 ppm, and wherein the GlycA peak region is centered at 2.00 ppm; electronically deconvolving the composite NMR spectrum using a defined deconvolution model with high density lipoprotein (HDL) components, low density lipoprotein (LDL) components, VLDL (very low density lipoprotein)/chylomicron components, and curve fit functions associated with at least a GlycA peak region; and programmatically generating a measure of GlycA using the curve fit functions. The method may further include applying a conversion factor to the measure of GlycA to provide the measure in µmol/L.

In some embodiments, the curve fit functions may be overlapping curve fit functions. The measure of GlycA may be generated by summing a defined number of curve fit functions. The deconvolution model may further comprise a protein signal component for protein having a density greater than 1.21 g/L.

Before the programmatic calculation, in some embodiments, the method may include electronically obtaining NMR spectrums of a valine fitting region of the biosample of the subject; electronically identifying a valine signal as located upstream or downstream a defined number of data points of a peak of a defined diluent in the biosample; electronically deconvolving the composite NMR spectrum using a defined deconvolution model; and electronically quantifying valine using the deconvolved NMR spectrum.

In some embodiments, the at least one defined mathematical model may include a plurality of different defined models, including one that includes lipoprotein components that are insensitive to statin therapy, one that includes lipoprotein components that are sensitive to statin therapy, one that is for fasting biosamples and one that is for non-fasting biosamples.

Certain embodiments of the present invention are directed to a circuit configured to determine whether a patient is at-risk for developing type 2 diabetes within the next 5-7 years and/or whether a patient has prediabetes. The circuit includes at least one processor configured to electronically calculate a diabetes risk index based on at least one mathematical model of risk to convergence to type 2 diabetes within 5-7 years that considers at least one lipoprotein component, at least one branched chain amino acid and GlycA from at least one in vitro biosample of the subject.

The at least one mathematical model of risk, in some embodiments, may include NMR derived measurements of GlycA, valine and a plurality of lipoprotein components.

In some embodiments, the at least one processor may be configured to define at least two different mathematical models of risk of developing type 2 diabetes. The at least two different mathematical models can include a first model for subjects on a statin therapy that includes lipoprotein components that are statin insensitive and a second model for subjects not on a statin therapy. The second model can include at least some lipoprotein components that are different from the first model. The circuit can be configured to identify subject characteristics to select the appropriate first or second model of risk for the calculation of the diabetes risk index score.

In certain embodiments, the at least one processor may be configured to define at least two different mathematical models of risk of developing type 2 diabetes with different lipoprotein components, the at least two different mathematical models including one for fasting biosamples, and one for non-fasting biosamples. The circuit can identify subject characteristics to select the appropriate mathematical model of risk for calculation of the diabetes risk index score.

In some embodiments, the at least one processor may be configured to generate a report with a graph of risk of progression to type 2 diabetes in the future over a 1-7 year period versus ranges of fasting glucose levels and a quartile of risk associated with the diabetes risk index score. The graph may include visual references of at least first (low) and fourth (high) quartile DRI scores based on a defined population to thereby allow for ease of identifying or understanding risk stratification.

The at least one processor, in some embodiments, may be configured to evaluate a fasting blood glucose measurement of the subject, wherein the diabetes risk index score is a numerical score within a defined score range, with scores associated with a fourth quartile (4Q) or fifth quintile (5Q) of a population norm reflecting an increased or high risk of developing type 2 diabetes within 5-7 years. The at least one processor can be configured to identify respective subjects that are at increased risk of developing type 2 diabetes prior to onset of type-2 diabetes when fasting blood glucose levels are between 90-110 mg/dl and the diabetes risk score is in the 4Q or 5Q range.

In some embodiments, the at least one processor may be configured to evaluate a fasting blood glucose measurement of the subject. The diabetes risk index score can be a numerical score within a defined score range, with scores associated with a fourth quartile (4Q) or fifth quintile (5Q) of a population norm reflecting an increased or high risk of developing type 2 diabetes within 5-7 years. The at least one processor can be configured to identify respective subjects that are at increased risk of developing type 2 diabetes prior to onset of type-2 diabetes when fasting blood glucose (FPG) levels are between 90-125 mg/dL. The at least one processor is configured to generate a report that can stratify risk in subjects having the same FPG and a different diabetes risk score.

In some embodiments, the at least one mathematical model may include a plurality of lipoprotein components comprising at least two of the following: large VLDL subclass particle number, medium VLDL subclass particle number, total HDL subclass particle number, medium HDL subclass particle number and VLDL particle size. The mathematical model may include all of the listed lipoprotein components.

In some embodiments, one of the lipoprotein components of the mathematical model may be a ratio of medium HDL-P to total HDL-P.

In certain embodiments, the at least one mathematical model may include a plurality of lipoprotein components including VLDL subclass particle size (vsz3), a ratio of medium HDL-P to total HDL-P (HMP_HDLP) multiplied by GlycA and a ratio of VLDL size by a sum of large VLDL-P and medium VLDL-P.

Certain embodiments of the present invention are directed to a computer program product for evaluating in vitro patient biosamples. The computer program product includes a non-transitory computer readable storage medium having computer readable program code embodied in the medium. The computer-readable program code includes computer readable program code that provides at least one mathematical model of risk to progression to type 2 diabetes over a defined time period of between 1-7 years. The at least one mathematical model of risk to progression to type 2 diabetes can include a plurality of components, including at least one lipoprotein component, at least one inflammatory marker and at least one branched chain amino acid; and computer readable program code that calculates a diabetes risk index associated with a patient's biosample based on the at least one mathematical model of a risk of developing type 2 diabetes.

In some embodiments, the computer readable program code that provides the at least one mathematical model may include model components of NMR derived measurements of GlycA and valine.

In some embodiments, the computer program product may include computer readable program code configured to evaluate a glucose measurement of the patient. The computer readable program code that calculates a diabetes risk index can calculate the index as a numerical score within a defined score range, with scores associated with a fourth quartile (4Q) or fifth quintile (5Q) of a population norm reflecting an increased or high risk of developing type 2 diabetes within 5-7 years.

The computer program product may further include computer readable program code configured to identify respective patients that are at increased risk of developing type 2 diabetes prior to onset of type-2 diabetes when fasting blood glucose levels are between 90-110 mg/dL and the diabetes risk score is in the 4Q or 5Q range.

In some embodiments, the computer program product may be configured to generate a report that identifies respective subjects that are at increased risk of developing type 2 diabetes prior to onset of type-2 diabetes when fasting blood glucose (FPG) levels are between 90-125 mg/dL. The mathematical model can stratify risk in subjects having the same FPG and a different diabetes risk score.

In some embodiments, the at least one mathematical model may include a plurality of lipoprotein components comprising at least two of the following: large VLDL subclass particle number, medium VLDL subclass particle number, total HDL subclass particle number, medium HDL subclass particle number and VLDL particle size. The mathematical model may include all of the listed lipoprotein components.

In some embodiments, the mathematical model may include a ratio of medium HDL-P to total HDL-P. In some embodiments, the at least one mathematical model may include a plurality of lipoprotein components including VLDL subclass particle size (vsz3), a ratio of medium HDL-P to total HDL-P (HMP_HDLP) multiplied by GlycA and a ratio of VLDL size by a sum of large VLDL-P and medium VLDL-P.

The computer program product may further include computer readable program code that identifies and deconvolves a valine fitting region of a composite NMR spectrum blood serum or plasma sample of a subject and generates a calculated measurement of valine; and computer readable program code that deconvolves a GlycA fitting region of the composite NMR spectrum. The computer readable program code can deconvolve the composite NMR spectrum using a defined GlycA deconvolution model with (i) high density lipoprotein (HDL) components, (ii) low density lipoprotein (LDL) components, (iii) VLDL (very low density lipoprotein)/chylomicron components, (iv) another defined protein signal component and (v) curve fitting functions applied to at least a GlycA peak region and generates a calculated measurement of GlycA.

Still other embodiments are directed to a system. The system includes an NMR spectrometer for acquiring at least one NMR spectrum of an in vitro biosample and at least one processor in communication with the NMR spectrometer. The at least one processor is configured to determine for a respective biosample using the at least one NMR spectrum a diabetes risk index score based on at least one defined mathematical model of risk to convergence to type 2 diabetes within 5-7 years that considers at least one lipoprotein component, at least one branched chain amino acid and at least one inflammatory biomarker obtained from at least one in vitro biosample of the subject.

The at least one processor may be configured to deconvolve the at least one NMR spectrum and generate: (i) an NMR measurement of GlycA: (ii) an NMR measurement of valine; (iii) NMR measurements of lipoprotein parameters; and (iv) the diabetes risk index using the NMR measurements of GlycA, valine as components of the at least one defined mathematical model.

In some embodiments, the at least one processor may be configured to define at least two different mathematical models of risk of developing type 2 diabetes. The at least two different mathematical models can include one for subjects on a statin therapy that includes lipoprotein components that are statin insensitive and one for subjects not on a statin therapy with different lipoprotein components.

In some embodiments, the at least one processor in the system may be configured to define at least two different mathematical models of risk of developing type 2 diabetes with different lipoprotein components, the at least two different mathematical models including one for fasting biosamples, and one for non-fasting biosamples.

The at least one processor in the system, in some embodiments, may be configured to generate a report with a graph of risk of progression to type 2 diabetes in the future over a 1-7 year period versus ranges of fasting glucose levels and a quartile of risk associated with the diabetes risk index score. The graph may include visual references of at least first (low) and fourth (high) quartile DRI scores based on a defined population to thereby allow for ease of identifying or understanding risk stratification.

In some embodiments, the defined at least one mathematical model may include NMR measurements of GlycA and a plurality of selected lipoprotein components using lipoprotein subclasses, sizes and concentrations measured from an in vitro blood plasma or serum biosample.

In some embodiments, the at least one defined mathematical model may include selected lipoprotein components comprising at least two of the following: large VLDL subclass particle number, medium VLDL subclass particle number, total HDL subclass particle number, medium HDL subclass particle number and VLDL particle size. The selected lipoprotein components may include all of the listed lipoprotein components.

In some embodiments, the at least one defined mathematical model may include a ratio of medium HDL-P to total HDL-P.

In some embodiments, the at least one defined mathematical model may include VLDL subclass particle size (vsz3), a ratio of medium HDL-P to total HDL-P (HMP_HDLP) multiplied by GlycA and a ratio of VLDL size by a sum of large VLDL-P and medium VLDL-P.

Other embodiments of the present invention are directed to a patient report comprising: a diabetes risk index score calculated based on a defined mathematical model of risk of progression to type 2 diabetes within the next 5-7 years, with values above a population norm associated with increased risk, and comprising a graph showing a percentage in a range of risk of diabetes conversion over a 1, 2, 3, 4, 5, 6, or 7 year risk window versus glucose level and an associated quartile or quintile of the patient's DRI risk score relative to a defined population, and optionally a comparative risk of a population with a lower or higher quartile or quintile DRI score and the same glucose measurement.

Still other embodiments are directed to NMR systems. The systems include a NMR spectrometer; a flow probe in communication with the spectrometer; and at least one processor in communication with the spectrometer. The at least one processor is configured to: (a) obtain (i) NMR signal of a defined GlycA fitting region of NMR spectra associated with GlycA of a blood plasma or serum specimen in the flow probe; (ii) NMR signal of a defined valine fitting region of NMR spectra associated with the specimen in the flow probe;

and (iii) NMR signal of lipoprotein parameters; (b) calculate measurements of GlycA, valine and the lipoprotein parameters; and (c) calculate a diabetes risk index using a defined mathematical model of risk of developing type 2 diabetes and/or having prediabetes that uses the calculated measurements of GlycA, valine and at least a plurality of the lipoprotein parameters.

The at least one processor in the NMR system may include at least one local or remote processor the NMR analyzer, wherein the at least one processor is configured to (i) deconvolve at least one composite NMR spectrum of the specimen to generate a measurement of GlycA, valine and the lipoprotein parameters.

Additional aspects of the present invention are directed to methods of monitoring a patient to evaluate a therapy or determine whether the patient is at-risk of developing type 2 diabetes or has prediabetes. The methods include: programmatically providing at least one defined mathematical model of risk of progression to type 2 diabetes that includes a plurality of components including NMR derived measurements of selected lipoprotein subclasses and at least one of valine or GlycA; programmatically deconvolving at least one NMR spectrum of respective in vitro patient blood plasma or serum samples and determining measurements of lipoprotein subclasses, GlycA and valine; programmatically calculating a diabetes risk index score of the respective patients using the at least one defined model and corresponding patient sample measurements; and evaluating at least one of (i) whether the diabetes risk index is above a defined level of a population norm associated with increased risk of developing type 2 diabetes; or (ii) whether the diabetes risk index is increasing or decreasing over time in response to a therapy.

Further features, advantages and details of the present invention will be appreciated by those of ordinary skill in the art from a reading of the figures and the detailed description of the preferred embodiments that follow, such description being merely illustrative of the present invention. Features described with respect with one embodiment can be incorporated with other embodiments although not specifically discussed therewith. That is, it is noted that aspects of the invention described with respect to one embodiment, may be incorporated in a different embodiment although not specifically described relative thereto. That is, all embodiments and/or features of any embodiment can be combined in any way and/or combination. Applicant reserves the right to change any originally filed claim or file any new claim accordingly, including the right to be able to amend any originally filed claim to depend from and/or incorporate any feature of any other claim although not originally claimed in that manner. The foregoing and other aspects of the present invention are explained in detail in the specification set forth below.

As will be appreciated by those of skill in the art in light of the present disclosure, embodiments of the present invention may include methods, systems, apparatus and/or computer program products or combinations thereof.

BRIEF DESCRIPTION OF THE FIGURES

FIG. 7D is a table of different components in a GlycA/B deconvolution model according to embodiments of the present invention.

FIG. 9A is a table of different measures of GlycA concentration, depending on a protein component used in the deconvolution (e.g., "fitting") model.

FIGS. 9B-9D illustrate the GlycA and GlycB "fits" (deconvolution) of the same plasma sample using deconvolution models with different protein components (#1-#3 in the table in FIG. 9A) according to embodiments of the present invention.

FIG. 10 is a schematic screen shot of the deconvolution of a 10 mmol/L reference sample of N-acetylglucosamine, used to generate a conversion factor relating GlycA and GlycB signal areas to glycoprotein N-acetyl methyl group concentrations according to embodiments of the present invention.

FIG. 13 is a chart of prospective associations of hs-CRP and NMR-measured GlycA and NMR-measured valine levels with various disease outcomes in MESA (n=5680) according to embodiments of the present invention.

FIG. 14 is a chart of characteristics of MESA subjects by NMR measured GlycA quartile (in "NMR signal area units") according to embodiments of the present invention.

FIG. 20A is an example of a patient report that includes a GlycA measurement and/or a diabetes risk index according to embodiments of the present invention.

FIG. 20B is another example of a patient report with a visual (typically color-coded) graphic summary of a continuum of risk from low to high according to embodiments of the present invention.

FIG. 21 is a prophetic example of a graph of DRI versus time that can be used to monitor change to evaluate a patient's risk status, change in status, and/or clinical efficacy of a therapy or even used for clinical trials or to contradict planned therapies and the like according to embodiments of the present invention.

FIG. 22A shows patient #1's score while FIG. 22B shows patient #1's score in comparison with a lesser risk patient (patient number 2) having the same FPG. While each patient has the same FPG, they have different metabolic issues identified by the DRI scores stratifying risk according to embodiments of the present invention.

FIG. 23A is for a 4-year risk of conversion to diabetes. FIG. 23B is a 5-year risk of conversion and FIG. 23C is a 6 year risk of conversion.

FIG. 27 is a table of data that show the performance of DRI in the IRAS dataset, the MESA dataset, and IRAS dataset (using the glucose subgroups from MESA) according to embodiments of the present invention.

FIG. 28 shows the performance of DRI (w/o glucose) in the same dataset criteria as FIG. 27 according to embodiments of the present invention.

Figure 1:
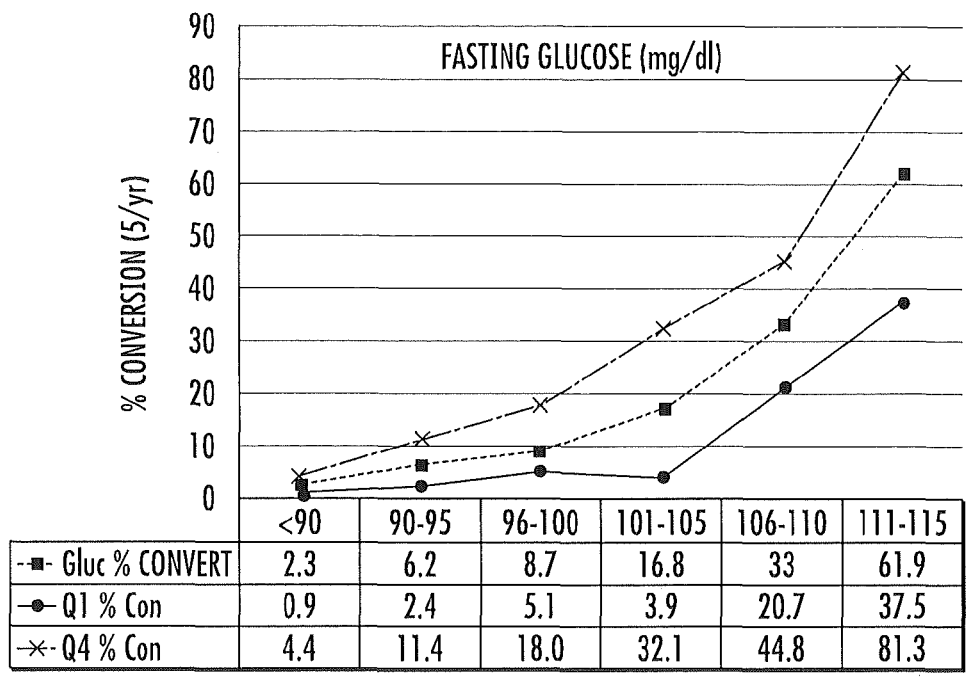
FIG. 1 is a graph showing a 5 year conversion risk of developing T2DM based on fasting glucose levels (mg/dl) and first and fourth quartiles (Q1, Q4, respectively) of a diabetes risk index according to embodiments of the present invention. The data in the table represent the percent of subjects in the 1$^{st}$ and 4$^{th}$ quartiles of six glucose subgroups that convert to type 2 diabetes over a 5 year period.

The foregoing and other objects and aspects of the present invention are explained in detail in the specification set forth below.

DETAILED DESCRIPTION OF EMBODIMENTS OF THE INVENTION

The present invention now is described more fully hereinafter with reference to the accompanying drawings, in which embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art.

Like numbers refer to like elements throughout. In the figures, the thickness of certain lines, layers, components, elements or features may be exaggerated for clarity. Broken lines illustrate optional features or operations unless specified otherwise.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/ or components, but do not preclude the presence or addition of one or more other features, integers, steps, operations, elements, components, and/or groups thereof. As used herein, the term "and/or" includes any and all combinations of one or more of the associated listed items. As used herein, phrases such as "between X and Y" and "between about X and Y" should be interpreted to include X and Y. As used herein, phrases such as "between about X and Y" mean "between about X and about Y." As used herein, phrases such as "from about X to Y" mean "from about X to about Y."

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein. Well-known functions or constructions may not be described in detail for brevity and/or clarity.

It will be understood that, although the terms first, second, etc. may be used herein to describe various elements, components, regions, layers and/or sections, these elements, components, regions, layers and/or sections should not be limited by these terms. These terms are only used to distinguish one element, component, region, layer or section from another region, layer or section. Thus, a first element, component, region, layer or section discussed below could be termed a second element, component, region, layer or section without departing from the teachings of the present invention. The sequence of operations (or steps) is not limited to the order presented in the claims or figures unless specifically indicated otherwise.

The term "programmatically" means carried out using computer program and/or software, processor or ASIC directed operations. The term "electronic" and derivatives thereof refer to automated or semi-automated operations carried out using devices with electrical circuits and/or modules rather than via mental steps and typically refers to operations that are carried out programmatically. The terms "automated" and "automatic" means that the operations can be carried out with minimal or no manual labor or input. The term "semi-automated" refers to allowing operators some input or activation, but the calculations and signal acquisition as well as the calculation of the concentrations of the ionized constituent(s) are done electronically, typically programmatically, without requiring manual input.

The term "about" refers to +/−10% (mean or average) of a specified value or number.

The term "prediabetes" refers to a patient or subject that has not been diagnosed with type 2 diabetes and, as currently defined by the American Diabetes Association, is associated with individuals that have a fasting plasma glucose level that is between 100 and 125 mg/dL, an oral glucose tolerance test level that is between 140-199 (mg/dL) or an A1C percent that is between 5.7 to 6.4 as represented in Table 1 below (the greater the level, the higher the risk of type 2 diabetes for each type of test.

TABLE 1

Prediabetes and Diabetes Levels
Blood Test Levels for Diagnosis of Diabetes and Prediabetes

|  | A1C (percent) | Fasting Plasma Glucose (mg/dL) | Oral Glucose Tolerance Test (mb/dL |
|---|---|---|---|
| Diabetes | 6.5 or above | 126 or above | 200 or above |
| Prediabetes | 5.7 to 6.4 | 100 to 125 | 140 to 199 |
| Normal | About 5 | 99 or below | 139 or below |

Definitions:
mg = milligram,
dL = deciliter
For all three tests, within the prediabetes range, the higher the test result, the greater the risk of diabetes See, American Diabetes Association. Standards of medical care in diabetes—2012. *Diabetes Care.* 2012:35 (Supp 1):512, table 2. It is contemplated by embodiments of the invention that the use of a diabetes risk score can be used alone or with FPG to diagnose an individual as having prediabetes and can stratify risk for patients having the same FGP but different metabolic issues.

Embodiments of the invention can evaluate a patient's risk of having type 2 diabetes within a 5-7 time frame, typically within about a 5 year time frame as a model of conversion to this condition and may also evaluate whether the patient has prediabetes, impaired fasting glucose or impaired glucose tolerance.

The term "patient" is used broadly and refers to an individual that provides a biosample for testing or analysis.

The term "GlycA" refers to a new biomarker that is derived from a measure of composite NMR signal from carbohydrate portions of acute phase reactant glycoproteins containing N-acetylglucosamine and/or N-acetylgalactosamine moieties, more particularly from the protons of the 2-NAcGlc and 2-NAcGal methyl groups. The GlycA signal is centered at about 2.00 ppm in a plasma NMR spectrum at about 47 degrees C. (+/−0.5 degrees C.). The peak location is independent of spectrometer field but may vary depending on analysis temperature of the biosample and is not found in urine biosamples. Thus, the GlycA peak region may vary if the temperature of the test sample varies. The GlycA NMR signal may include a subset of NMR signal at the defined peak region so as to include only clinically relevant signal contributions and may exclude a protein contribution to the signal in this region as will be discussed further below.

The term "GlycB" refers to a new biomarker that is derived from a measure of composite NMR signal from the carbohydrate portions of acute phase reactant glycoproteins containing N-acetylneuraminic acid (sialic acid) moieties, more particularly from the protons of the 5-Nacetyl methyl groups. The GlycB signal is centered at about 2.04 ppm in the plasma NMR spectrum at about 47 degrees C. The peak location is independent of spectrometer field but may vary depending on analysis temperature of the biosample. Thus, the GlycB peak region may vary if the temperature of the test sample varies (and is not found in urine samples).

As used herein, the chemical shift locations (ppm) refer to NMR spectra referenced internally to CaEDTA signal at 2.519 ppm. Thus, the noted peak locations discussed and/or claimed herein may vary depending on how the chemical shift is generated or referenced as is well known to those of skill in the art. Thus, to be clear, certain of the described and/or claimed peak locations have equivalent different peak locations in other corresponding chemical shifts as is well known to those of skill in the art.

The term "biosample" refers to in vitro blood, plasma, serum, CSF, saliva, lavage, sputum, or tissue samples of humans or animals. Embodiments of the invention may be particularly suitable for evaluating human blood plasma or serum biosamples, particularly for GlycA and GlycB (which are not found in urine, for example). The blood plasma or serum samples may be fasting or non-fasting. Where glucose is measured by NMR, the biosample is typically fasting blood plasma or serum samples.

The terms "population norm" and "standard" refer to values defined by a large study or studies such as the Framingham Offspring Study or the Multi-Ethnic Study of Atherosclerosis (MESA) or other study having a large enough sample to be representative of the general population. However, the instant invention is not limited to the population values in MESA as the presently defined normal and at-risk population values or levels may change over time. Thus, a reference range associated with values from a defined population in risk segments (e.g., quartiles or quintiles) can be provided and used to assess elevated or reduced levels and/or risk of having a clinical disease state.

The term "clinical disease state" means an at-risk medical condition such as prediabetes, that may indicate medical intervention, therapy, therapy adjustment or exclusion of a certain therapy (e.g., pharmaceutical drug) and/or monitoring is appropriate. Identification of a likelihood of a clinical disease such as prediabetes can allow a clinician to treat, delay or inhibit onset of the condition accordingly.

As used herein, the term "NMR spectral analysis" means using proton ($^1$H) nuclear magnetic resonance spectroscopy techniques to obtain data that can measure the respective parameters present in the biosample, e.g., blood plasma or blood serum. "Measuring" and derivatives thereof refers to determining a level or concentration and/or for certain lipoprotein subclasses, measuring the average particle size thereof. The term "NMR derived" means that the associated measurement is calculated using NMR signal/spectra from one or more scans of an in vitro biosample in an NMR spectrometer.

The term "downfield" refers to a region/location on the NMR spectrum that pertains to the left of a certain peak/location/point (higher ppm scale relative to a reference). Conversely, the term "upfield" refers to a region/location on the NMR spectrum that pertains to the right of a certain peak/location/point.

The terms "mathematical model" and "model" are used interchangeably and when used with "DRI", "diabetes risk index", or "risk" refer to a statistical model of risk used to evaluate a subject's risk of developing type 2 diabetes in the future, typically within 5-7 years. The risk model can be or include any suitable model including, but not limited to, one or more of a logistic model, a mixed model or a hierarchical linear model. The risk model can provide a measure of risk based on the probability of conversion to type 2 diabetes within a defined time frame, typically within 5-7 years.

The term "LP-IR™" score refers to an insulin resistance score that rates a subject's insulin sensitivity from insulin sensitive to insulin resistant using a summation of risk scores associated with different defined lipoprotein components. See, e.g., U.S. Pat. No. 8,386,187 for a detailed discussion of the LP-IR score, the contents of which are hereby incorporated by reference as if recited in full herein.

The term "lipoprotein component" refers to a component in the mathematical risk model associated with lipoprotein particles including size and/or concentration of one or more subclasses (subtypes) of lipoproteins. Lipoprotein components can include any of the lipoprotein particle subclasses, concentrations, sizes, ratios and/or mathematical products (multiplied) of lipoprotein parameters and/or lipoprotein subclass measurements of defined lipoprotein parameters combined with other parameters.

The DRI mathematical model can use other clinical parameters such as gender, age, BMI, whether on hypertension medicine and the like.

Lipoproteins include a wide variety of particles found in plasma, serum, whole blood, and lymph, comprising various types and quantities of triglycerides, cholesterol, phospholipids, sphyngolipids, and proteins. These various particles permit the solubilization of otherwise hydrophobic lipid molecules in blood and serve a variety of functions related to lipolysis, lipogenesis, and lipid transport between the gut, liver, muscle tissue and adipose tissue. In blood and/or plasma, lipoproteins have been classified in many ways, generally based on physical properties such as density or electrophoretic mobility.

Figure 11A:
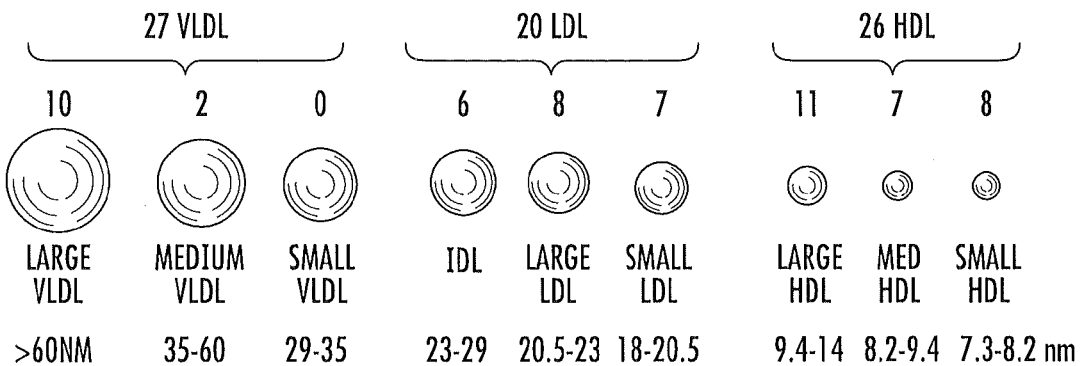
FIGS. 11A and 11B are schematic illustrations of different lipoprotein subpopulations (subclasses) according to embodiments of the present invention.

Classification based on nuclear magnetic resonance-determined particle size distinguishes distinct lipoprotein particles based on size or size ranges. For example, the NMR measurements can identify at least 15 distinct lipoprotein particle subtypes, including at least 5 subtypes of high density lipoproteins (HDL), at least 4 subtypes of low density lipoproteins (LDL), and at least 6 subtypes of very low density lipoproteins (VLDL), which can be designated TRL (triglyceride rich lipoprotein) V1 through V6. As shown in FIG. 11A, current analysis methodology allows NMR measurements that can provide concentrations of 73 subpopulations with 27 VLDL, 20 LDL and 26 HDL subpopulations to produce measurements of groups of defined small and large subpopulations of respective groups.

It is also noted that while NMR measurements of the lipoprotein particles are contemplated as being particularly suitable for the analyses described herein, it is contemplated that other technologies may be used to measure these parameters now or in the future and embodiments of the invention are not limited to this measurement methodology. For example, flotation and ultracentrifugation employ a density-based separation technique for evaluating lipoprotein particles. Ion mobility analysis is a different technology for measuring lipoprotein subclasses.

Figure 11B:
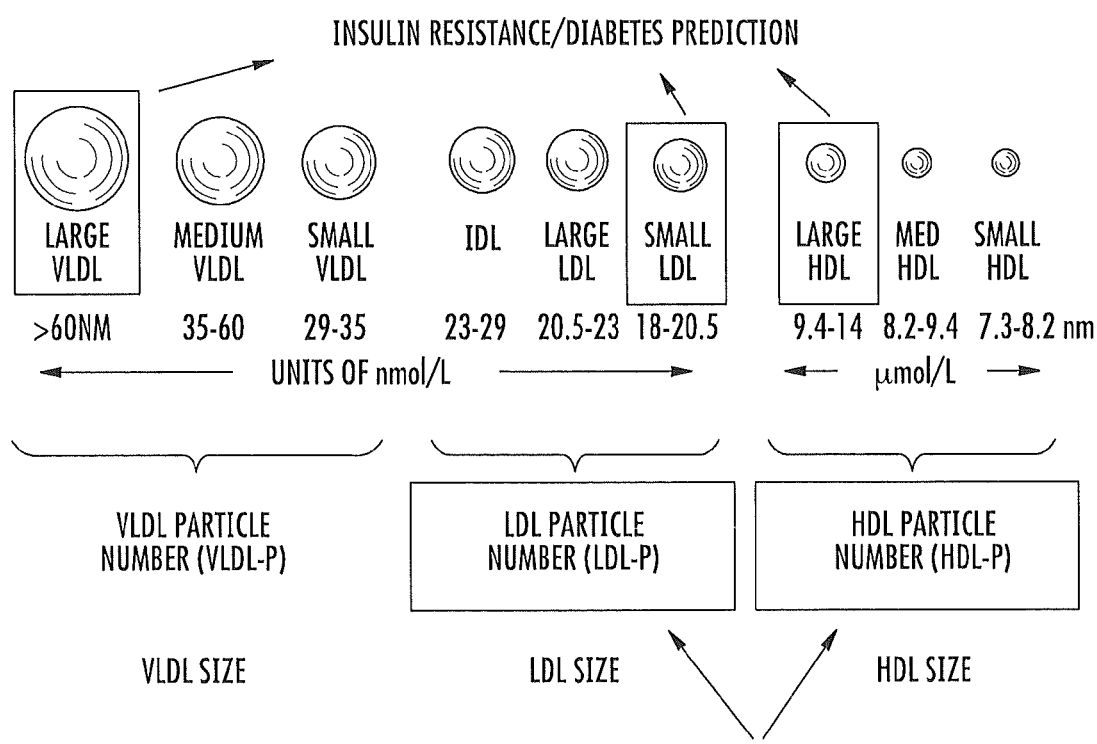

FIG. 11B illustrates examples of lipoprotein subclass groupings, including those with concentrations that can be summed to determine HDL-P and LDL-P numbers according to some particular embodiments of the present invention. Embodiments of the invention classify lipoprotein particles into subclasses grouped by size ranges based on functional/metabolic relatedness as assessed by their correlations with lipid and metabolic variables. Thus, as noted above, the evaluations can measure over 20 discrete subpopulations (sizes) of lipoprotein particles, typically between about 30-80 different size subpopulations (or even more). FIG. 11B also shows these discrete sub-populations can be grouped into defined subclasses, including three each for VLDL and HDL and two or three for LDL (if the former, with one of the three identified as IDL in the size range between large LDL and small VLDL).

For the GlycA and/or GlycB measurement calculations, the discrete number of HDL and LDL groupings can be less than those used to quantitatively measure the lipoprotein subclasses. The subclasses of different size can be quantified from the amplitudes of their spectroscopically distinct lipid methyl group NMR signals. See, Jeyarajah et al., *Lipoprotein particle analysis by nuclear magnetic resonance spectroscopy*, Clin Lab Med. 2006; 26: pp. 847-870, the contents of which are hereby incorporated by reference as if recited in full herein. The NMR derived HDL-P and LDL-P particle sizes noted herein typically refer to average measurements, but other size demarcations may be used.

The term "LDL-P" refers to a low density lipoprotein particle number (LDL-P) measurement (e.g., LDL-P number) that sums the concentration of defined LDL subclasses. Total LDL-P can be generated using a total low density lipoprotein particle (LDL-P) measurement that sums the concentration (μmol/L) of all the LDL subclasses (large and small) including sizes between 18-23 nm. In some embodiments, the LDL-P measurement may employ selected combinations of the LDL subclasses (rather than the total of all LDL subclass subpopulations). As used herein, the term "small LDL particles" typically includes particles whose sizes range from between about 18 to less than 20.5 nm, typically between 19-20 nm. The term "large LDL particles" includes particles ranging in diameter from between about 20.5-23 nm. It is noted that the LDL subclasses of particles can be divided in other size ranges. For example, the "small" size may be between about 19-20.5 nm, intermediate may be between about 20.5-21.2 nm, and large may be between about 21.2-23 nm. In addition, intermediate-density lipoprotein particles ("IDL" or "IDL-P"), which range in diameter from between about 23-29 nm, can be included among the particles defined as "large" LDL (or even small VLDL). Thus, for example, the LDL subclasses can be between 19-28 nm.

The term "HDL-P" refers to a high density lipoprotein particle number (HDL-P) measurement (e.g., HDL-P number) that sums the concentration of defined HDL subclasses. Total HDL-P can be generated using a total high density lipoprotein particle (HDL-P) measurement that sums the concentration (μmol/L) of all the HDL subclasses (large, medium and small) in the size range between about 7 nm (on average) to about 14 nm (on average), typically between 7.4-13.5 nm. In some embodiments, the HDL-P measurement may employ selected combinations of the HDL subclasses (rather than all subpopulations of HDL subclasses). The term "large HDL particles" ("large HDL-P") typically includes HDL subclasses of particles whose sizes range from between about 9.4 to about 14 nm, and may be defined for particles with sizes between 9.7-13.5 nm. The term "small HDL particles" (small HDL-P) typically includes particles ranging in diameter between about 7 (typically about 7.3 or 7.4 nm) to about 8.2 nm. The intermediate or medium HDL particles (medium HDL-P) can be parsed into one of the small or large designations or be measured separately as including particles in the size range that is typically between about 8.2 to 9.4 nm, such as 8.3-9.4 nm. Thus, either or both the ranges of size above can be broadened to include some or all the sizes of the intermediate HDL particles.

HDL subclass particles typically range (on average) from between about 7 nm to about 15 nm, more typically about 7.3 nm to about 14 nm (e.g., 7.4 nm-13.5 nm). The HDL-P concentration is the sum of the particle concentrations of the respective subpopulations of its HDL-subclasses, e.g., small HDL-P can include H1-H8, H1-H9, H1-H10 or H1-H11 subpopulations, for example.

The different subpopulations of HDL-P can be identified by a number from 1-26, with "1" representing the lowest size subpopulation in the HDL subclass and "26" being the largest size subpopulation in the HDL subclass. The small HDL components can include H1-H8, or H1-H11 and the large HDL components including H16-H26.

The term "large VLDL particles" refers to particles at or above 60 nm such as between 60-260 nm. The term "medium VLDL particles" refers to particles in sizes between 35-60 nm. The term "small VLDL particles" refers to particles between 29-35 nm. The term "VLDL-P" refers to a very low density lipoprotein particle number (VLDL-P) measurement (e.g., VLDL-P number) that sums the concentration of defined VLDL subclasses. Total VLDL-P can be generated using a total very low density lipoprotein particle (HDL-P) measurement that sums the concentration (μmol/L) of all the VLDL subclasses (large, medium and small).

It is noted that the "small, large and medium" size ranges noted above can vary or be redefined to widen or narrow the upper or lower end values thereof. The particle sizes noted above typically refer to average measurements, but other demarcations may be used.

As is known to those of skill in the art, valine is an α-amino acid with the chemical formula $HO_2CCH(NH_2)CH(CH_3)_2$. When measured by NMR, the value can be unitless. The valine measurement may be multiplied by a defined conversion factor to convert the value into concentration units.

Inflammation can be associated with many different disease states including, but not limited to prediabetes, T2DM and CHD. It is also believed that inflammation may modulate HDL functionality. See, e.g., Fogelman, When Good Cholesterol Goes Bad, Nature Medicine, 2004. Carbohydrate components of glycoproteins can perform biological functions in protein sorting, immune and receptor recognition, inflammation and other cellular processes.

Generally stated, embodiments of the present invention provide at least one Diabetes Risk Index (DRI) using one or more defined mathematical models of risk of different defined biomarkers or parameters of an in vitro biosample of a patient to identify at-risk patients before onset of T2DM who may benefit from pharmaceutical, medical, diet, exercise or other intervention.

The DRI model(s) can include at least one inflammatory marker, at least one lipoprotein component and at least one other defined metabolite or biomarker.

In preferred embodiments, the DRI risk progression model parameters can include NMR derived measurements of deconvolved signal associated with a common NMR spectrum of lipoproteins using defined deconvolution models that characterize deconvolution components for protein and lipoproteins, including HDL, LDL, VLDL/chylos. This type of analysis can provide for a rapid scan acquisition time of under 1 minute, typically between about 20 s-40 s, and corresponding rapid programmatic calculations to generate measurements of the model components, then programmatic calculation of one or more DRI risk scores using one or more defined risk models.

However, in some embodiments, it is contemplated that alternate (water suppression) pulse sequences can be used to suppress proteins and reveal small metabolites that can be quantified.

Inflammatory Markers

The model may include one or more inflammatory markers including: GlycA and GlycB.

Other Metabolites

Figure 3A:
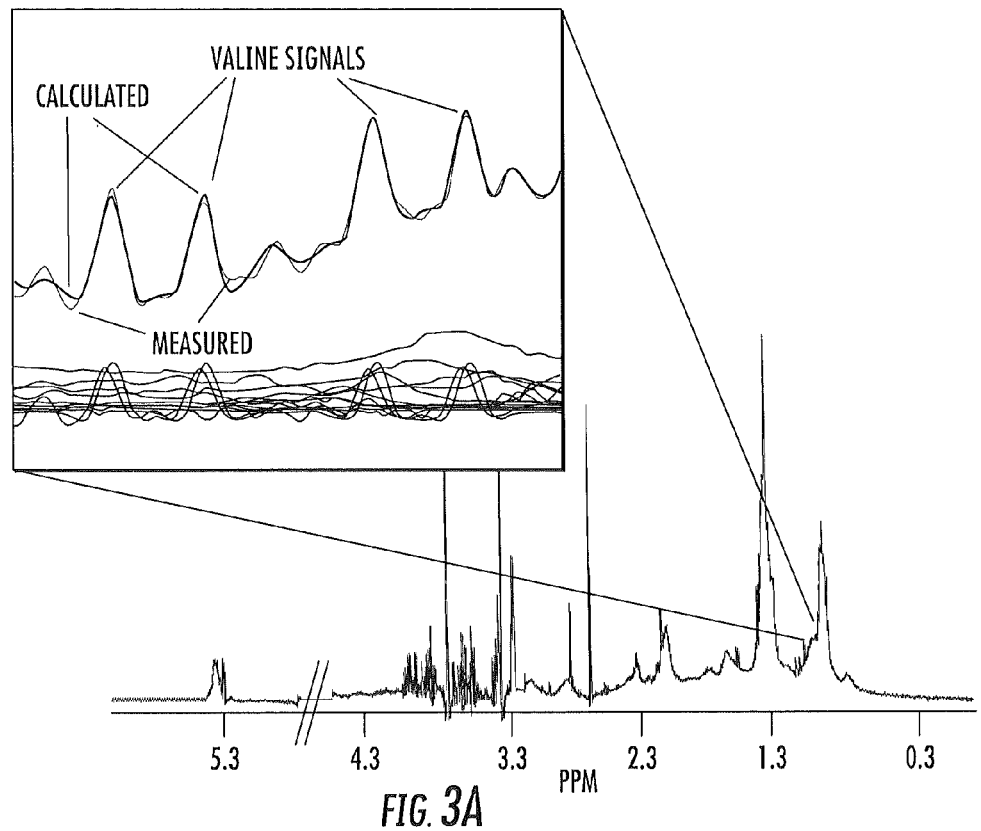
FIG. 3A is an example of a fitting function/deconvolution model that uses four valine (quartet) signals to calculate NMR measures of valine according to embodiments of the present invention.
Figure 3B:
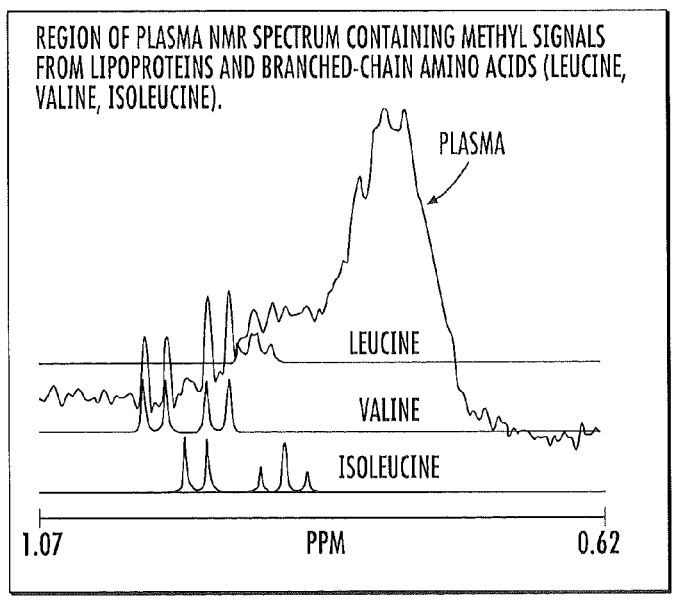
FIG. 3B is an expansion of the plasma NMR spectrum containing methyl signals from lipoproteins and branched-chain amino acids according to embodiments of the present invention.
Figure 3C:
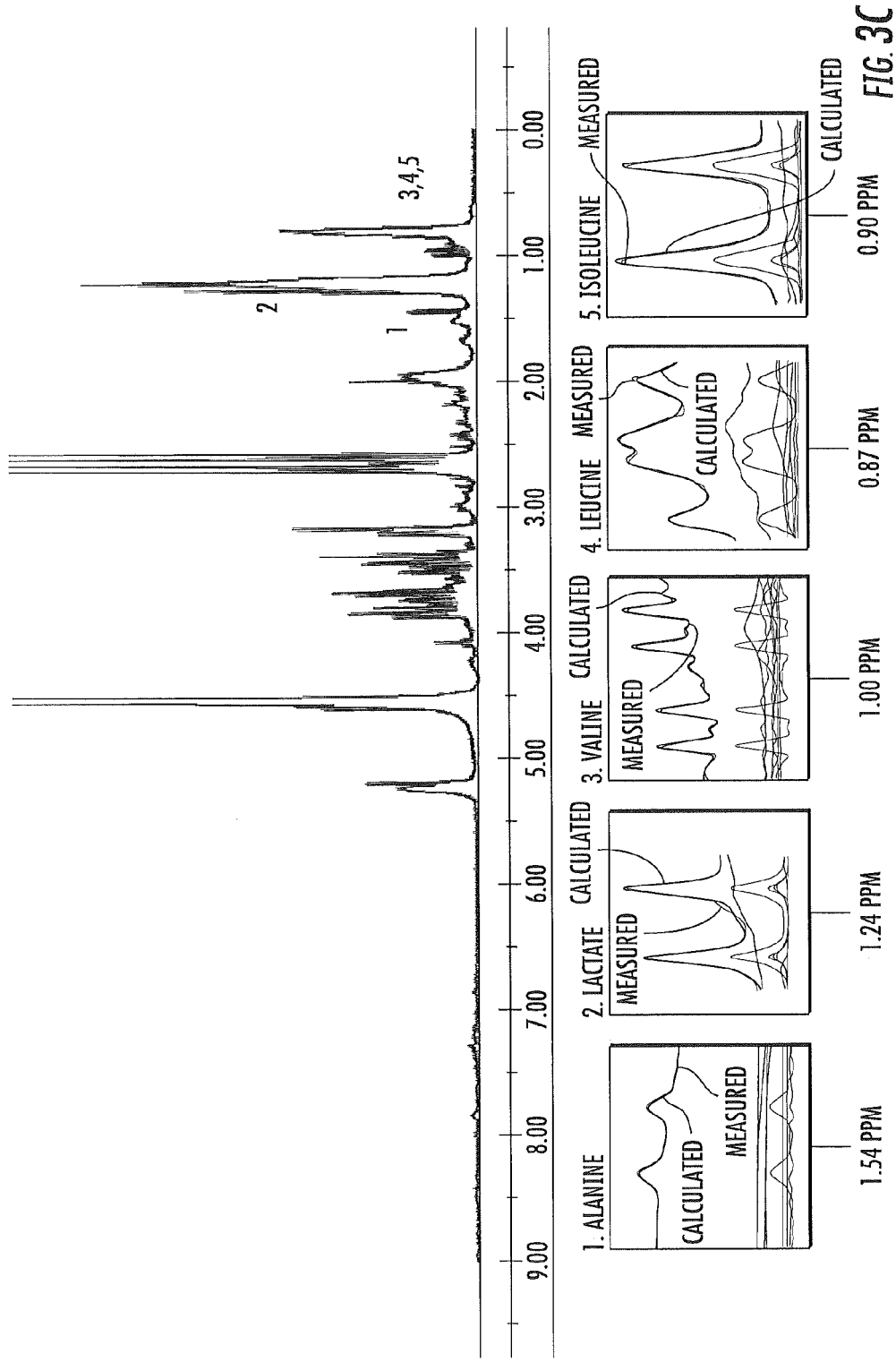
FIG. 3C shows the full NMR spectrum containing methyl signals from lipoproteins and branched-chain amino acids with an expansion showing the location of signals from the noted metabolites according to embodiments of the present invention.

FIG. 3C illustrates NMR detectable metabolites that may be quantified in NMR spectra using defined deconvolution models of lipoproteins. As shown, the DRI model may include one or more branched chain amino acids including one or more of isoleucine, leucine, and valine (as discussed above) or one or more NMR detectable metabolites such as lactate alanine, acetone, acetoacetic acid, and beta-hydroxybutiric acid with closely aligned calculated and measured lines (for contemplated associated deconvolution models) for each illustrated. The associated centers of peak regions for the respective metabolites isoleucine, leucine, valine, lactate, and alanine are shown in FIG. 3C (0.90 ppm, 0.87 ppm, 1.00 ppm, 1.24 ppm, and 1.54 ppm, respectively).

It is contemplated that other metabolites can be measured by NMR, perhaps using a CPMG pulse sequence, can include choline, phosphocholine, glycine, glycerol, a- and b-hydroxybutyrate and carnitine.

LP-IR Score

The risk progression model may include the LP-IR™ score as a separate component from another lipoprotein component.

Lipoprotein Components

The model can include one or more (typically a plurality of) lipoprotein components such as, for example, HDL-P, LDL-P, ratios, sums, and/or products of lipoprotein components. Table 2 below illustrates some correlations identified with exemplary lipoproteins.

TABLE 2

MESA, New Diabetes prediction

| Logistic regression, models adjusted on gender, age, ethnicity | All, N = 411 (4983) | | Glucose 90-110 mg/dL N = 210 (2038) | |
|---|---|---|---|---|
| NMR parameters | X2 | P | X2 | P |
| VLDL size | 73.5 | <0.0001 | 27.1 | <0.0001 |
| LDL size | −51.3 | <0.0001 | −18.5 | <0.0001 |
| HDL size | −47.7 | <0.0001 | −12.4 | 0.0004 |
| Large VLDL | 37.9 | <0.0001 | 7.74 | 0.0054 |
| Medium VLDL | 2.57 | 0.1088 | 0.27 | |
| Small VLDL | −1.72 | | −2.6 | 0.1067 |
| IDL | −0.017 | | −0.32 | |
| Large LDL | −15.47 | <0.0001 | −6.83 | 0.009 |
| Small LDL | 51.4 | <0.0001 | 17.03 | <0.0001 |
| Large HDL | −45.5 | <0.0001 | −10.31 | 0.0013 |
| Medium HDL | −24.4 | <0.0001 | −9.5 | 0.0021 |
| Small HDL | 43.6 | <0.0001 | 13.1 | 0.0003 |

In some embodiments, values of some or all of the different parameters can be derived from a single nuclear magnetic resonance (NMR) spectrum of a biosample, typically a fasting blood plasma or serum sample.

The DRI models can include lipoprotein subclass/size parameters and GlycA. In some preferred embodiments, the DRI mathematical model also includes the branched-chain amino acid valine. Optionally, glucose may also be considered as a risk parameter in the DRI model. Where used, a patient's glucose measurement may also be obtained from the NMR spectrum of the biosample or may be obtained in other conventional manners.

The DRI model(s) can incorporate lipoprotein subclass parameters that are known to be drug-resistant or drug-sensitive along with the insulin sensitive lipoproteins. The DRI mathematical model(s) can include gender as a variable or may be configured as different models for different genders. The DRI models for a respective patient can be electronically adjusted or selected depending on one or more factors associated with the patient, e.g., gender of the patient, age of the patient, whether the patient is on a certain type of medication and the like.

FIG. 1 is a graph that presents diabetes conversion rates of subjects within 6 glucose subgroups (dotted line), for those subjects in the upper and lower quartile of diabetes risk index values within each glucose stratum. As shown, the risk of developing diabetes at any given glucose level is substantially greater for DRI index values in Q4 vs Q1. Notably, the diabetes risk index can actually be a better predictor than glucose alone. It is contemplated that an NMR-based diabetes risk score can effectively stratify risk without requiring additional clinical information.

The diabetes risk index calculation can be carried out to generate diabetes risk index correlated to ranges of fasting plasma glucose (FPG) mg/dL, which typically ranges from about 90-126, with some people having less and some having higher values at each end of the range. As noted above FPG values 100-125 mg/dL can be associated with "prediabetes." Values between 100-110 FPG mg/dl are typically associated with increased "early" intervention risk. Values between 110-125 FPG mg/dL are typically associated with later stage or greater risk than the "early" stage or lower FPG values.

A person's risk of developing T2DM can be presented as a DRI index score with respect to a defined range of risk, from low to high risk. The "index" can be a simple guide or predictor of a person's risk status. The diabetes risk index is generated from a statistically validated mathematical model of risk that can characterize a subject's risk of developing T2DM in a future timeframe, in a range of from low (e.g., less likely) to high (more likely) relative to a population norm. The "low" value can be associated with DRI values that are in the lower half of a population norm. High risk DRI values can be associated with DRI values in a fourth quartile or fourth or fifth quintile of a population norm and indicates a high likelihood of convergence to type 2 diabetes within the next 5-7 years and therefore having prediabetes. Intermediate risk DRI values can be associated with values in a top half of a population norm but below high risk values.

While it is contemplated that the DRI index will be particularly useful when provided as a numerical score, the risk index can be presented on a patient report in different manners. The DRI index can be provided as a result expressed numerically or alphanumerically, typically comprising a numerical score on a defined scale or within a defined range of values. For example, in particular embodiments, the DRI risk index can be provided as or include a score within a defined range, such as, for example, between 0-0.1, 0-1, 0-10, 0-24, 0-100, or 0-1000 and the like. Typically, the lowest number is associated with the least risk and the higher numbers are associated with increased risk of developing T2DM in the future, typically within 5-7 years although over time frames may be used for some embodiments. The lower value in the range may be above "0" such as 1, 2, 3, 4 or 5 and the like, or may even be a negative number (e.g., −1, −2, −3, 4, −5 and the like). Other index examples, include, for example, alphanumeric indexes or even icons noting degrees of risk, including but not limited to, "LR1" (low risk), IR5 (intermediate risk) and "HR9" (high risk), terms such as "DRI positive", "DRI high", "DRI neutral", "DRI low", "DRI good", "DRI bad", "DRI watch" and the like.

As noted above, the diabetes risk index models can include or omit glucose as a parameter or may use FPG or other glucose measurement as a separate parameter used with a DRI score to characterize risk.

In some embodiments, for example, where the a patient has a diabetes risk index that is in the fourth quartile or fourth or fifth quintile of a population norm, the patient can be identified as having prediabetes, as a likelihood of having prediabetes, as at risk for diabetes, as having modest hyperglycemia, as having impaired fasting glucose or impaired glucose tolerance or being insulin resistant.

In some embodiments, the diabetes risk index can be provided without a glucose measurement and/or without including such a measurement in the model. Thus a DRI score in the fourth quartile or fourth or fifth quintile, alone, can identify those at risk of developing diabetes in the next 5-7 years.

In some embodiments, such as where the diabetes risk index is in the third or fourth quartile or in the fourth or fifth quintile and has a glucose measurement (e.g., for FPG measurement) that is above 95 mg/dl, typically between 100-125 mg/dl, the patient can be identified as having prediabetes or as at increased risk or associated with a likelihood of developing T2DM in the future, typically within about 5-7 years but other time frames may be utilized. Other glucose measurements may also be used (see, for example, Table 1).

As shown with respect to FIG. 1, the risk of developing diabetes in the future at any given glucose level is substantially greater where the DRI value is in Q4 versus Q1. Thus, the DRI can be a simple NMR-based risk score that can effectively stratify risk without requiring additional clinical information.

In some embodiments, gender may be a factor in the diabetes risk index model. In some embodiments, age may be a factor in the diabetes risk index model. In other embodiments, the diabetes risk index can exclude either gender or age considerations so as to avoid generating false negatives or false positives based on data corruption of such ancillary data not directly tied to a biosample, for example.

The DRI index can be generated in one or more than one way for a particular patient and two or more DRI indexes can be generated for comparison, for elective use of one or both by a clinician and/or presented as a ratio of the two. For example, the NMR data can be evaluated using a plurality of different DRI index calculation models where one model can employ lipoprotein components that are sensitive to a particular drug therapy or class of therapies (e.g., statins) and one that includes lipoprotein components that are insensitive (or immune) to such particular therapy or class of therapies.

TABLE 3

Lipoprotein Components/Parameters Statin Sensitivity/Resistance

| | Affected by statins - YES | Affected by statins - NO |
|---|---|---|
| VLDL size | — | NO |
| Small HDL-P | — | NO |
| Large VLDL-P | Yes | |
| Small LDL-P | Yes | — |
| Large HDL-P | Yes | |
| LDL size | Yes | |
| HDL size | Yes | |
| Medium HDL-P | Yes | |

By way of another example the DRI risk score can be calculated in two or more ways, one using components that are more robust where non-fasting (blood plasma or serum) biosamples are analyzed and one that may have a better risk prediction value but is for fasting biosamples. For example, VLDL components may be reduced or excluded from DRI models for non-fasting samples. Table 4 lists lipoprotein components that can be affected by nonfasting.

TABLE 4

Lipoprotein components sensitive to nonfasting.

| Lipoprotein Components | Sensitivity to Nonfasting |
|---|---|
| LPIR | Great |
| Large VLDL | Great |
| Medium VLDL | Great |
| Small VLDL | Great |
| VLDL size | Great |
| Small LDL-P | Minimal |
| Large LDL-P | Minimal |
| LDL size | Minimal |
| Large HDL-P | Minimal |
| Medium HDL-P | Moderate |
| Small HDL-P | Moderate |
| HDL size | Minimal |
| GlycA | Minimal |
| Valine | Minimal |
| Glucose | Great |

Similarly, the DRI risk evaluations can be calculated using both the statin sensitive and statin insensitive DRI models allowing the clinician rather than the testing protocol analysis circuit to assess which applies to a particular patient. The different values can be presented in a report or on a display with a comment on the different results.

In some embodiments, only one DRI score is provided to the clinician based on data electronically correlated to the sample or based on clinician or intake lab input, e.g., fasting "F" or non-fasting "NF," and statin "S" or non-statin "NS" characterizations of the patient which data can be provided on labels associated with the biosample to be electronically associated with the sample at the NMR analyzer 22. Alternatively, the patient characterization data can be held in a computer database (remote or via server or other defined pathway) and can include a patient identifier, sample type, test type, and the like entered into an electronic correlation file by a clinician or intake laboratory that can be accessed by or hosted by the intake laboratory that communicates with the NMR analyzer 22. The patient characterization data can allow the appropriate DRI model to be used for a particular patient.

HDL-P can be in μmol/L units. VLDL-P and LDL-P can be in units of nmol/L. Valine and/or GlycA, where used, can be in arbitrary units or one or each can be multiplied by a respective defined conversion factor to provide the number in units of μM/μmol/L, respectively (see, e.g., FIG. 10 for GlycA).

It is contemplated that a diabetes risk index can be used to monitor subjects in clinical trials and/or on drug therapies, to identify drug contradictions, and/or to monitor for changes in risk status (positive or negative) that may be associated with a particular drug, a patient's lifestyle and the like, which may be patient-specific.

Further discussion of diabetes risk prediction models is provided below after discussion of examples of NMR signal deconvolution methods that can be used to obtain the GlycA/GlycB measurement and, where used, a valine measurement.

Figure 2:
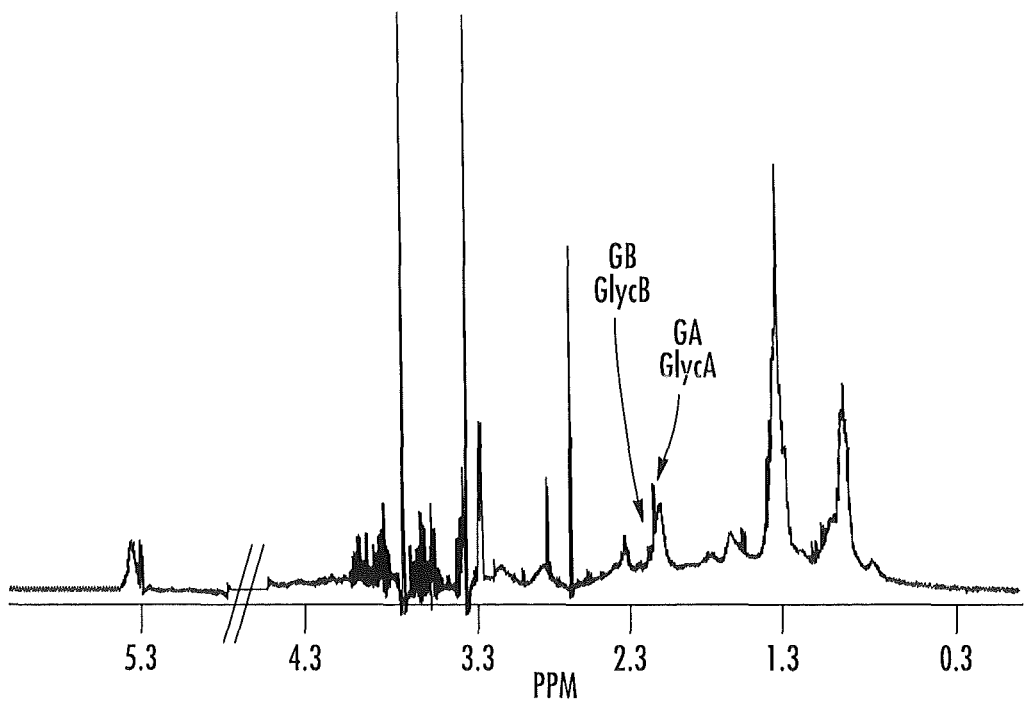
FIG. 2 is an NMR spectrum showing inflammation markers in the plasma NMR spectrum (N-acetyl methyl signals from glycosylated acute phase proteins) associated with defined NMR markers, GlycA and GlycB, respectively, according to embodiments of the present invention.

FIG. 2 illustrates the resonant peak regions for GA associated with GlycA and GB associated with GlycB in the plasma NMR spectrum. One or both of these peak regions can include signal that can be defined as inflammation markers in the plasma NMR spectrum.

Figure 5A:
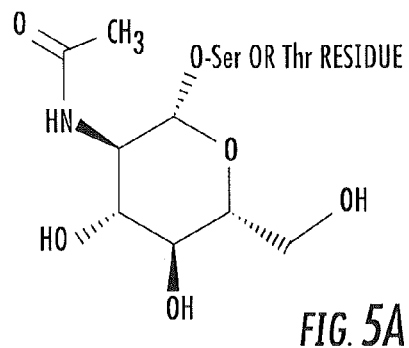
FIGS. 5A and 5B are schematic illustrations of the chemical structures of the carbohydrate portion of N-acetylglycosylated proteins showing the CH3 group that gives rise to the GlycA NMR signal.
Figure 5B:
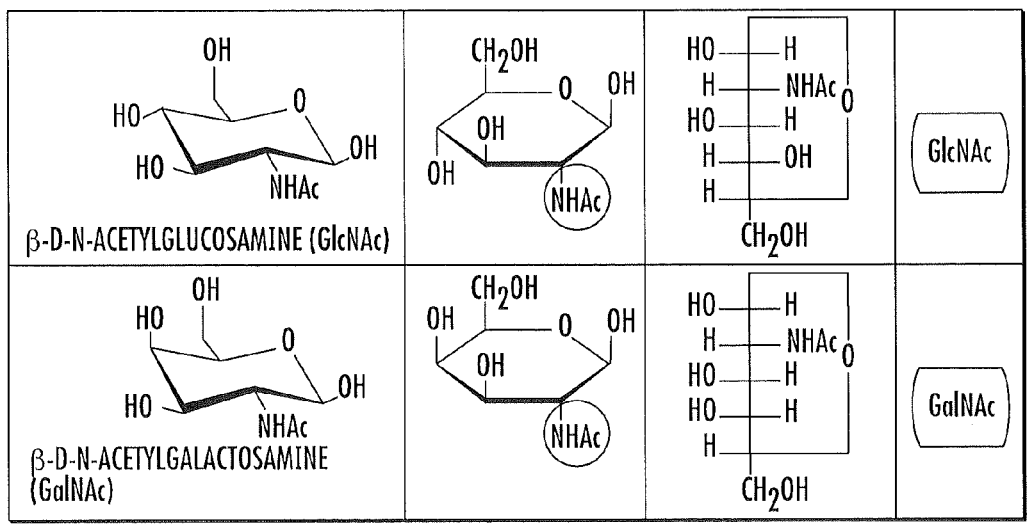
Figure 6A:
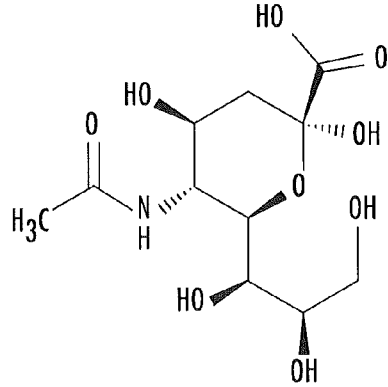
FIGS. 6A and 6B are schematic illustrations of the chemical structures of the carbohydrate portion of N-acetylneuraminic acid modified glycoproteins showing the CH3 group that gives rise to the GlycB NMR signal.
Figure 6B:
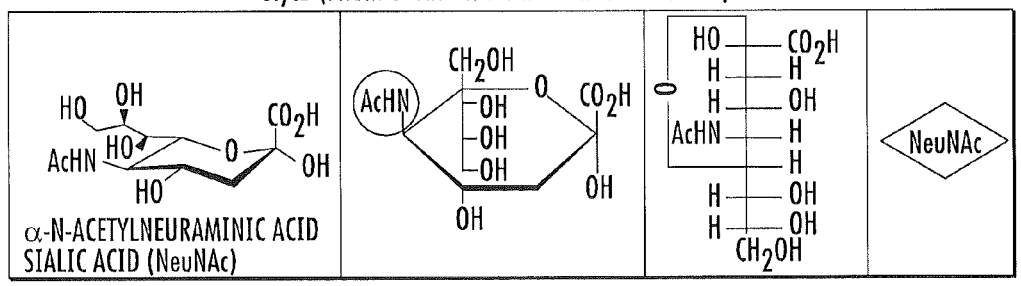

FIGS. 5A/5B illustrates the chemical structure of the carbohydrate portion of N-acetylglycosylated proteins showing the $CH_3$ group that gives rise to the GlycA NMR signal. FIGS. 6A/6B illustrates the chemical structure of the carbohydrate portion of N-acetylneuraminic acid (also called sialic acid) modified glycoproteins showing the $CH_3$ group that gives rise to the GlycB NMR signal.

FIG. 3A is an example of a deconvolved signal shown in FIG. 3B with a quartet of valine signals identified to generate a calculated Vc and measured Vm spectrum of the valine peaks of valine signal that can be used to measure valine (in the embodiment shown, the biosample is blood plasma or serum. One or more of the quartet of peaks of valine are located within a region between about 0.72 ppm to about 1.07 ppm. Typically, one or more of the quartet of peaks of valine are located between 0.9 ppm and 1.03 ppm, e.g., at a center of the multiplet region at about 1.00 ppm of the downfield methyl doublets. One or more of the quartet of peaks of valine can be used to measure valine in the biosample. The concentration of valine in urine is significantly higher than that in serum/plasma, and peak position and amplitude will be different.

FIG. 3B is an enlarged region of plasma NMR spectrum (1.07-0.62 ppm) containing methyl signals from lipoproteins and branched-chain amino acids (leucine, valine and isoleucine).

As shown in FIG. 3C, the DRI model may include one or more of isoleucine, leucine, valine (as discussed above), lactate, and alanine with closely aligned calculated and measured lines (for contemplated associated deconvolution models) for each illustrated. The associated centers of peak regions of the respective metabolites are shown in FIG. 3C (0.90 ppm, 0.87 ppm, 1.00 ppm, 1.24 ppm, and 1.54 ppm, respectively).

Figure 4A:
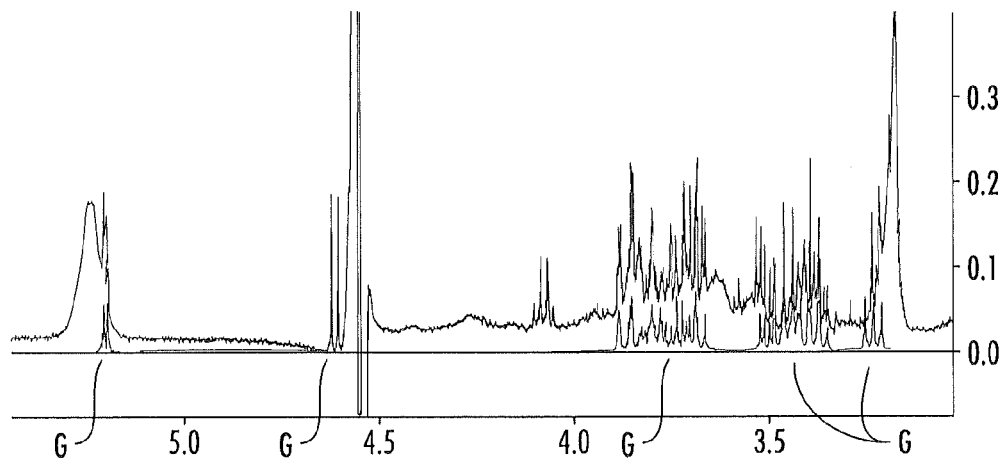
FIG. 4A is an NMR spectrum showing glucose signal as multiplets at several locations according to embodiments of the present invention.

FIG. 4A is an NMR spectrum of a serum sample with a glucose spectrum shown below the upper spectrum. There is a glucose multiplet at 5.2 ppm, and glucose multiplets centered at 4.6, 3.9, 3.8, 3.7, 3.5, 3.4 and 3.2 ppm which could be used for measuring glucose using NMR derived measurements.

Figure 4B:
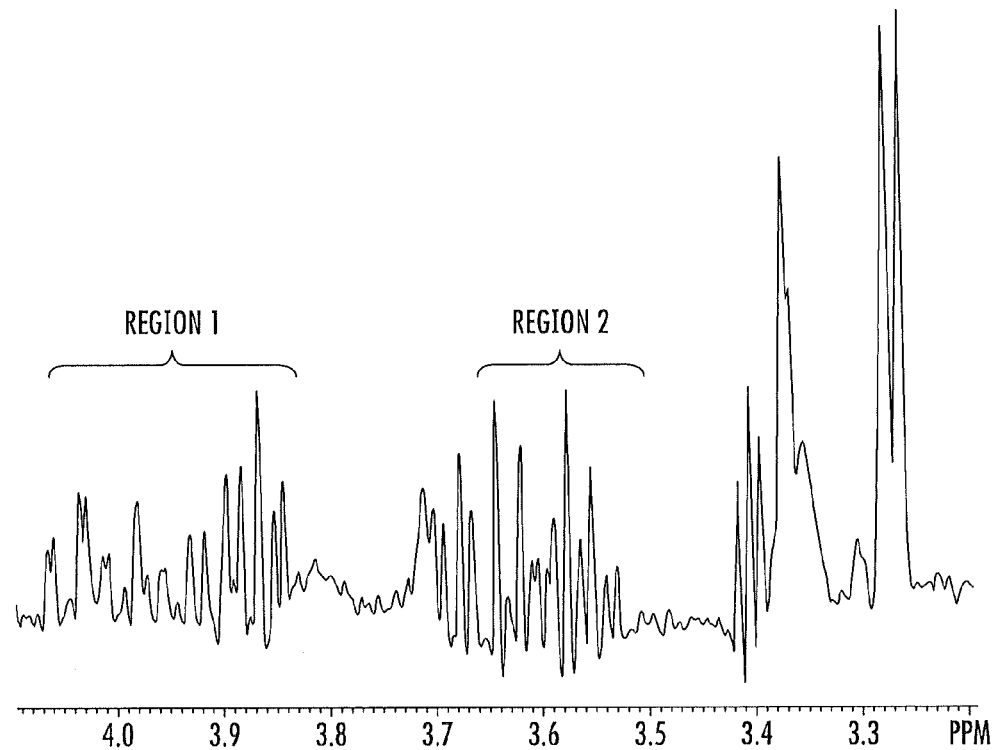
FIG. 4B is a region of the blood plasma proton NMR spectrum containing glucose peaks according to embodiments of the present invention.

FIG. 4B shows the proton NMR spectrum of blood plasma, with the two regions (region 1 and region 2) containing the signals produced by glucose indicated. In some particular embodiments, the peaks in region 1 in the range of 3.81-4.04 ppm can be used for glucose analysis according to some embodiments of the present invention. Alternatively, the peaks in region 2 in the range of 3.50-3.63 ppm can be used for the glucose analysis of the present invention. Additionally, the combination of the peaks in region 1 and region 2, may be used for the quantitative determination of glucose according to the present invention. The data points in the reference or standard spectrum and patient glucose sample spectra are aligned using a line-shape fitting process as described herein to find the "best fit," and the intensity of the standard spectrum is scaled to match the sample spectrum. The glucose concentration of the standard is multiplied by the scaling factor used to match the sample lineshape to give the glucose concentration of the blood sample. See, e.g., U.S. Pat. No. 6,518,069 for further discussion of the glucose and lipoprotein measurements for assessing risk of developing Type 2 diabetes, the contents of which are hereby incorporated by reference as if recited in full herein.

Thus, in some embodiments, a patient glucose measurement can be obtained via NMR analysis of the biosample NMR spectrum, along with lipoprotein particle measurements, GlycA and valine measurements. However, glucose measurements, where used, can alternatively be obtained in conventional chemical ways.

It is contemplated that NMR measurements of GlycA, valine, and lipoproteins of a single (blood/plasma) in vitro biosample can provide important clinical information and/or further improve a prediction or evaluation of a patient or subject's risk of developing type 2 diabetes and/or having prediabetes.

Figure 7A:
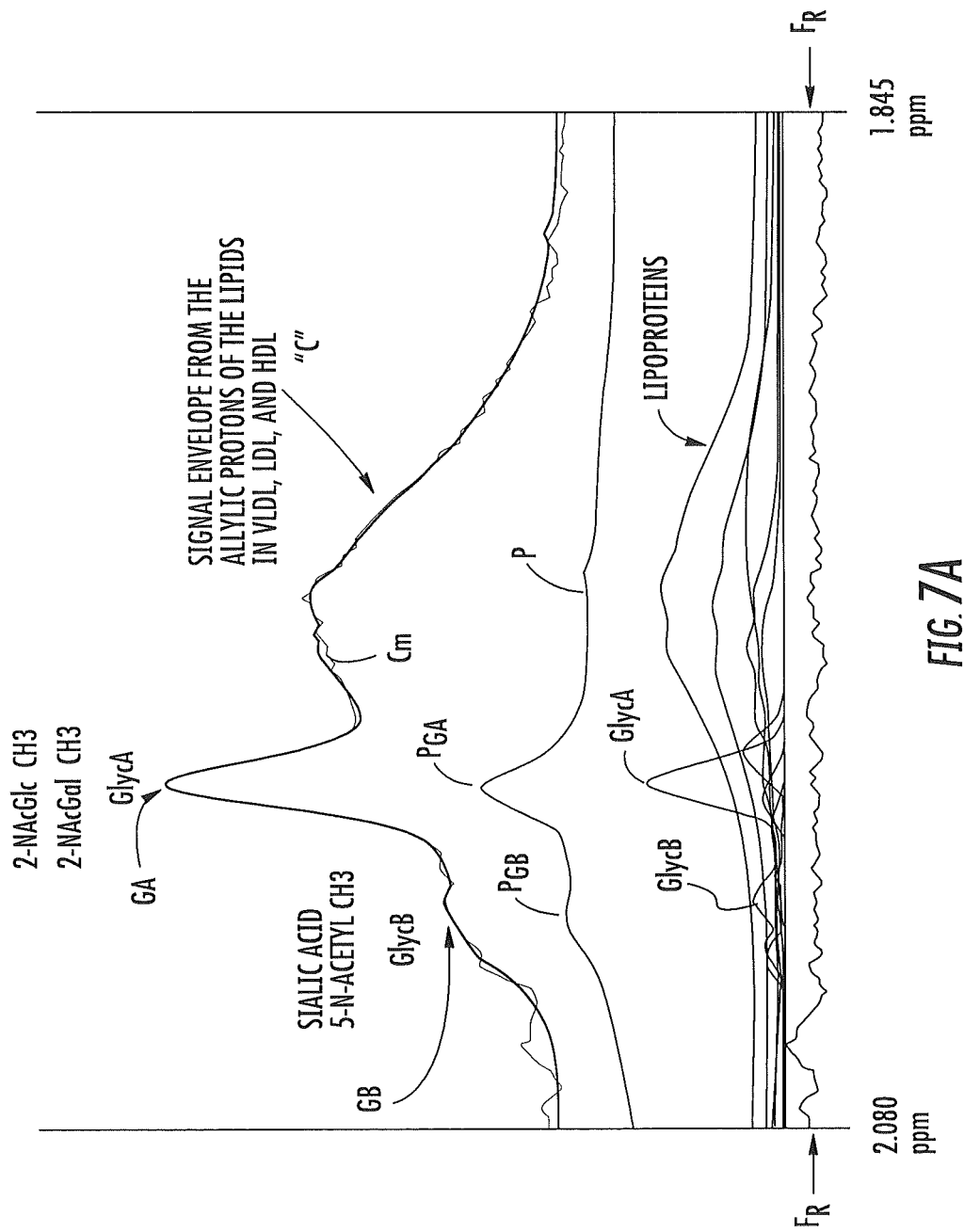
FIG. 7A is a graph showing an expanded section of the plasma NMR spectrum containing the signal envelope from the plasma lipoproteins and the underlying GlycA and GlycB signals according to embodiments of the present invention.

FIG. 7A illustrates an enlarged chemical shift portion of the NMR spectrum between 2.080 and 1.845 ppm as shown in FIG. 2. FIG. 7A also illustrates both the calculated C signal and the measured (composite) signal envelope Cm from the allylic protons of the lipids in VLDL, LDL and HDL, with underlying deconvolved GlycA and GlycB and other resonant peaks. GlycA can include contributions from 2-NAcGlc and 2-NAcGal methyl groups. GlycB includes signal from the N-acetyl methyl groups on the sialic acid moieties of glycoproteins.

A defined lineshape GlycA mathematical deconvolution model can be used to measure the GlycA. The "composite" or measured signal envelope Cm can be deconvolved to quantify the signal contributions of GlycA and other contributing components such as lipoprotein subclass components. The deconvolution calculates signal amplitudes of the components contributing to the measured signal shapes and calculates the sum of the components. A close match between the calculated signal C and the measured signal Cm indicates the deconvolution successfully modeled the components that make up the NMR signal.

The peak region of the GlycA region GA and the peak of the GlycB region GB are shown by the peaks centered at 2.00 ppm and 2.04 ppm (at about 47 deg C. sample temperature), respectively, underlying the composite (upper) envelope signal line Cm. In some embodiments, the peak regions for GlycA and GlycB can include adjacent smaller nearby signals in the deconvolution model to account for GlycA and GlycB signals of slightly different frequency.

The protein signal Ps includes "humps" or peaks $P_{GA}$ and $P_{GB}$ that align with GA and GB, respectively. GlycA can be calculated using the difference between total plasma GlycA signal or "GA" as given by the total peak area of the plasma GlycA signal and "$P_{GA}$", that portion of GlycA that may derive from the non-inflammatory glycoproteins in the protein (d>1.21 g/L) component of plasma. The deconvolution can be carried out to subtract out the (patient/subject) variable "clinically non-informative" part of the total NMR signal at the GA region to leave the more informative disease association measure of GlycA.

Stated differently, while not being bound to any particular theory, in some embodiments, the measured GlycA signal at 2.00 ppm can be referred to as GA, the deconvolution can separate it into three parts: 1) the part contributed to by the protein (d>1.21 g/L) chosen to be largely devoid of inflammatory proteins, 2) the part contributed to by the "non-inflammatory" lipoproteins (d<1.21 g/L), and 3) the inflammatory glycoproteins (both lipoprotein and protein), the latter modeled by the overlapping Lorentzians (LGA) or other curve fit functions. The clinically informative GlycA from the deconvolution can be defined as GA minus $P_{GA}$ and minus the non-inflammatory lipoprotein components=LGA. GlycB can be determined in a similar manner using the GB minus $P_{GB}$ signal contribution minus the non-inflammatory lipoprotein components.

The lineshape deconvolution can be achieved with a non-negative least squares fitting program (Lawson, C L, Hanson R J, Solving Least Squares Problems, Englewood Cliffs, N.J., Prentice-Hall, 1974). This avoids the use of negative concentrations which can lead to error especially in low signal to noise spectra. Mathematically, a suitable lineshape analysis is described in detail for lipoproteins in the paper by Otvos, J D, Jeyarajah, E J and Bennett, D W, Clin Chem, 37, 377, 1991. A synthetic baseline correction function may also be used to account for baseline offsets from residual protein components. This can take the form of a quadratic or other polynomial function. Weighting factors are determined and the fit can be optimized by minimizing the root mean squared deviation between the experimental and calculated spectrum. See, e.g., U.S. Pat. Nos. 4,933,844 and 6,617,167 for a description of deconvolving composite NMR spectra to measure subclasses of lipoproteins, the contents of which are hereby incorporated by reference as if recited in full herein. See also, U.S. Pat. No. 7,243,030 for a description of a protocol to deconvolve chemical constituents with overlapping signal contribution, the contents of which are hereby incorporated by reference as if recited in full herein.

Figure 7B:
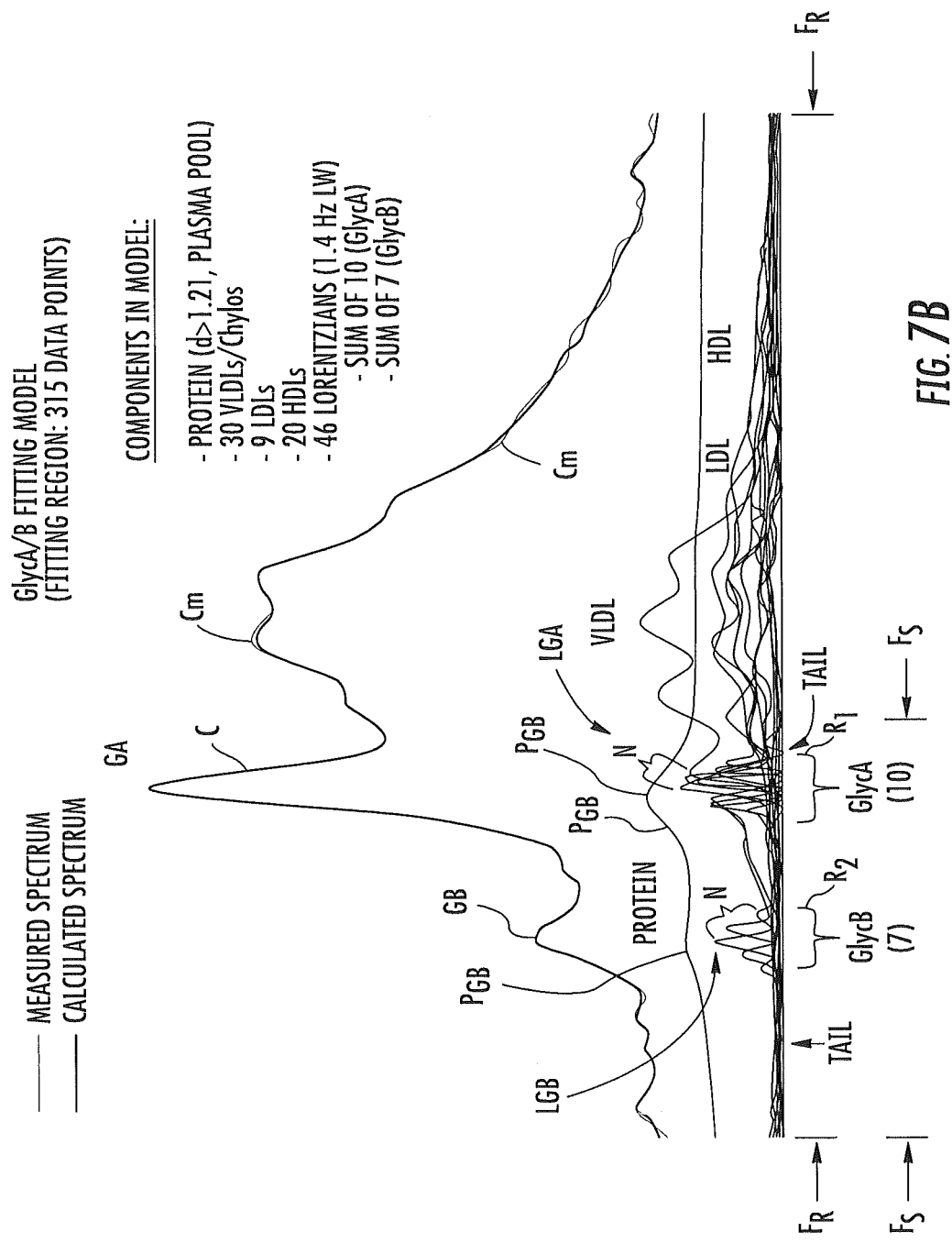
FIGS. 7B and 7C are graphs of the NMR spectral region shown in FIG. 7A illustrating deconvolution models to yield NMR signal for measurement of GlycA and GlycB according to embodiments of the present invention.
Figure 7C:
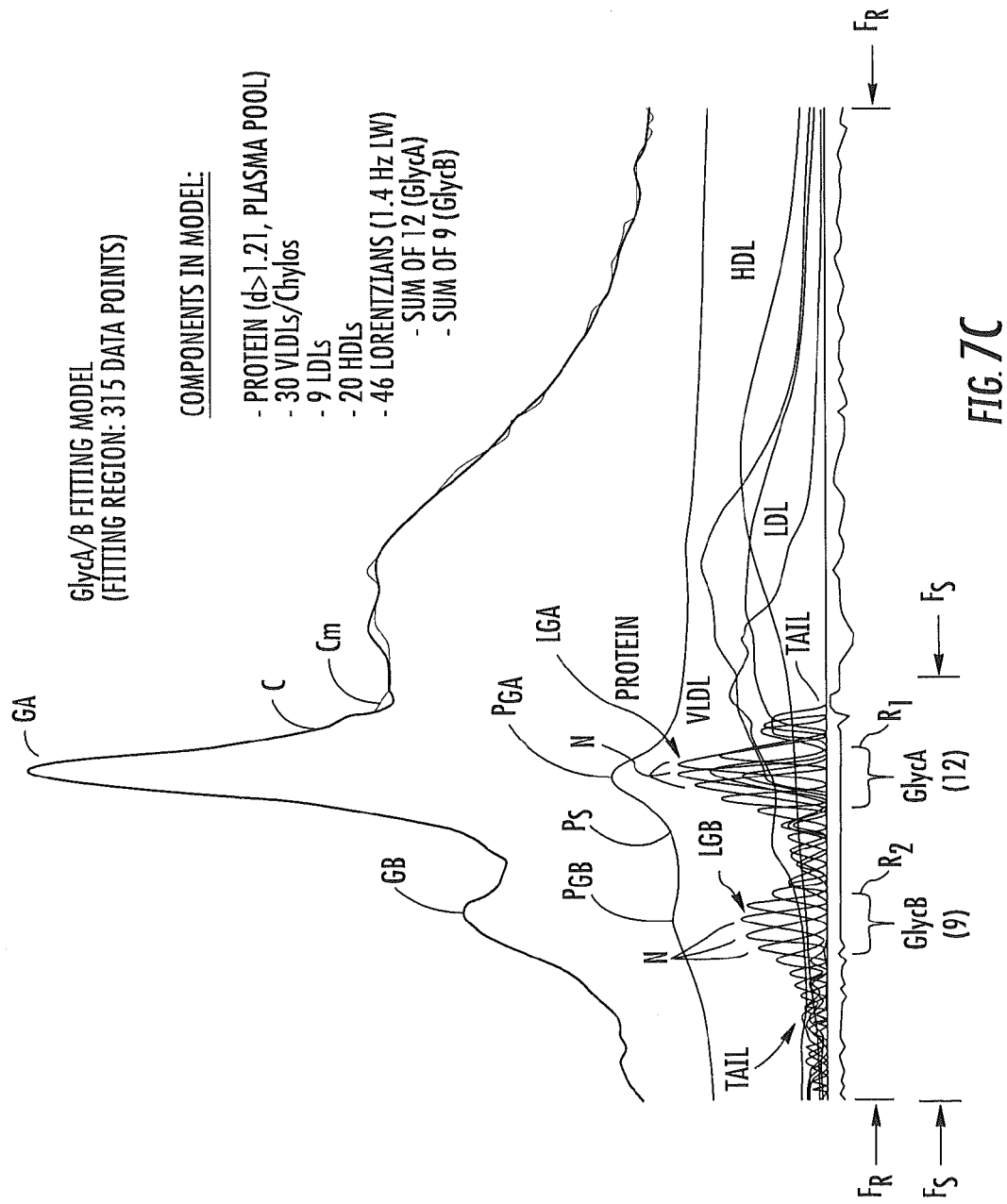

FIGS. 7B and 7C illustrate the composite (measured) signal "Cm" of the NMR spectra of FIG. 7A with a fitting region $F_R$ corresponding to the NMR spectrum between 2.080 and 1.845 ppm. The fitting region $F_R$ typically comprises 315 data points but more or less may be used, such as between about 200-400 data points, for example. The GlycA quantification/deconvolution model includes VLDL/chylos components, LDL components, and HDL components. Table 5 shows various TRLs that may be used in an exemplary DRI model.

TABLE 5

Characteristics of Triglyceride Rich Lipoprotein Subclasses Measured by NMR LipoProfile ® Analysis

| Subclass | TRL Subclass Components | NMR Chemical Shift (ppm) | Estimated Diameter (nm) |
|---|---|---|---|
| Chylomicrons | C-260 | 0.8477 | 260 |
| Chylomicrons | C-250 | 0.8470 | 250 |
| Chylomicrons | C-240 | 0.8464 | 240 |

TABLE 5-continued

Characteristics of Triglyceride Rich Lipoprotein Subclasses
Measured by NMR LipoProfile ® Analysis

| Subclass | TRL Subclass Components | NMR Chemical Shift (ppm) | Estimated Diameter (nm) |
|---|---|---|---|
| Chylomicrons | C-225 | 0.8457 | 225 |
| Chylomicrons | C-200 | 0.8443 | 200 |
| Chylomicrons | C-190 | 0.8440 | 190 |
| Chylomicrons | C-185 | 0.8436 | 185 |
| Chylomicrons | C-180 | 0.8429 | 180 |
| Chylomicrons | C-175 | 0.8422 | 175 |
| Chylomicrons | C-170 | 0.8416 | 170 |
| TRL V6 | V6-140 | 0.8402 | 140 |
| TRL V6 | V6-120 | 0.8388 | 120 |
| TRL V6 | V6-100 | 0.8374 | 100 |
| TRL V5 | V5-80 | 0.8361 | 80 |
| TRL V5 | V5-70 | 0.8347 | 70 |
| TRL V5 | V5-60 | 0.8333 | 60 |

The term "TRL V6" refers to TRL (triglyceride rich lipoprotein) particles or sub-fractions having a diameter between about 90 nm up to as much as about 170 nm, more typically having diameters between about 100-140 nm. The term "TRL V6" can also be defined with respect to the lipid methyl group NMR signal chemical shifts (ppm) corresponding to the estimated diameters as provided in Table I below.

The term "TRL V5" refers to large TRL particles having a diameter of between about 60 nm and about 80 nm (see Table 5 above for the associated NMR chemical shifts).

The terms "chylomicron" and "chylos" refer to very large TRL particles having diameters that are larger than TRL V6. As such chylomicrons reters to TRL particles or sub-fractions having a diameter between from about 170 nm up to about 260 nm (see Table 5 above for their associated NMR chemical shifts). There is not a clear demarcation between TRL V5 and TRL V6 nor between TRL V6 and chylomicrons, such that there is a distribution of particle sizes for each subgroup that overlaps in the range between about 80-90 nm for TRL V5-6 and between about 140-170 nm for TRL V6 & chylomicrons.

When the TRLs are quantified, the concentrations in particle concentration units (nmol/L) or triglyceride concentration units (mg/dL) can be expressed. Thus, for each of the different definitions of "large VLDL", either the particle concentrations or triglyceride concentrations could be used in the DRI model. Without wishing to be bound to any particular theory, based on linear regression analysis, the triglyceride concentration units may yield marginally better diabetes risk prediction.

Figure 7E:
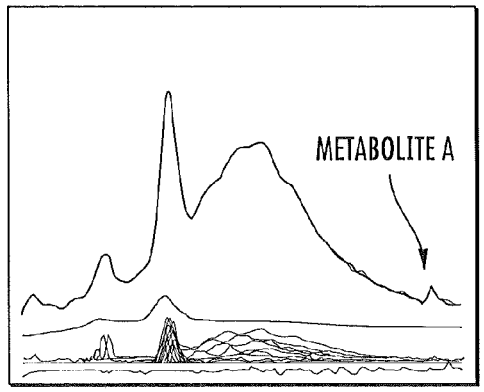
FIG. 7E is an NMR spectrum showing metabolite A present in a sample at typical normal (low) concentration according to embodiments of the present invention.
Figure 7F:
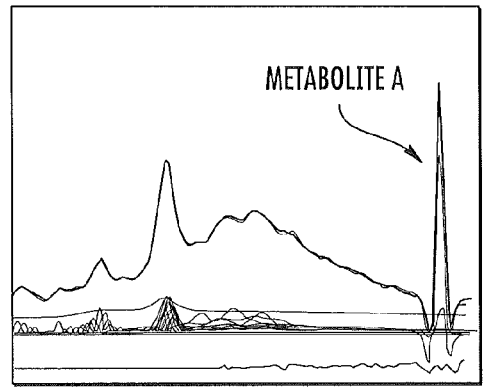
FIG. 7F is an NMR spectrum showing metabolite A present in a sample at an elevated (high) concentration according to embodiments of the present invention.
Figure 8A:
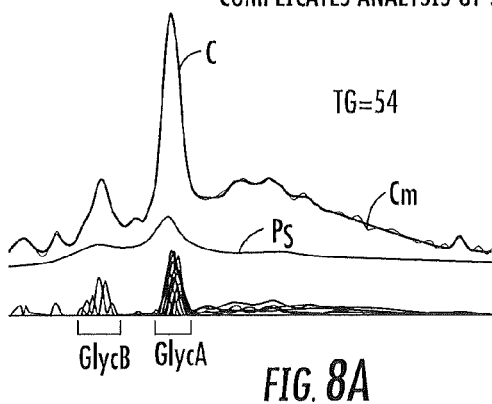
FIGS. 8A-8D are graphs of the GlycA NMR spectral region illustrating spectral overlap from lipoprotein signals (particularly from VLDL/Chylos) for samples with high TG (triglycerides).
Figure 8B:
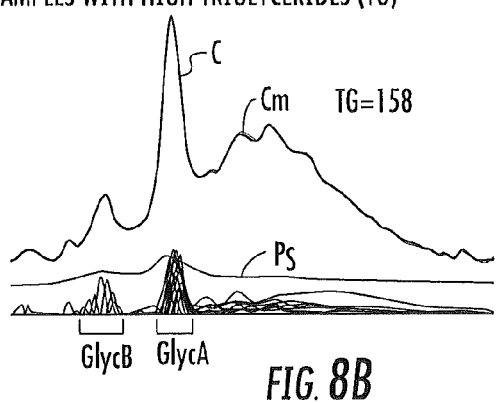
Figure 8C:
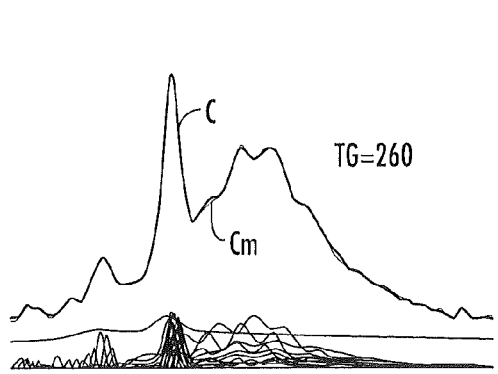
Figure 8D:
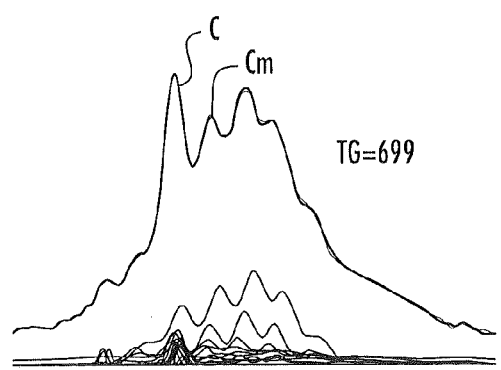

FIG. 7D is a table of different components in a GlycA/B deconvolution model according to embodiments of the present invention. Metabolite A is one component that can be measured in a GlycA/B deconvolution model and may be used clinically. As illustrated in FIGS. 7E and 7F, metabolite A can be present in a spectrum as a singlet peak and is typically present in a sample at low concentrations (FIG. 7E), but a high concentration of metabolite A may be present in a sample (FIG. 7F). A plurality of curve fitting functions for the metabolite A peak region can be used to quantitatively evaluate a level of metabolite A and/or to deconvolve the NMR spectrum for quantification of GlycA and/or GlycB, for example.

The deconvolving model components shown in FIG. 7D list a plurality of curve fit functions Glyc1-Glyc46 that can be applied to a fitting region that includes the GlycA peak region and extends to a GlycB peak region (typically with between about 40-50 curve fit functions, shown as with 46, but less or more such curve fit functions may be used, e.g., between 30-70). As will be discussed further below, the GlycA measurement can be carried out by summing values of a defined first subset of the curve fit functions, values associated with all or some of the Glyc1-Glyc26 components, for example. The GlycB measurement can be carried out by summing values of a second (typically smaller) defined subset of the curve fit functions, such as some or all components between Glyc27 and Glyc 46, for example.

FIGS. 8A-8D illustrate spectral overlaps from triglyceride rich lipoproteins as the TG (triglyceride) values increase which can be challenging to reliably deconvolve in a manner that provides precise and reliable GlycA and GlycB measurements.

The model provides sufficient HDL, LDL and VLDL/chylos components to be able to provide a good fit of the experimental signal as indicated by a close match between calculated signal C and experimental or measured composite signal Cm. Typically, the model will have more of the closely spaced VLDL/chylos components than either LDL or HDL components as these TRL contribute more signal to the left side of the spectrum. The model can include 20-50 VLDL/chylos components, typically about 25, 26, 27, 28, 29, 30, 31, 32, 33, 34, 35, 36, 37, 38, 39 or 40. In a preferred embodiment, the model includes 30 VLDL/chylos components.

The model can include a plurality "N" of (typically overlapping) curve fit components N that populate a sub-region Fs of the fitting region $F_R$ that extends from a few data points (e.g., about 10 or less) to the right of the GlycA measurement region $R_1$ (e.g., starting at about 1.9 ppm or higher) to at least a few data points to the left of the GlycB region $R_2$ (and can extend to the end of the fitting region $F_R$ to 2.080 ppm), at least where GlycB is measured or evaluated. Each component N, in this embodiment, can be a Lorentzian-shaped signal with a line width about 1.4 Hz. Also, in particular embodiments, each data point can be about 0.275 Hz apart as determined by the digital resolution of the spectrum. The tail portion of the region Fs on the left side may include more (Lorentzian) components than the tail portion on the right side. The number of components N in the region Fs n can be about 46 (e.g., about 46 Lorentzians) but more or less components "N" can be used. For example, the region Fs can include, but is not limited to, between 30-70 Lorentzians, or n=30, 35, 36. 37, 38, 39, 40, 41, 42, 43, 44, 45, 46, 47, 48, 49, 50, 51, 52, 53, 54, 55, 56, 57, 58, 59, or 60. The curves N are typically Lorentzian functions with line widths at half-height of between 2-10 data points (0.55-2.75 Hz at 400 MHz), more typically between 4-6 data points, and are offset from each other by a defined amount, such as, for example, 2 data points (0.55 Hz).

The GlycA and GlycB Lorentzians (or other curve fitting components N) can have the same or different numbers of data points. The GlycB Lorentzians N can have the same, less or more data points than the GlycA Lorentzians N. The Lorentzian fit components "N" can have peak line widths (LW) of about 1.4 Hz (at half height). However, other LWs can be used including, but not limited to, 1.1, 1.2, 1.3, 1.5 and the like. To be clear, data for GlycB can be omitted from the evaluation for the DRI risk index.

GlycA can be calculated using a defined subset of the number of curve fit components N that fill the entire region $R_1$. GlycB can be calculated using a suitable number of curve fit (e.g., Lorentzian fit) components N that fill the entire region $R_2$. The region $R_1$ can be between 5-6 Hz. The GlycB region $R_2$ can be 7-8 Hz. Optionally, the GlycA components N can be offset by 2 data points. The GlycB components N can be offset by 4 data points.

GlycA can be calculated using a sum of adjacent Lorentzian components N, typically between 9-15, such as 9, 10, 11, 12, 13, 14 and 15 components. GlycB can be the sum of adjacent Lorentzian fit components N, with the same, more, or less, typically less, than that used for GlycA measurements, such as between about 5-10 components N, typically about 7, about 8 or about 9 components. The Lorentzians between $R_1$ and $R_2$ are not included in the quantified measurement of either GlycA or GlycB. FIG. 7B illustrates the sum of 7 adjacent Lorentzians used to calculate the GlycB measurement and the sum of 10 (more narrow) Lorentzians can be used to calculate the GlycA measurements. FIG. 7C illustrates the sum of 9 adjacent Lorentzians used to calculate the GlycB measurement and the sum of 12 (more closely spaced) Lorentzians can be used to calculate the GlycA measurements.

The number of HDL, LDL and VLDL components may vary for the GlycA calculation. As shown, the HDL components can be 20 HDL components (spanning the range of HDL subclass diameters), but more or less can be used, e.g., between about 10-26. As shown, the number of LDL components is 9 components (representing different LDL diameters), but more or less can be used, e.g., between about 5-20. As shown, the number of VLDLs/Chylos components is 30, but more or less can be used, e.g., 25-60 of different size ranges.

To be clear, while a preferred embodiment describes the curve fit components as Lorentzian fit components, other fitting components may be used including, but not limited to, experimental N-acetyl methyl group signals or Gaussian lineshape functions. Thus, any suitable curve fit function can be used.

FIG. 9A is a Table of different protein components (Protein 1, Protein 2 and Protein 3) that, when used in the Glyc deconvolution model, yields different GlycA concentrations and different GlycA associations with CHD events and All-Cause Death in MESA. FIGS. 9B, 9C and 9D illustrate the respective protein signal Ps in the deconvolved spectrum and the differences they exhibit in the amplitudes of the signals in the GlycA and GlycB peak regions. To optimize the calculated GlycA and/or GlycB measurement, in some embodiments, the deconvolution model includes a defined protein signal component as discussed above. This protein signal component Ps is for protein other than lipoproteins, e.g., other than HDL, LDL, VLDL/chylos, e.g., and may be associated with the >1.21 g/L density fraction of plasma obtained by ultracentrifugation (which includes albumin and other non-lipoprotein proteins in plasma).

This signal component "Ps" is shown in FIGS. 7A-7C. Surprisingly, although this protein signal Ps does include a peak ($P_{GA}$, $P_{GB}$, respectively) aligned with the peak at the chemical shift for both GlycA and GlycB, eliminating this portion of the protein NMR signal from the deconvolution model (by, for example, digital manipulation or signal processing) was found to make the calculated GlycA and GlycB measurements relatively less clinically informative (weaker disease associations). At the other extreme, including in the deconvolution model a protein component with a relatively large signal at the GlycA and GlycB positions results in lower GlycA and GlycB concentrations that are also less clinically informative, as shown for Protein #2 and Protein #3 in FIGS. 9C and 9D. Thus, by selecting an appropriate protein component with an intermediate signal amplitude at the GlycA and GlycB positions, such as Protein #1 in FIG. 9B, the deconvolution model may be "tuned" to produce GlycA and GlycB concentrations that are improved and/or optimized with respect to their clinical associations with inflammation and related disease states.

Thus, in some embodiments, it is contemplated that the GlycA measurement will provide a better clinical indicator if it does not include the lipoprotein signal (accounted for in the deconvolution model with the VLDL/chylo, LDL and HDL components) and if it includes only a portion of the remaining NMR signal, e.g., it does not include all other NMR protein signal at the GlycA peak region. This subset of the NMR signal at the GlycA peak region may be more reflective of inflammatory protein activity, e.g., N-acetyl methyl signals from glycosylated acute phase proteins.

FIG. 10 is a screen shot of the deconvolution of a 10 mmol/L reference standard sample of N-acetylglucosamine, from which a conversion factor of 17.8 was determined to transform signal area concentrations of GlycA and GlycB to µmol/L glycoprotein N-acetyl methyl group concentrations. In some embodiments, according to MESA subjects, first to fourth quartile (mean) levels of GlycA can be: Q1: 21.6*17.8, Q2: 25.8*17.8, Q3: 29.3*17.8 and Q4: 35.3*17.8.

GlycA measurement precision using the model shown in FIG. 7B was shown to be good. A within-run (5 pools from 2009) analysis of lowest GlycA=40.5 (CV=2.47%) and highest GlycA=58.4 (CV=1.6%). Within-lab results from 13 pools from 2010 and 2011 had a lowest GlycA=25.6 (CV=4.08%) and highest GlycA=69.1 (CV=1.87%). These concentrations are expressed as "arbitrary units" of NMR signal areas and can be multiplied by 17.8 to convert them to µmol/L N-acetyl methyl group concentrations.

It is believed that the measured amplitude of the GlycA signal in any one sample may have the advantage of providing a more stable and "time-integrated" measure of the patient's inflammation state than is provided by measurements of hs-CRP or other individual inflammatory proteins.

As noted above, FIG. 10 illustrates a conversion factor that can be used to calculate measurements of GlycA. The GlycA measurement can also be a unit less parameter as assessed by NMR by calculating an area under a peak region at a defined peak in NMR spectra. In any event, measures of GlycA with respect to a known population (such as MESA) can be used to define the level or risk for certain subgroups, e.g., those having values within the upper half of a defined range, including values in the third and fourth quartiles, or the upper 3-5 quintiles and the like.

Figure 12A:
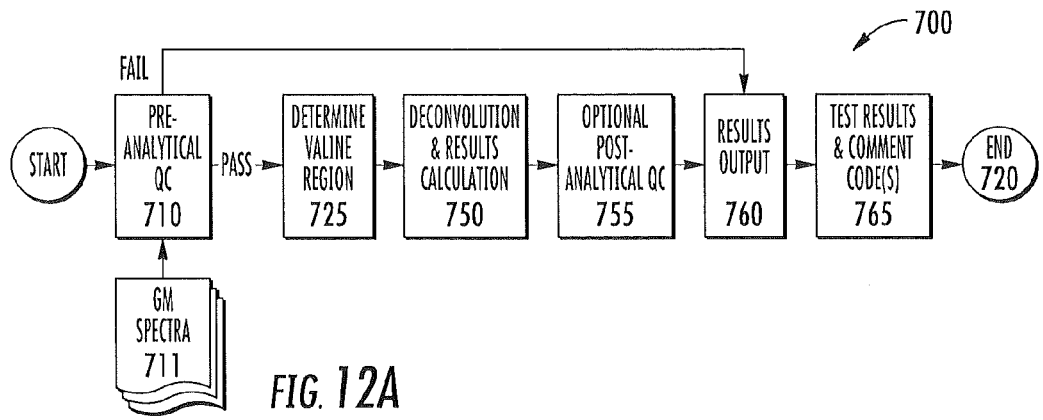
FIG. 12A is a flow diagram of an NMR valine test protocol according to embodiments of the present invention.
Figure 12B:
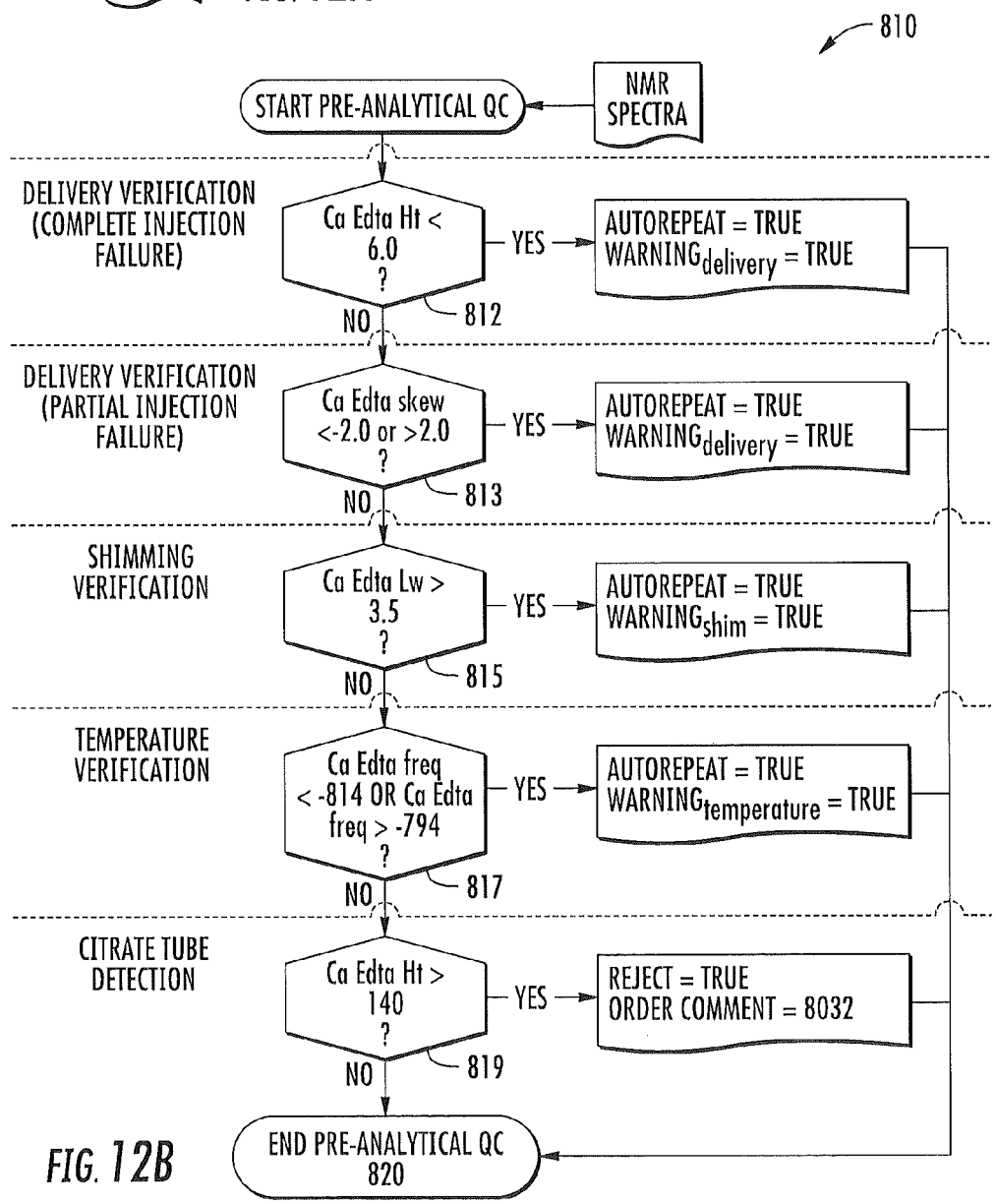
FIG. 12B is a flow chart of exemplary pre-analytical processing that can be used prior to obtaining NMR signal of biosamples according to embodiments of the present invention.
Figure 12C:
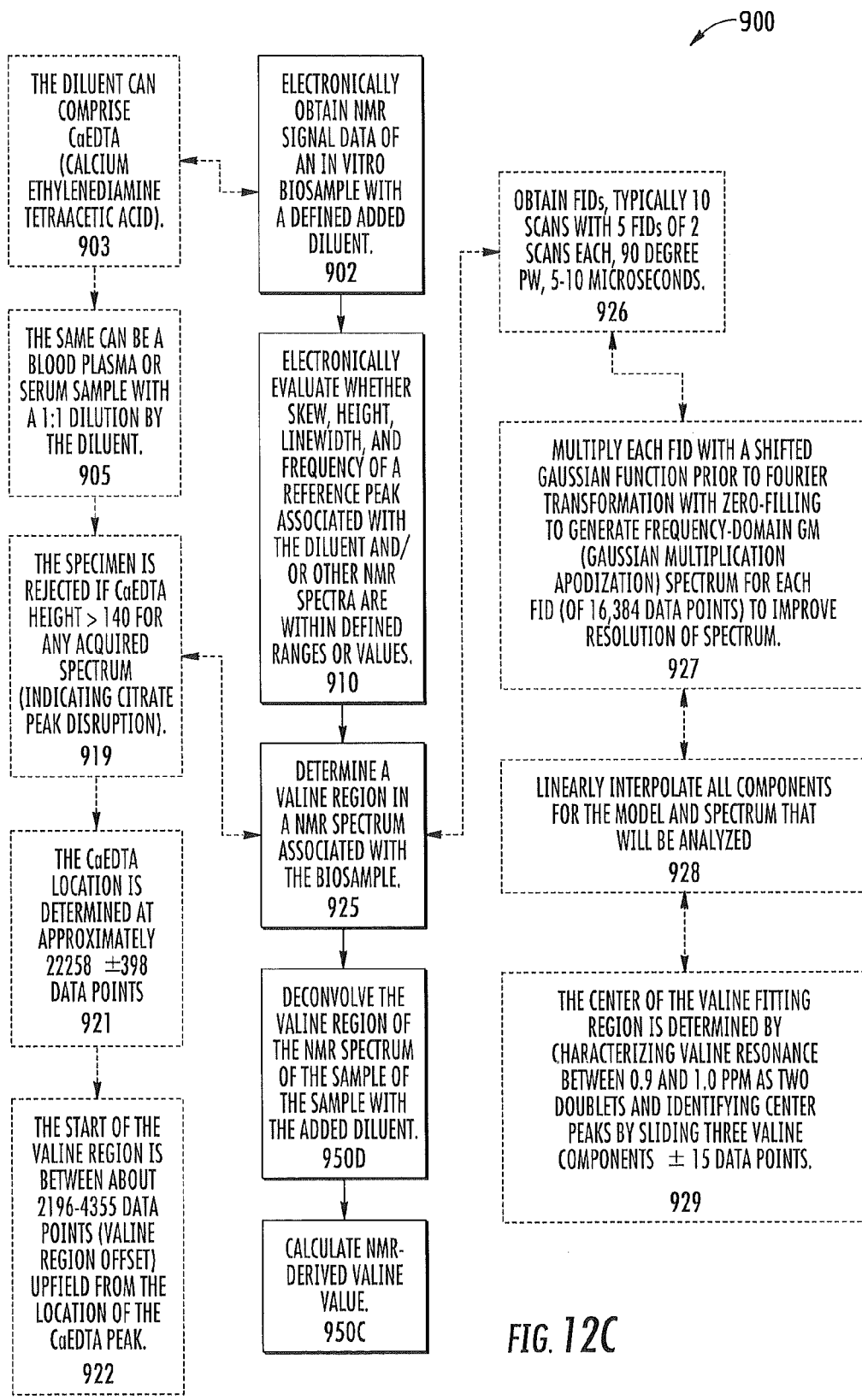
FIG. 12C is a flow diagram of operations that can be used to evaluate valine using NMR according to embodiments of the present invention.

FIGS. 12A-12C are exemplary flow diagrams of operations that can be used to obtain NMR signal associated with valine according to embodiments of the present invention.

FIG. 12A illustrates that a pre-analytical evaluation (block 710) can occur before a valine region of the NMR signal is determined (block 725), then deconvolved (block 750). FIG. 12B illustrates an exemplary pre-analytical evaluation 810 which includes delivery verification of the sample into the flow cell as either complete failure (block 812) or partial injection failure (block 813), shimming verification (block 815), temperature verification (block 817) and a citrate tube detection (failure) (block 819), all using defined characteristics of signal associated with a defined diluent added to the sample.

Referring again to FIG. 12A, once the defined parameters are confirmed within limits, the pre-analytical quality control analysis can end (block 720) and the determination of the valine region can be identified (block 725) and the spectrum deconvolved and valine level calculated (block 750). Optionally, a post-analytical quality control can be electronically performed (block 755) and the results output (block 760). The results can be included in a test report with comments, visual indicia of high or low and the like (block 765).

Referring to FIG. 12C, NMR signal can be electronically obtained of an in vitro biosample with a defined added diluent (block 902). The QC evaluation can be carried out (block 910). The valine region is determined (block 925). The valine region is deconvolved (block 950d) and an NMR derived value of valine is calculated (950c).

The diluents can comprise calcium ethylenediamine tetraacetic acid (Ca EDta) (block 903) or other suitable diluent that creates a reliable peak and behaves in a predictable manner. Well established chemical shift or quantitation references include, for example, formate, trimethylsilylpropionate (and isotopically labeled isomers), and EDTA.

The pre-analytical quality control evaluation 810 can be based on inspection of characteristics of the CaEDTA reference peak and the system or processor can be configured not to perform the Valine test unless the NMR spectra have been acquired under specified conditions such as those shown in FIG. 12B. The sample temperature can be 47±0.5° C. in the flow cell for NMR scans/signal acquisition. The sample can comprise diluents in a 1:1 ratio (block 905) or other defined ratio (e.g., more sample, less diluents or more diluent; less sample, e.g., 2:1 or more sample, less diluents, e.g. 1:2).

The test sample can be rejected with a defined error code if CaEDTA height>140 for any acquired spectrum (block 919). This high value is indicative of detection of the citrate peak in conjunction with the CaEDTA peak. The citrate peak is introduced by collection of the specimen in an improper citrate tube. By disrupting the ability to locate the exact position of the CaEDTA peak, the citrate peak can disrupt the process for determining the Valine region.

The Valine region is located upfield relative to the position of the CaEDTA peak. The broad peaks beneath Valine are various methyl (—$CH_3$—) protons of lipoproteins. The CaEDTA location can be determined at approximately 22258±398 data points (block 921). The Valine region can be determined independently for each acquired spectrum. The Valine signal can be modeled with suitable data points using, for example, 25 data points (center±12 data points) for each peak of the quartet or 300 data points for the valine region of both doublets, but other numbers of data points may be used. The measurement of Valine can be carried out using one, two, three or all four peaks of the valine peak quartet.

All basis set spectra can be linearly interpolated before utilized by the non-negative least squares algorithm. The spectra to be analyzed and the basis set spectra can have a zero baseline offset modification before utilized by the non-negative least squares algorithm.

The start of the Valine region can be at about 2196-4355 data points, typically the latter when including both doublets, (the "Valine region offset") upfield from the location of the CaEDTA peak (block 922). In some embodiments, the start of the valine region is at 4355 data points upfield from the location of the CaEDTA peak.

In some embodiments, the valine quantification is carried out by characterizing the valine resonances at between 0.0-1.01 ppm as two doublets. Three or more valine experimental spectra stepped by two data points can be used as basis sets to model valine signal. The center valine peaks can be located by sliding three valine components+/−15 data points and determined through a least squares sum minimization. The valine signal can be modeled with a total of about 300 data points.

Each basis set, including those used for the baseline but excluding the DC offset, are offset such that the lowest value is subtracted from the function (making the lowest point equal to 0). This prevents inclusion of a DC offset in the shapes they represent.

The Valine region from each acquired spectrum is deconvolved with a series of analyte and baseline functions which have been treated to the same type of pre-processing as the acquired spectra. The deconvolution coefficient for each component can be multiplied by an associated conversion factor. The current Valine embodiment has a conversion factor of 2271 to report Valine in µM units; however, this value can vary by ±10% without unduly affecting the reported value significantly.

| Component Name | Filename | Conversion Factor | Basis Function Starting position relative to CaEDTA |
|---|---|---|---|
| Valine1 | Valine318LB019.1r | 2271 | −4353 |
| Valine2 | Valine318LB019.1r | 2271 | −4355 |
| Valine3 | Valine318LB019.1r | 2271 | −4357 |

The resulting values are summed. Result values produced independently for each acquired spectrum can be averaged to generate final values to use in the measurement.

Data can be acquired using presaturation water suppression from a 1:1 diluted sample and can include between 5-20 scans, typically about 10 scans stored as 5 blocks of 2 (5 FIDs consisting of 2 scans each) (block 926).

The pulse sequence used in conjunction with presaturation water suppression can optionally include a presaturation (water suppression) pulse and a suitable excitation pulse. FIDs can be acquired with 9024 data points with a sweep width of 4496.4 Hz.

Each FID can be multiplied with a shifted Gaussian function:

$$e^{-\left(\frac{(t-gfs)}{gf}\right)^2},$$

or in computer terms, exp(−((t−gfs)/gf)^2), where gfs=0.2 seconds and gf=0.2 seconds.

This can be performed prior to Fourier transformation with zero-filling which yields the frequency-domain GM spectrum for each FID consisting of 16,384 data points (block 927). The spectra can be phased using the calibration-specified phase value. The spectra can be scaled (multiplied) by a calibration-specified scaling factor. All basis set spectra can be linearly interpolated before utilized by the non-negative least squares algorithm. The spectra to be analyzed and the basis set spectra can have a zero baseline offset modification before utilized by the non-negative least squares algorithm (e.g., all components used for the model and the spectrum that will be analyzed can be linearly interpolated) (block 928). To determine the center of the valine fitting region, the valine resonances between 0.9 and 1.0 as two doublets can be characterized and the center peaks can be identified by sliding three valine components±15 data points (block 929).

FIG. 13 is a chart of prospective associations of hs-CRP and NMR measured GlycA and Valine levels with various exemplary disease outcomes based on MESA data (n≈5680). The chart was generated from logistic regression analyses adjusted for age, gender, race, smoking, systolic blood pressure, hypertension medications, body mass index, diabetes, LDL-P and HDL-P. The likelihood ratio statistic $\chi 2$ gives a quantitative measure of the extent to which the indicated variable improves disease prediction when added to the 10 covariates in the regression model. The analyses used GlycA measurement values from the deconvolution model shown in FIG. 7B. The right side column shows that GlycA and Valine are additive in their associations with disease when they both have significant associations examined separately.

FIG. 14 is a Table of Characteristics of MESA subjects by NMR measured GlycA quartile. The mean GlycA level of those in the 3rd quartile is 29.3. This table shows that people with higher GlycA levels have characteristics associated with higher inflammation (more smoking, hypertension, hs-CRP, etc). NMR signal area units can be called "arbitrary" units. The GlycA levels in this table are in these "arbitrary units" that may be converted to methyl group concentration units (umol/L) by multiplying by 17.8.

Figure 15:
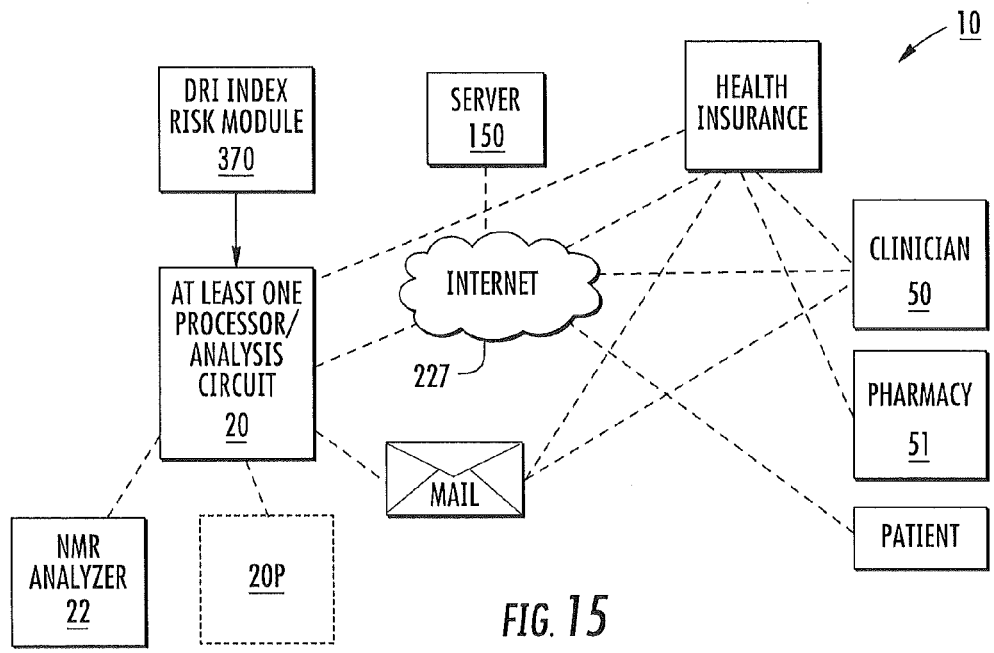
FIG. 15 is a schematic illustration of a system for analyzing a patient's predictable risk using a DRI risk index module and/or circuit using according to embodiments of the present invention.

Referring now to FIG. 15, it is contemplated that most, if not all, the measurements can be carried out on or using a system 10 in communication with or at least partially onboard an NMR clinical analyzer 22 as described, for example, with respect to FIG. 16 below and/or in U.S. Pat. No. 8,013,602, the contents of which are hereby incorporated by reference as if recited in full herein.

The system 10 can include a Diabetes Risk Index Module 370 to collect data suitable for determining the DRI (e.g., GlycA, valine). The system 10 can include an analysis circuit 20 that includes at least one processor 20p that can be onboard the analyzer 22 or at least partially remote from the analyzer 22. If the latter, the Module 370 and/or circuit 20 can reside totally or partially on a server 150. The server 150 can be provided using cloud computing which includes the provision of computational resources on demand via a computer network. The resources can be embodied as various infrastructure services (e.g. computer, storage, etc.) as well as applications, databases, file services, email, etc. In the traditional model of computing, both data and software are typically fully contained on the user's computer; in cloud computing, the user's computer may contain little software or data (perhaps an operating system and/or web browser), and may serve as little more than a display terminal for processes occurring on a network of external computers. A cloud computing service (or an aggregation of multiple cloud resources) may be generally referred to as the "Cloud". Cloud storage may include a model of networked computer data storage where data is stored on multiple virtual servers, rather than being hosted on one or more dedicated servers. Data transfer can be encrypted and can be done via the Internet using any appropriate firewalls to comply with industry or regulatory standards such as HIPAA. The term "HIPAA" refers to the United States laws defined by the Health Insurance Portability and Accountability Act. The patient data can include an accession number or identifier, gender, age and test data.

The results of the analysis can be transmitted via a computer network, such as the Internet, via email or the like to a patient, clinician site 50, to a health insurance agency 52 or a pharmacy 51. The results can be sent directly from the analysis site or may be sent indirectly. The results may be printed out and sent via conventional mail. This information can also be transmitted to pharmacies and/or medical insurance companies, or even patients that monitor for prescriptions or drug use that may result in an increase risk of an adverse event or to place a medical alert to prevent prescription of a contradicted pharmaceutical agent. The results can be sent to a patient via email to a "home" computer or to a pervasive computing device such as a smart phone or notepad and the like. The results can be as an email attachment of the overall report or as a text message alert, for example.

Figure 16:
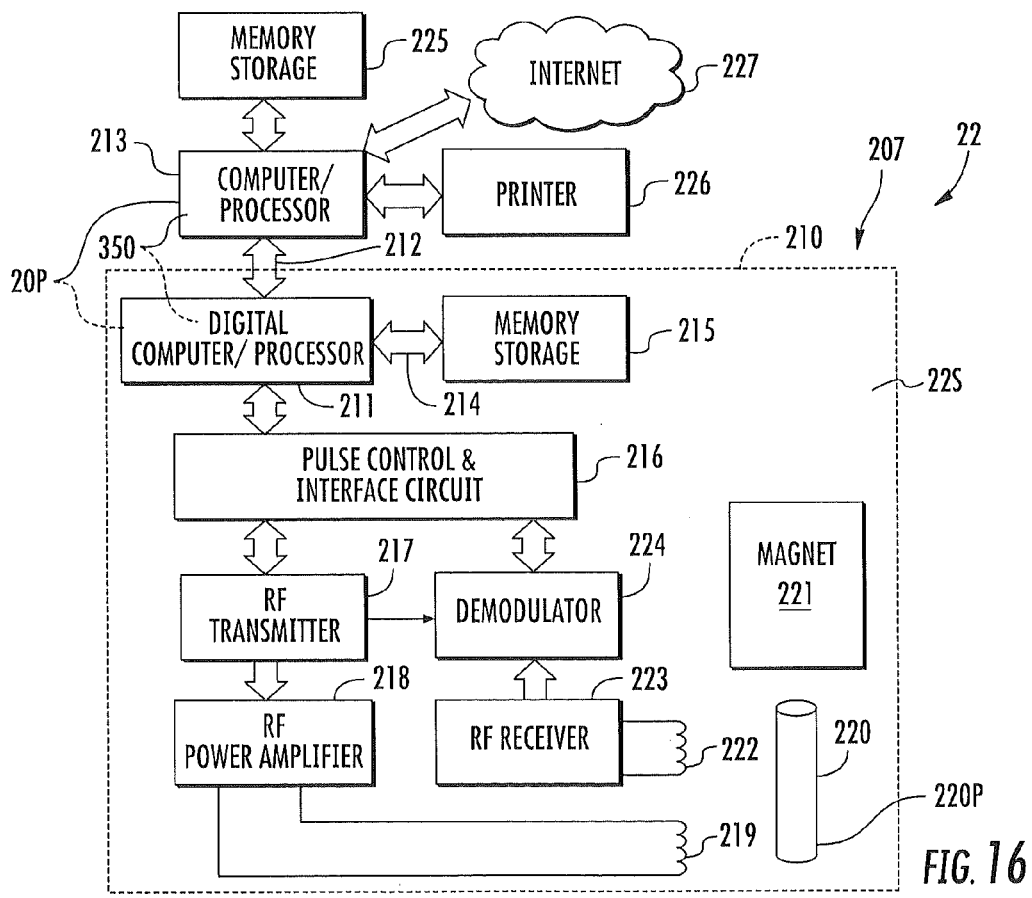
FIG. 16 is a schematic illustration of a NMR spectroscopy apparatus according to embodiments of the present invention.

Referring now to FIG. 16, a system 207 for acquiring at least one NMR spectrum for a respective biosample is illustrated. The system 207 includes an NMR spectrometer 22s and/or analyzer 22 for obtaining NMR data for NMR measurements of a sample. In one embodiment, the spectrometer 22s is configured so that the NMR signal acquisition is conducted at about 400 MHz for proton signals; in other embodiments the measurements may be carried out at between about 200 MHz to about 900 MHz or other suitable frequency. Other frequencies corresponding to a desired operational magnetic field strength may also be employed. Typically, a proton flow probe is installed, as is a temperature controller to maintain the sample temperature at 47+/−0.5 degrees C. The spectrometer 22 is controlled by a digital computer 214 or other signal processing unit. The computer 211 should be capable of performing rapid Fourier transformations. It may also include a data link 212 to another processor or computer 213, and a direct-memory-access channel 214 which can connects to a hard memory storage unit 215 and/or remote server 150 (FIG. 15).

The digital computer 211 may also include a set of analog-to-digital converters, digital-to-analog converters and slow device I/O ports which connect through a pulse control and interface circuit 216 to the operating elements of the spectrometer. These elements include an RF transmitter 217 which produces an RF excitation pulse of the duration, frequency and magnitude directed by the digital computer 211, and an RF power amplifier 218 which amplifies the pulse and couples it to the RF transmit coil 219 that surrounds sample cell 220 and/or flow probe 220p. The NMR signal produced by the excited sample in the presence of a 9.4 Tesla polarizing magnetic field produced by superconducting magnet 221 is received by a coil 222 and applied to an RF receiver 223. The amplified and filtered NMR signal is demodulated at 224 and the resulting quadrature signals are applied to the interface circuit 216 where they are digitized and input through the digital computer 211. The DRI risk evaluation Module 370 or analysis circuit 20 (FIGS. 15, 17) or module 350 (FIG. 16) or can be located in one or more processors associated with the digital computer 211 and/or in a secondary computer 213 or other computers that may be on-site or remote, accessible via a worldwide network such as the Internet 227.

After the NMR data are acquired from the sample in the measurement cell 220, processing by the computer 211 produces another file that can, as desired, be stored in the storage 215. This second file is a digital representation of the chemical shift spectrum and it is subsequently read out to the computer 213 for storage in its storage 225 or a database associated with one or more servers. Under the direction of a program stored in its memory, the computer 213, which may be a personal, laptop, desktop, workstation, notepad, tablet or other computer, processes the chemical shift spectrum in accordance with the teachings of the present invention to generate a report which may be output to a printer 226 or electronically stored and relayed to a desired email address or URL. Those skilled in this art will recognize that other output devices, such as a computer display screen, notepad, smart phone and the like, may also be employed for the display of results.

It should be apparent to those skilled in the art that the functions performed by the computer 213 and its separate storage 225 may also be incorporated into the functions performed by the spectrometer's digital computer 211. In such case, the printer 226 may be connected directly to the digital computer 211. Other interfaces and output devices may also be employed, as are well-known to those skilled in this art.

Embodiments of the present invention may take the form of an entirely software embodiment or an embodiment combining software and hardware aspects, all generally referred to herein as a "circuit" or "module."

As will be appreciated by one of skill in the art, the present invention may be embodied as an apparatus, a method, data or signal processing system, or computer program product.

Accordingly, the present invention may take the form of an entirely software embodiment, or an embodiment combining software and hardware aspects. Furthermore, certain embodiments of the present invention may take the form of a computer program product on a computer-usable storage medium having computer-usable program code means embodied in the medium. Any suitable computer readable medium may be utilized including hard disks, CD-ROMs, optical storage devices, or magnetic storage devices.

The computer-usable or computer-readable medium may be, but is not limited to, an electronic, magnetic, optical, electromagnetic, infrared, or semiconductor system, apparatus, device, or propagation medium. More specific examples (a non-exhaustive list) of the computer-readable medium would include the following: an electrical connection having one or more wires, a portable computer diskette, a random access memory (RAM), a read-only memory (ROM), an erasable programmable read-only memory (EPROM or Flash memory), an optical fiber, and a portable compact disc read-only memory (CD-ROM). Note that the computer-usable or computer-readable medium could even be paper or another suitable medium, upon which the program is printed, as the program can be electronically captured, via, for instance, optical scanning of the paper or other medium, then compiled, interpreted or otherwise processed in a suitable manner if necessary, and then stored in a computer memory.

Computer program code for carrying out operations of the present invention may be written in an object oriented programming language such as Java7, Smalltalk, Python, Labview, C++, or VisualBasic. However, the computer program code for carrying out operations of the present invention may also be written in conventional procedural programming languages, such as the "C" programming language or even assembly language. The program code may execute entirely on the user's computer, partly on the user's computer, as a stand-alone software package, partly on the user's computer and partly on a remote computer or entirely on the remote computer. In the latter scenario, the remote computer may be connected to the user's computer through a local area network (LAN) or a wide area network (WAN) or secured area network (SAN), or the connection may be made to an external computer (for example, through the Internet using an Internet Service Provider).

The flowcharts and block diagrams of certain of the figures herein illustrate the architecture, functionality, and operation of possible implementations of analysis models and evaluation systems and/or programs according to the present invention. In this regard, each block in the flow charts or block diagrams represents a module, segment, operation, or portion of code, which comprises one or more executable instructions for implementing the specified logical function(s). It should also be noted that in some alternative implementations, the functions noted in the blocks might occur out of the order noted in the figures. For example, two blocks shown in succession may in fact be executed substantially concurrently or the blocks may sometimes be executed in the reverse order, depending upon the functionality involved.

Figure 17:
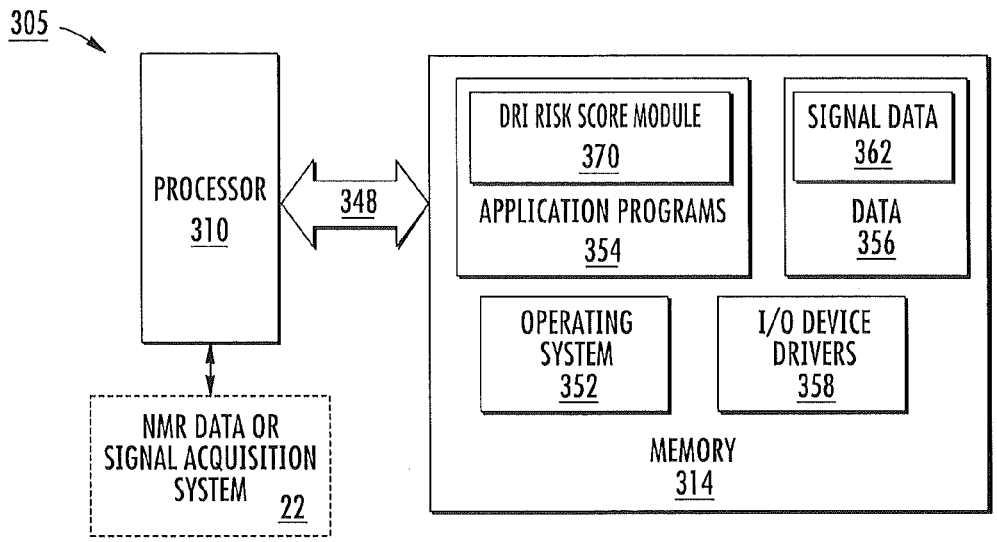
FIG. 17 is a schematic diagram of a data processing system according to embodiments of the present invention.

FIG. 17 is a block diagram of exemplary embodiments of data processing systems 305 that illustrates systems, methods, and computer program products in accordance with embodiments of the present invention. The processor 310 communicates with the memory 314 via an address/data bus 348. The processor 310 can be any commercially available or custom microprocessor. The memory 314 is representative of the overall hierarchy of memory devices containing the software and data used to implement the functionality of the data processing system 305. The memory 314 can include, but is not limited to, the following types of devices: cache, ROM, PROM, EPROM, EEPROM, flash memory, SRAM, and DRAM.

As shown in FIG. 17, the memory 314 may include several categories of software and data used in the data processing system 305: the operating system 352; the application programs 354; the input/output (I/O) device drivers 358; a DRI module 370 and the data 356. The Diabetes Risk Index Evaluation Module 370 can consider the level of the measured GlycA, lipoprotein components and optionally also valine and also optionally, glucose, in a multi-parameter mathematical model of risk of developing type 2 diabetes in the next 5-7 years or a likelihood of having prediabetes.

The data 356 may include signal (constituent and/or composite spectrum lineshape) data 362 which may be obtained from a data or signal acquisition system 320. As will be appreciated by those of skill in the art, the operating system 352 may be any operating system suitable for use with a data processing system, such as OS/2, AIX or OS/390 from International Business Machines Corporation, Armonk, N.Y., WindowsCE, WindowsNT, Windows95, Windows98, Windows2000 or WindowsXP from Microsoft Corporation, Redmond, Wash., PalmOS from Palm, Inc., MacOS from Apple Computer, UNIX, FreeBSD, or Linux, proprietary operating systems or dedicated operating systems, for example, for embedded data processing systems.

The I/O device drivers 358 typically include software routines accessed through the operating system 352 by the application programs 354 to communicate with devices such as I/O data port(s), data storage 356 and certain memory 314 components and/or the NMR spectrometer or analyzer 22. The application programs 354 are illustrative of the programs that implement the various features of the data processing system 305 and can include at least one application, which supports operations according to embodiments of the present invention. Finally, the data 356 represents the static and dynamic data used by the application programs 354, the operating system 352, the I/O device drivers 358, and other software programs that may reside in the memory 314.

While the present invention is illustrated, for example, with reference to the Modules 350, 370 being an application program in FIG. 17, as will be appreciated by those of skill in the art, other configurations may also be utilized while still benefiting from the teachings of the present invention. For example, the GlycA Module 350 and/or the DRI Module 370 may also be incorporated into the operating system 352, the I/O device drivers 358 or other such logical division of the data processing system 305. Thus, the present invention should not be construed as limited to the configuration of FIG. 17, which is intended to encompass any configuration capable of carrying out the operations described herein.

Figure 18:
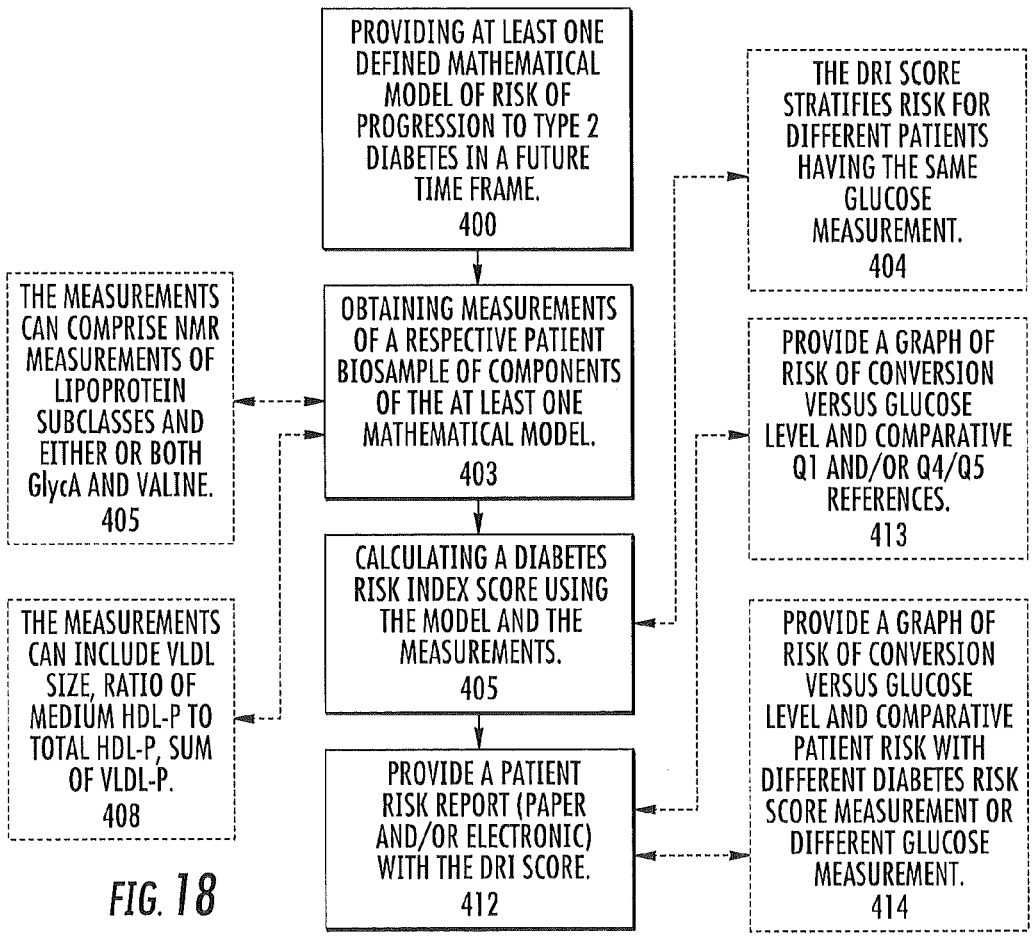
FIG. 18 is a flow chart of exemplary operations that can be used to assess risk of developing T2DM according to embodiments of the present invention.

FIG. 18 is a flow chart of exemplary operations that can carry out embodiments of the present invention. As shown, at least one defined mathematical model or risk of progression to type 2 diabetes in a future time frame (e.g., 5-7 years) can be provided (block 400). Measurements of components of the at least one mathematical model of a respective patient biosample can be obtained (block 403). A diabetes risk index score can be calculated using the model and the measurements (block 405). A patient risk report (paper and/or electronic) with the DRI score can be provided to desired recipients (e.g., a patient and/or clinician) (block 412). The DRI score can stratify risk for different patients having the same glucose measurement (block 404).

The measurements can include NMR measurements of lipoprotein subclasses and either or both GlycA and valine (block 405). The measurements can include one or more of VLDL size, ratio of medium HDL-P to total HDL-P and/or sum of VLDL-P (block 408).

A graph of risk of conversion versus glucose level and comparative Q1 and/or Q4/Q5 references can be provided as a relative risk summary (block 413).

A graph of risk of conversion versus glucose level and comparative patient risk with different diabetes risk score measurement and/or different glucose measurement can be provided (block 414).

The risk summary can provide a relative comparison to defined population norms.

Figure 19:
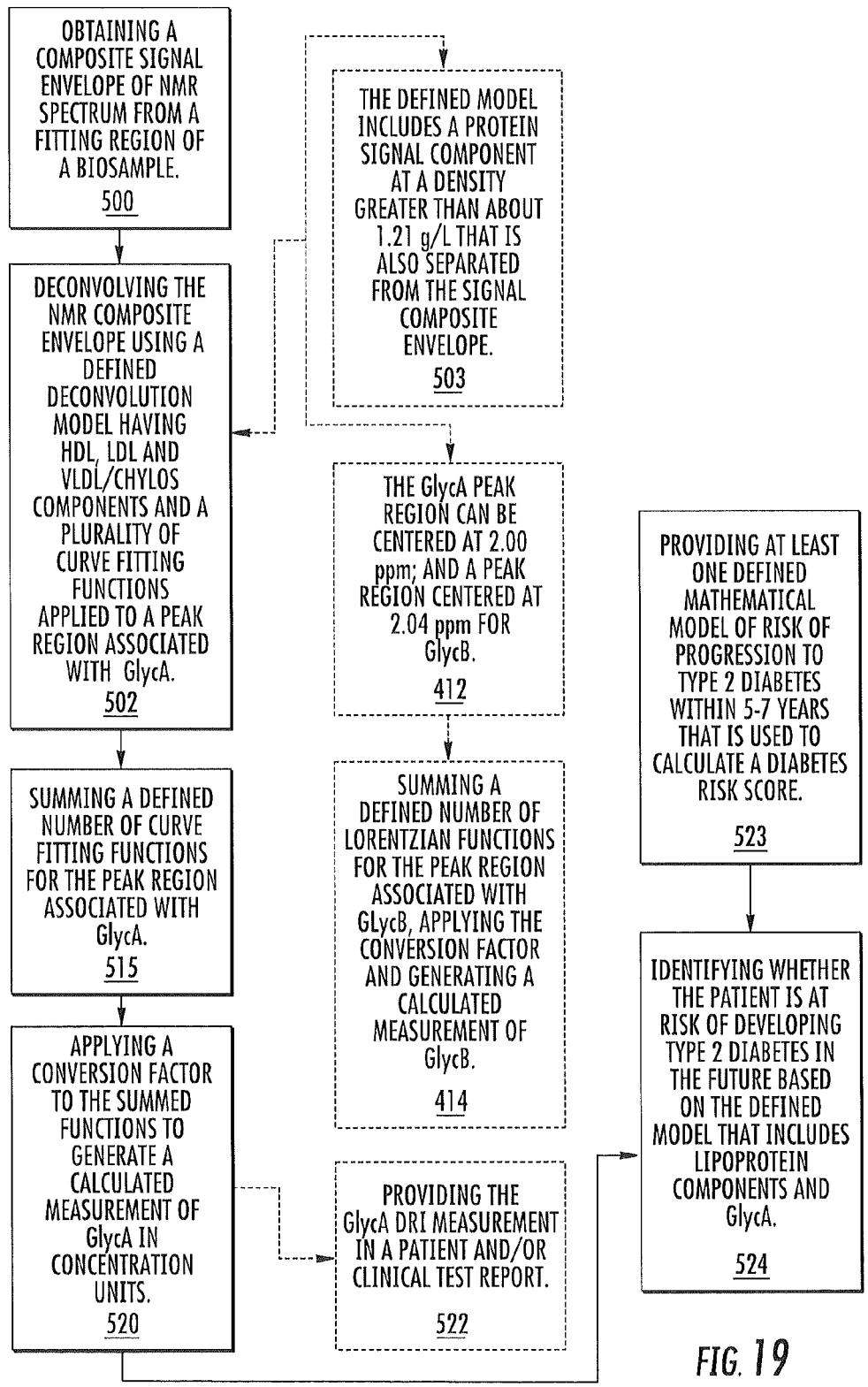
FIG. 19 is a flow chart of exemplary operations that can be used to assess a risk of developing T2DM in the future and/or having prediabetes, according to embodiments of the present invention.

FIG. 19 is a flow chart of exemplary operations that can carry out embodiments of the present invention. A (measured) composite envelope NMR spectrum of NMR spectra of a fitting region of a biosample (e.g., blood plasma or serum) can be obtained (block 500). The NMR composite signal envelope is electronically deconvolved using a defined model having HDL, LDL and VLDL/Chylos components and a plurality of curve fit (e.g., Lorentzian) functions associated with at least a GlycA peak region centered at a defined chemical shift location (e.g., 2.00 ppm) associated with GlycA (block 502). A defined number of curve fitting functions for the peak region associated with GlycA can be summed (block 515). A conversion factor can be applied to the summed functions to generate a calculated measurement of GlycA (block 520).

The method can include providing at least one defined mathematical model of risk of progression to type 2 diabetes within 5-7 years that is used to calculate a diabetes risk score (block 523). The method can include identifying whether the patient is at risk of developing type 2 diabetes and/or has prediabetes based on the defined mathematical risk model that includes a plurality of lipoprotein components and GlycA or valine to generate the DRI score (block 524).

Optionally, the DRI and/or GlycA calculations can be provided in a patient and/or clinical trial report (block 522).

The defined GlycA deconvolution model can include a protein signal component at a density greater than about 1.21 g/L that can be deconvolved/separated from the signal composite envelope (block 503).

FIG. 20A is a schematic illustration of an exemplary patient test report 100 that can include various lipoprotein parameters such as two or more of DRI, GlycA, Valine, HDL-P, LDL-P 101. The DRI and/or GlycA number 101 can be presented with risk assessment summary 101s correlated to population norms, graphs, typical ranges, and/or degree of risk (e.g., high, increased or low risk), shown as a sliding scale graph in FIG. 20A.

However, other risk summary configurations may be used including ranges, high to low or low to high, or just noting whether the associated risk is low, medium or increased and/or high.

FIG. 20B is another example of a patient report with a visual (typically color-coded) graphic summary of a continuum of risk from low to high according to embodiments of the present invention.

FIG. 21 illustrates that a graph 130 of DRI values over time can be provided to illustrate a change in patient health and/or inflammatory status over time due to age, medical intervention or a therapy according to some embodiments. Tracking this parameter may provide a clinical indicator of efficacy of a therapy and/or a better risk predictor for type 2 diabetes for patients. As shown in FIG. 21, the graph analysis can be used to monitor a patient over time to correlate known start or use of a drug or other therapy. Future drugs or uses of known drugs can be identified, screened or tested in patients identified using DRI and/or GlycA evaluations of drugs or therapies of any suitable disease state including, for example, anti-diabetes and anti-obesity therapies.

The tracking can be provided via a tracking module that can be provided as an APPLICATION ("APP") for a smartphone or other electronic format for ease in tracking and/or for facilitating patient compliance with a therapy.

Figure 22A:
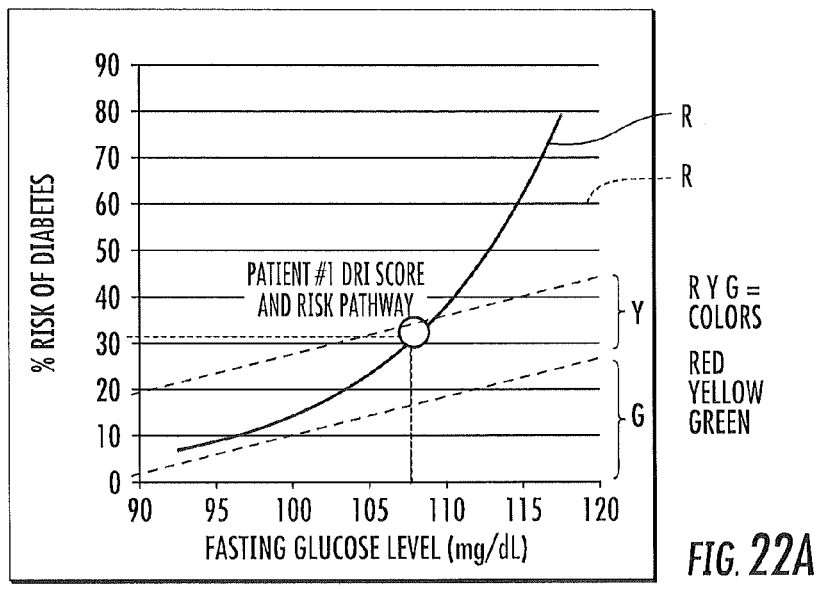
FIGS. 22A and 22B are graphical patient/clinical reports of % risk of diabetes versus FPG level and DRI score and risk pathway.
Figure 22B:
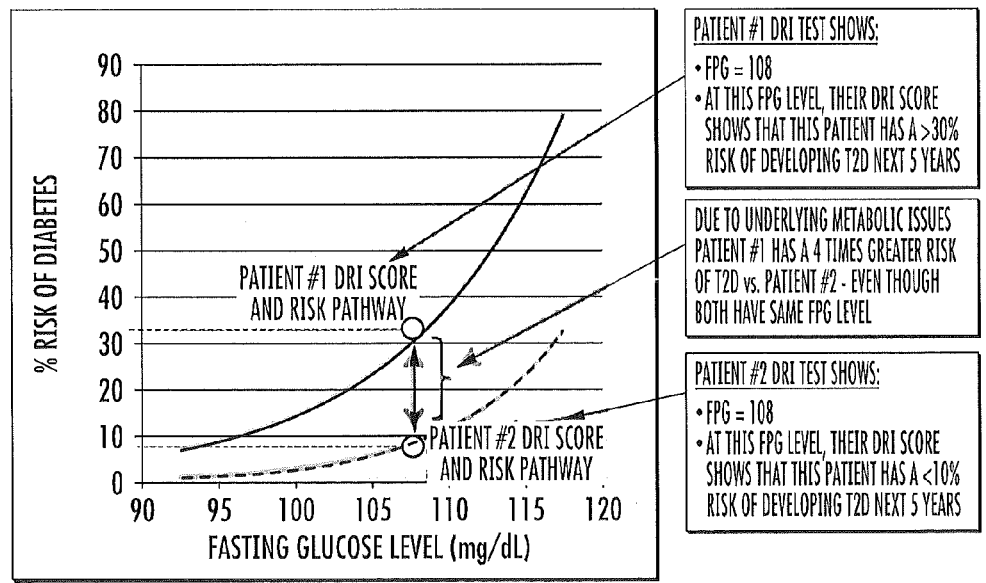

FIGS. 22A and 22B are graphical patient/clinical reports of % risk of diabetes versus FPG level and DRI score and risk pathway. FIG. 22A shows patient #1's score while FIG. 22B shows patient #1's score in comparison with a lesser risk patient (patient number 2) having the same FPG. While each patient has the same FPG, they have different metabolic issues identified by the DRI scores stratifying risk according to embodiments of the present invention.

Figure 23A:
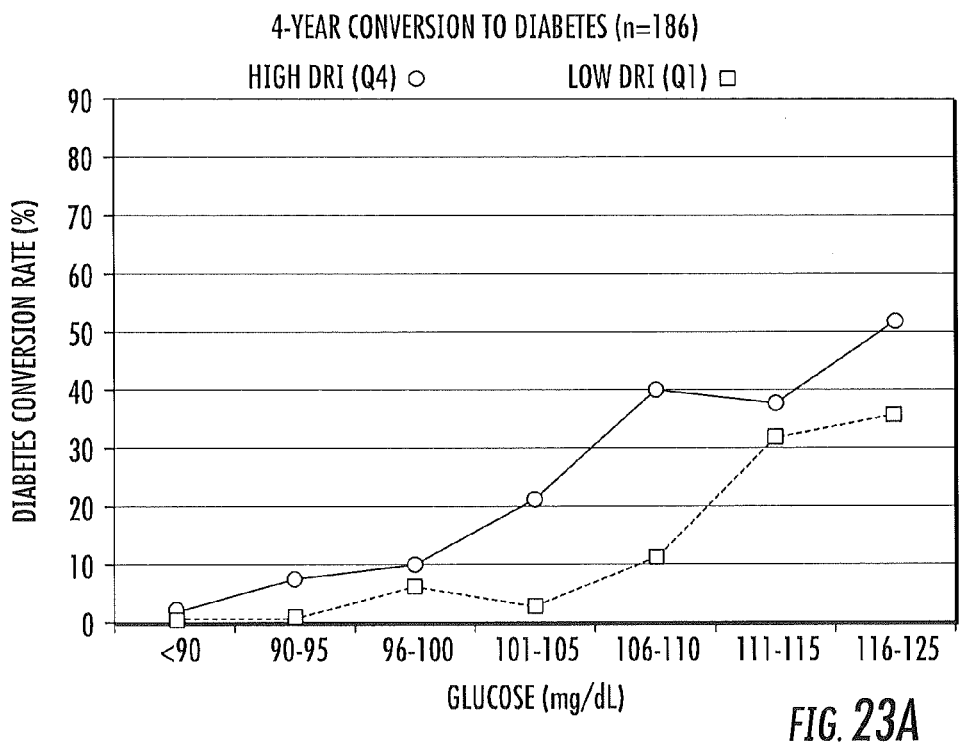
FIGS. 23A-23C are graphical patient/clinical reports of diabetes conversion rate (%) versus FPG level and DRI score (high DRI, Q4 and low DRI, Q1) according to embodiments of the present invention.
Figure 23B:
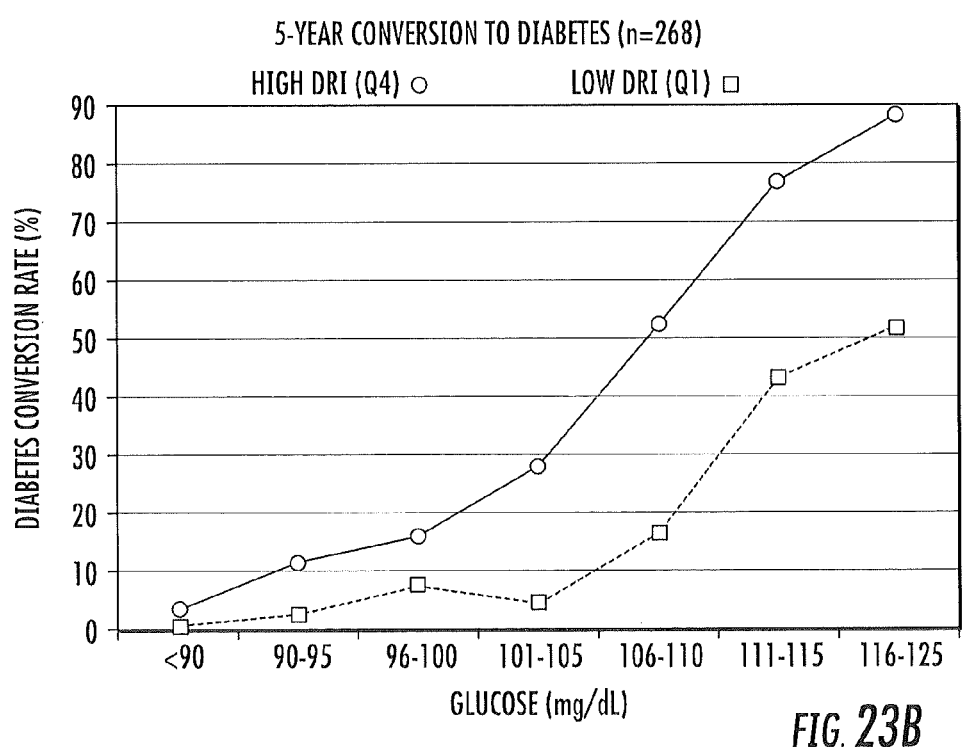
Figure 23C:
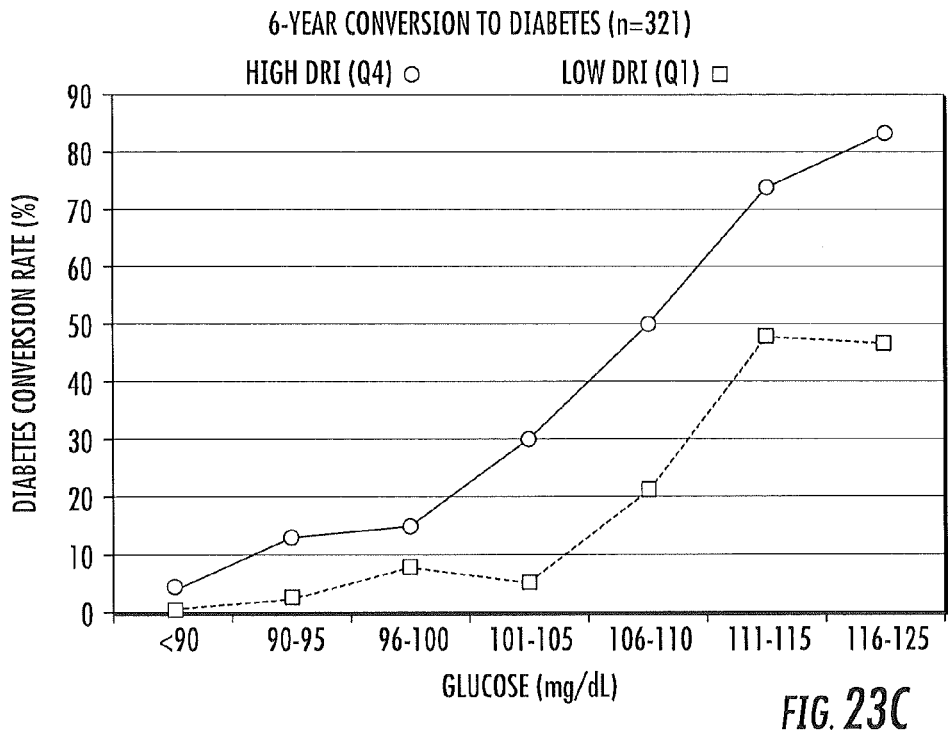

FIGS. 23A-23C are graphical patient/clinical reports of diabetes conversion rate (%) versus FPG level and DRI score (high DRI, Q4 and low DRI, Q1) according to embodiments of the present invention. FIG. 23A is for a 4-year risk of conversion to diabetes. FIG. 23B is a 5-year risk of conversion and FIG. 23C is a 6 year risk of conversion.

Figure 24:
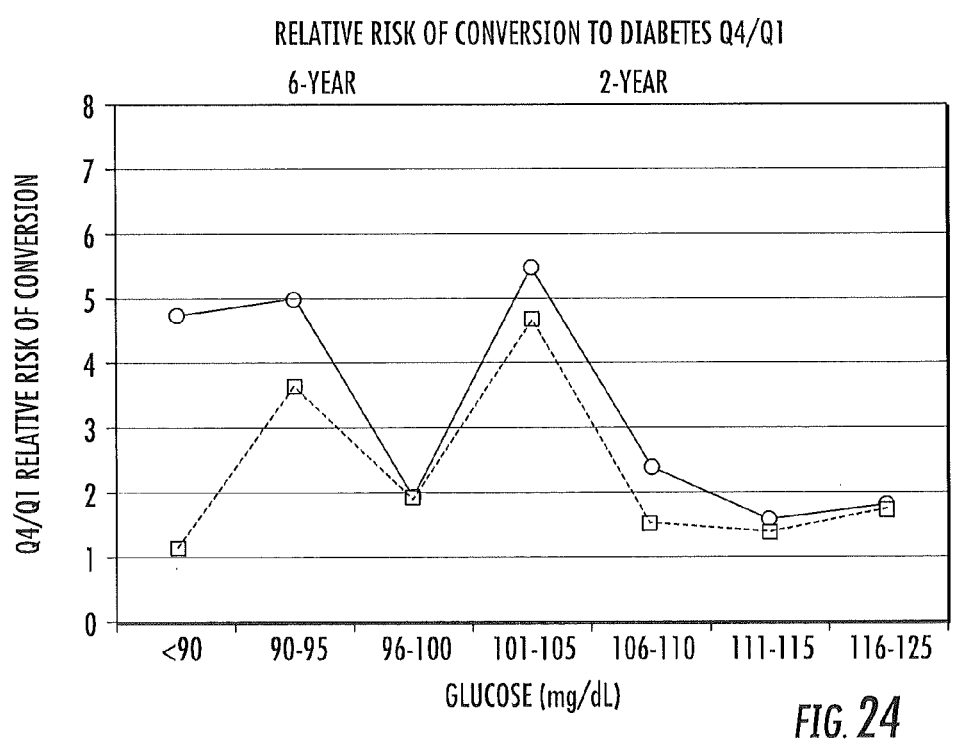
FIG. 24 is a graphical patient/clinical report of a Q4/Q1 relative risk of diabetes conversion (1-8) versus FPG level and DRI score for both 6-year (upper line) and 2-year conversions periods according to embodiments of the present invention.

FIG. 24 is a graphical patient/clinical report of a Q4/Q1 relative risk of diabetes conversion (1-8) versus FPG level and DRI score for both 6-year (upper line) and 2-year conversions periods according to embodiments of the present invention.

Figure 25:
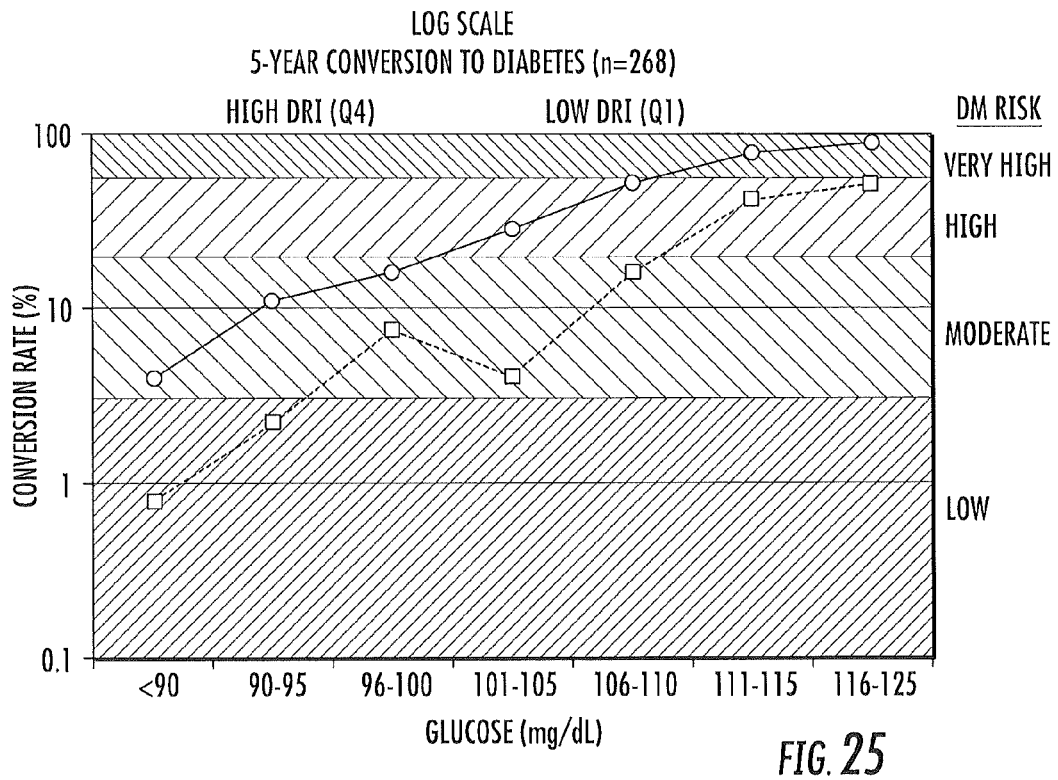
FIG. 25 is a graphical patient/clinical report of log scale 5 year conversion with a diabetes conversion rate (%) versus FPG level and DRI score (high DRI, Q4 and low DRI, Q1) color coded from green, yellow, pink/orange to red and with a legend textually correlating the risk as very high, high, moderate and low, according to embodiments of the present invention.

FIG. 25 is a graphical patient/clinical report of log scale 5 year conversion with a diabetes conversion rate (%) versus FPG level and DRI score (high DRI, Q4 and low DRI, Q1) color coded from green, yellow, pink/orange to red and with a legend textually correlating the risk as very high, high, moderate and low, according to embodiments of the present invention.

Figure 26:
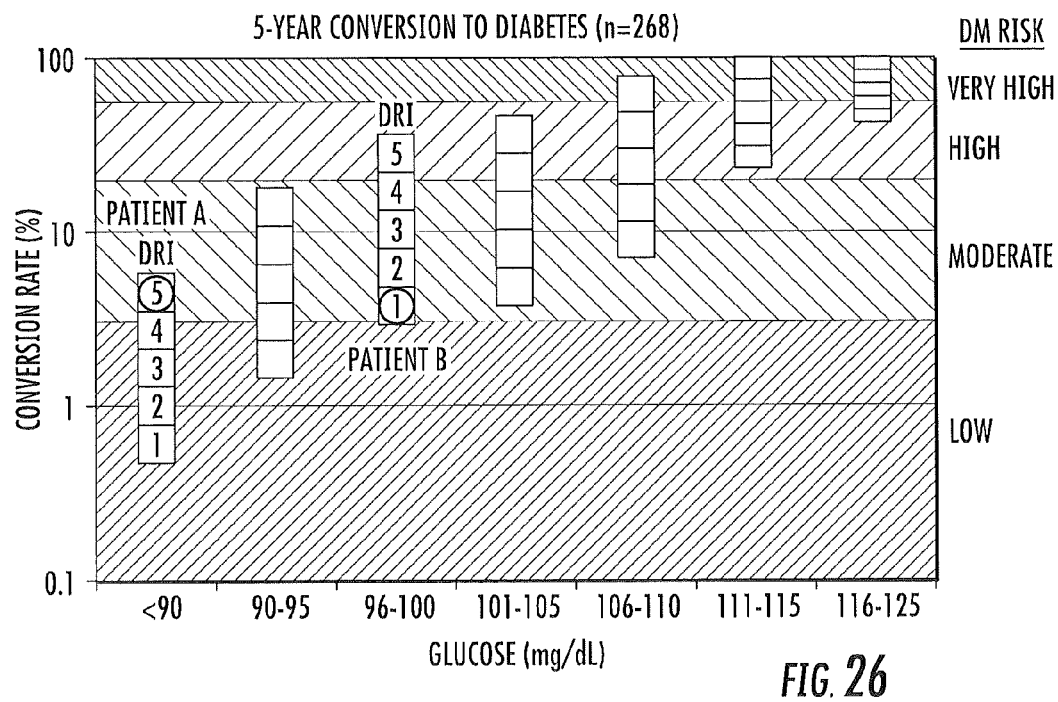
FIG. 26 is a graphical patient/clinical report of 5 year conversion to diabetes with a diabetes conversion rate (%) versus FPG level and DRI score (high DRI, Q4 and low DRI, Q1) color coded from green, yellow, pink/orange to red and with a legend textually correlating the risk as very high, high, moderate and low, according to embodiments of the present invention.

FIG. 26 is a graphical patient/clinical report of 5 year conversion to diabetes with a diabetes conversion rate (%) versus FPG level and DRI score (high DRI, Q4 and low DRI, Q1) color coded from green, yellow, pink/orange to red and with a legend textually correlating the risk as very high, high, moderate and low, according to embodiments of the present invention.

Embodiments of the invention will now be described by way of the following non-limiting Examples.

EXAMPLES

Example 1

A Diabetes Risk index (DRI) was developed using MESA that uses only information derived from a single nuclear magnetic resonance (NMR) spectrum of a fasting plasma sample. The DRI can identify the highest-risk patients who are likely to benefit the most from intervention. This information includes glucose and lipoprotein subclass/size parameters previously linked to insulin resistance, as well as valine, and GlycA. FIG. 1 was generated using NMR spectra collected at baseline from the Multi-Ethnic Study of Atherosclerosis (MESA). The MESA dataset consisted of 3185 participants, 280 of whom developed diabetes during 5 years of follow-up. FIG. 1 presents the diabetes conversion rates of subjects within 6 glucose subgroups (dotted line), and those for subjects in the upper and lower quartile of DRI within each glucose stratum. As shown, the risk of developing diabetes at any given glucose level is substantially greater for DRI in Q4 vs Q1. The NMR-based diabetes risk score can effectively stratify risk without the need for additional clinical information.

In this analysis, predictive modeling techniques were used to identify a "best" logistic regression model of five year diabetes conversion. The modeling used clinical data from the MESA study as well as NMR derived lipid and metabolite data. Although the final model selection restricted the data to subjects with baseline glucose less than or equal to 115, initial modeling considered the possibility of different "best" models for subjects with baseline glucose less than or equal to 100, subjects with baseline glucose greater than 100 but less than or equal to 115, and subjects with baseline glucose greater than 115 but less than or equal to 125.

One selected model for predicted five year conversion to diabetes included baseline glucose (glucos1c), VLDL size (vsz3), the ratio of medium HDL-P to total HDL-P (HMP_HDLP), medium HDL-P (hmp3), the sum of large VLDL-P and medium VLDL-P (vlmp3), GlycA, and valine. This model included two interactions: HMP_HDLP by GlycA and vsz3 by vlmp3. It was built using data from subjects with baseline glucose less than or equal to 115.

During development of these parameters, large VLDL-P (vlp3) was replaced by vlmp3 (sum of vmp3 and vlp3) in the NMR model as it was found to give better predictive results. Further exploration showed that the NMR model could include an interaction between VLDL size and vlmp3.

The final series of analyses showed that VLDL size and vlp3 (prior to calculation of vlmp3) could be appropriately truncated at low and high values without degrading the predictive accuracy. The benefit of such truncation may be model robustness. Also, the analysis showed that accounting for possible non-linear effects of VLDL size and vlmp3 on five year conversion was unnecessary.

Example 2

The DRI index model can employ lipoproteins, valine and GlycA as seven different parameters (including 5 lipoprotein parameters): VLDL size, large+medium VLDL particle number, total HDL and medium HDL subclass particle number, valine, and GlycA.

Another study of the MESA dataset consisted of 4985 non-diabetic participants, 411 of whom developed diabetes during 6 years of follow-up. The MESA data restricted to the 1832 individuals with intermediate glucose 90-110 mg/dL, 198 of whom converted to diabetes. Conversion rates by quintile of a baseline DRI index and the four component parts of the DRI model: lipoproteins, GlycA, valine, and glucose were assessed. Relative rates for those in the extreme quintiles were 2.2 for lipoproteins, 1.9 for GlycA, 1.7 for valine, 6.3 for glucose, and 10.7 for DRI (2.2% in Q1; 23.0% in Q5).

The results indicate that the DRI score, without any additional clinical information, can identify among patients with intermediate glucose levels those with diabetes risk differing >10-fold. Ratios between the first quintile and the fifth quintile establish that there is a 10.7 ratio for DRI which indicates that patients can have a 10 fold difference in diabetes risk when the FPG is in the range of 90-110 mg/dL.

It is believed that the new DRI scores can allow at-risk patients to be targeted for intervention before the onset of substantial beta-cell dysfunction.

Example 3

MESA and IRAS Comparison

FIG. 27 is a table of data that shows the performance of DRI (with glucose) in the IRAS dataset, the MESA dataset, and IRAS dataset (using the glucose subgroups from MESA). When IRAS samples were collected, the definitions of prediabetes and diabetes were different than that of MESA, which occurred years later.

FIG. 28 shows the performance of DRI (without glucose) in the same dataset criteria as FIG. 27. The highlighted values show the difference between the 5th quintile and the first quintile.

IRAS: Observational study of middle-aged Hispanic, non-Hispanic white, and African-American men and women. Blood samples obtained 1992-1994. NMR analyses of thawed-refrozen heparin plasma performed in 2001 on Varian instruments (preceding Profilers or current generation NMR analyzers used by LipoScience, Inc., Raleigh, N.C.) using WET water suppression. NMR dataset population was 46% normoglycemic (old definition, glucose <110 mg/dL), 22% impaired glucose tolerance, 32% diabetic. These analyses are for the n=982 nondiabetic subjects, 134 of whom developed diabetes during a mean 5.2 years of follow-up.

Spearman correlation in MESA and IRAS
Logistic regression results: Conversion to
New Diabetes in IRAS and MESA

| parameters | IRAS, 134 New Diab (N = 961) | | | MESA, 411 Newdiab (N = 4985) | | |
|---|---|---|---|---|---|---|
| | model $X^2$ | param $X^2$ | Param P | model $X^2$ | param $X^2$ | Param P |
| LPIR | 120.8 | 27.4 | <0.0001 | 776.8 | 27.5 | <0.0001 |
| DRInmr (no glucose) | 108.0 | 16.7 | <0.0001 | 796.2 | 47.9 | <0.0001 |
| DRI (LPIR) no glucose | 111.6 | 19.4 | <0.0001 | 796.1 | 46.8 | <0.0001 |
| Vsz | 96.8 | 7.9 | 0.005 | 750.1 | 18.8 | <0.0001 |
| Lsz | 101.4 | 9.9 | 0.0017 | 760.0 | 11.5 | 0.0007 |
| Hsz | 112.8 | 18.5 | <0.0001 | 760.2 | 11.1 | 0.0009 |
| Vlp | 106.3 | 16.4 | <0.0001 | 752.1 | 3.7 | 0.0559 |
| Lsp | 107.5 | 17.1 | <0.0001 | 757.1 | 8.7 | 0.0032 |
| hlp | 108.3 | 15.1 | 0.0001 | 756.0 | 7.0 | 0.0082 |
| GlycA | 93.2 | 2.3 | | 755.8 | 7.5 | 0.0063 |
| Valine | 93.7 | 2.7 | 0.099 | 767.5 | 19.1 | <0.0001 |
| lsp lsz hsz hlp vlp vsz | 120.6 | HSZ | | 767.0 | VLP VSZ | | adjusted on glucose age gender race

Example 4

The model parameters below were derived from regression models that included glucose/size/metabolite/ratio/SizePlus family. The initial form of these models included baseline glucose, VLDL size (vsz3), GlycA, medium HDL-P ratio (HMP_HDLP), medium HDL-P (hmp3), large VLDL-P (vlp3), and the interaction between GlycA and medium HDL-P ratio. Additional variable investigation determined that gender and valine could be added to this model, but the addition of alanine did not improve predictive accuracy. Further study and discussion determined that large VLDL-P (vlp3) should be replaced by the sum of large and medium VLDL-P (vlmp3). Also, exploratory analyses determined that an interaction between VLDL size (vsz3) and vlmp3 was statistically significant in the model. The modeling used subjects in the training dataset with baseline glucose less than or equal to 115 for model training, and subjects in the test dataset with baseline glucose less than or equal to 115 for model testing.

DRI models can be based on a likelihood and/or predicted five year conversion to diabetes. The risk evaluation models can include VLDL size (vsz3), a ratio of medium HDL-P to total HDL-P (HMP_HDLP), medium HDL-P (hmp3), a sum of large VLDL-P and medium VLDL-P (vlmp3), GlycA, and valine.

This model includes two interactions: HMP_HDLP by GlycA and vsz3 by vlmp3. The model can optionally also include a baseline glucose (glucos1c).

Additional modeling determined that VLDL size (vsz3) and large VLDL-P (vlp3, prior to calculation of vlmp3) could be truncated without degradation to predictive accuracy. For vsz3, any value less than 39.2 was truncated to 39.2, and any value greater than 65.1 was truncated to 65.1. For vlp3, any value less than 0.7 was truncated to 0.7, and any value greater than 7.9 was truncated to 7.9.

DRIp Non LPIR Model C-statistic 0.840

| Parameter | DF | Estimate | Standard Error | Wald Chi-Square | Pr > ChiSq |
|---|---|---|---|---|---|
| Intercept | 1 | −17.6413 | 1.6351 | 116.4032 | <.0001 |
| Glucose | 1 | 0.1236 | 0.00865 | 204.2648 | <.0001 |
| vsz | 1 | 0.0928 | 0.0204 | 20.7076 | <.0001 |
| GlycA | 1 | −0.0409 | 0.0361 | 1.2822 | 0.2575 |
| HMP_HDLP | 1 | −7.9057 | 2.7708 | 8.1410 | 0.0043 |
| GlycA * HMP_HDLP | 1 | 0.3066 | 0.0884 | 12.0228 | 0.0005 |
| Hmp | 1 | −0.0790 | 0.0325 | 5.9206 | 0.0150 |
| VLMP | 1 | 0.0608 | 0.0268 | 5.1522 | 0.0232 |
| vsz * VLMP | 1 | −0.00140 | 0.000535 | 6.8493 | 0.0089 |
| Valine | 1 | 0.00856 | 0.00310 | 7.6069 | 0.0058 |

DRI-LPIR Model C-statistic 0.839

| Parameter | DF | Estimate | Standard Error | Wald Chi-Square | Pr > ChiSq |
|---|---|---|---|---|---|
| Intercept | 1 | −14.8629 | 1.2903 | 132.6852 | <.0001 |
| Valine | 1 | 0.00756 | 0.00312 | 5.8947 | 0.0152 |
| Glucose | 1 | 0.1235 | 0.00867 | 203.0915 | <.0001 |
| LPIR | 1 | 0.0253 | 0.00626 | 16.2565 | <.0001 |
| hmp | 1 | −0.2651 | 0.0651 | 16.5696 | <.0001 |
| vmp | 1 | 0.0165 | 0.0110 | 2.2379 | 0.1347 |
| LPIR * vmp | 1 | −0.00051 | 0.000194 | 6.7620 | 0.0093 |
| GlycA | 1 | −0.0170 | 0.0304 | 0.3123 | 0.5762 |
| hmp * GlycA | 1 | 0.00738 | 0.00209 | 12.4268 | 0.0004 |

Example 5

The Diabetes Risk Index (DRI) test can be a lab-based multivariate assay that employs a defined mathematical model to yield a single composite score of one's risk of developing type II diabetes in 5 years. Predictive biomarkers included in the assay include: fasting glucose, lipoprotein sub-fractions, branched chain amino acid(s) and one or more inflammatory biomarker(s). Clinical performance is believed to be superior to fasting glucose alone in individuals with FPG<125, and is continually more predictive of diabetes risk vs. FPG with lowering levels of FPG. This is because the DRI risk score captures one's underlying metabolic defects by including these other predictive analytes, which glucose alone does not capture.

Data used to develop and validate DRI scores can be based on retrospective analysis of data from a multi-center and multi-ethnic prospective observational study with nearly 5,000 non-diabetic subjects at baseline. The patient report for this assay can show a fasting glucose value and a single 5-year diabetes risk prediction rate (which includes the risk predictive value of fasting glucose along with the other biomarkers).

Example 6

The Diabetes Risk Index (DRI) model can be calculated using a plurality of components including at least one lipoprotein component, valine and/or another branched chain amino acid, and GlycA and/or another inflammatory marker. The model can be adjusted to use different components based on whether the patient is on a statin or other drug therapy known to impact DRI risk scores and/or based on whether the biosample is a fasting or non-fasting biosample.

The DRI risk score can be calculated in a plurality of different manners and filtered before sent to a clinician (or sent to the clinician for correct reporting) and patient based on defined patient criteria so that the patient is provided the appropriate score for the test and patient-specific parameters for that biosample.

Example 7

The DRI model is configured to stratify risk in subjects having the same A1C, oral glucose tolerance or FPG measurement and a different diabetes risk score. The diabetes risk index score can be a numerical score within a defined score range, with scores associated with a fourth quartile (4Q) or fifth quintile (5Q) of a population norm reflecting an increased or high risk of developing type 2 diabetes within 5-7 years. Respective subjects that are at increased risk of developing type 2 diabetes prior to onset of type-2 diabetes when glucose is in a range that is below prediabetes to the high end of prediabetes, e.g., a fasting blood glucose (FPG) levels are between 90-125 mg/dL can be identified. The DRI score provides information to stratify risk in subjects having the same glucose measurement and a different diabetes risk score based on underlying metabolic issues in different patients.

Example 8

Table 6 lists potential alternative VLDL parameters that may be used in a DRI model based on a logistic regression analysis on VLDL. One or more of the alternative VLDL parameters may optionally be used with one or more of the components described above with respect to any of the other DRI models and/or components thereof described in the Examples and/or Detailed Description part of the specification. Large VLDL may be referred to as "VLP (V5p+V6p+CHYp)", which are TRL particles ranging from 60-260 nm diameter. Different definitions of "large VLDL" could be used in a DRI model. For example, the chylomicrons could be excluded and may be called TRL60-140 based on Table 5. Alternatively or in addition, TRL60-120 (without V6-140) may be used in a DRI model.

TABLE 6

Potential alternative VLDL parameters that may be used in a DRI model with other components.

| | Logistic regression on New Diabetes | | | |
| --- | --- | --- | --- | --- |
| | MESA N = 210/2038, model unadjusted, glucose 90-110 mg/dL | | MESA N = 210/2038, model adjusted on glucose (glucose 90-110 mg/dL) | |
| NMR parameters | X2 parameter (model adjusted on glucose) | X2 parameter (model not-adjusted) | X2 parameter (model adjusted on glucose) | X2 parameter (model not-adjusted) |
| ChyloL (185-260) | −0.80 | | −0.77 | |
| ChyloS (170-180) | −5.69 | 0.017 | −3.90 | 0.0482 |
| V6tg(2) 100 + 120 | 5.60 | 0.0178 | 4.47 | 0.0344 |
| V6tg(3) 100 + 120 + 140 | 3.73 | 0.0534 | 3.13 | 0.0766 |
| V5tg | 8.31 | 0.0039 | 4.96 | 0.0259 |
| VLP (V5p + V6p + CHYp) | 8.55 | 0.0035 | 5.13 | 0.0235 |
| V56tg(2) | 9.68 | 0.0019 | 6.00 | 0.0143 |
| V56tg(3) | 9.46 | 0.0021 | 5.88 | 0.0153 |

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention as defined in the claims. In the claims, means-plus-function clauses, where used, are intended to cover the structures described herein as performing the recited function and not only structural equivalents but also equivalent structures. Therefore, it is to be understood that the foregoing is illustrative of the present invention and is not to be construed as limited to the specific embodiments disclosed, and that modifications to the disclosed embodiments, as well as other embodiments, are intended to be included within the scope of the appended claims. The invention is defined by the following claims, with equivalents of the claims to be included therein.

That which is claimed is:

1. A method of evaluating a subject's risk of developing type 2 diabetes and/or of having prediabetes, comprising:
performing Nuclear Magnetic Resonance to determine the levels of at least one lipoprotein component, at least one branched chain amino acid and GlycA from an in vitro blood plasma or serum biosample from the subject, wherein GlycA is a composite Nuclear Magnetic Resonance signal from carbohydrate portions of acute phase reactant glycoproteins containing N-acetylglucosamine and/or N-acetylgalactosamine moieties that is detectable at about 2.00 ppm when Nuclear Magnetic Resonance measurements are performed at about 47 degrees C.; and
programmatically calculating a diabetes risk index score for the subject using a defined mathematical model of risk of developing type 2 diabetes that includes the Nuclear Magnetic Resonance measurements of GlycA, the at least one lipoprotein component and the at least one branched chain amino acid.

2. The method of claim 1, further comprising programmatically defining at least two different mathematical models of risk of developing type 2 diabetes, the at least two different mathematical models including one for subjects on a statin therapy that includes lipoprotein component that are statin insensitive and one for subjects not on a statin therapy.

3. The method of claim 1, further comprising programmatically defining at least two different mathematical models of risk of developing type 2 diabetes, the at least two different mathematical models with different lipoprotein components including one for fasting biosamples, and one for non-fasting biosamples.

4. The method of claim 1, further comprising programmatically generating a report with a graph of risk of progression to type 2 diabetes in the future over a 1-7 year period versus ranges of fasting glucose levels and a quartile of risk associated with the diabetes risk index score.

5. The method of claim 1, further comprising electronically generating reports that present the diabetes risk index score for respective subjects.

6. The method of claim 1, wherein the at least one defined mathematical model of risk includes NMR derived measurements of a plurality of selected lipoprotein components of the at least one biosample of the subject and an NMR measurement of valine as the at least one branched chain amino acid.

7. The method of claim 6, wherein the at least one defined mathematical model includes selected lipoprotein components comprising at least two of the following: large Very Low Density Lipoprotein subclass particle number, medium Very Low Density Lipoprotein subclass particle number, total High Density Lipoprotein subclass particle number, medium High Density Lipoprotein subclass particle number and Very Low Density Lipoprotein particle size.

8. The method of claim 1, further comprising programmatically evaluating a fasting blood glucose measurement of the subject using at least one in vitro biosample, wherein the diabetes risk index score is a numerical score within a defined score range, with scores associated with a fourth quartile or fifth quintile of a population norm reflecting an increased or high risk of developing type 2 diabetes within 5-7 years, and programmatically identifying respective subjects that are at increased risk of developing type 2 diabetes prior to onset of type-2 diabetes when (i) fasting blood glucose levels are between 90-110 mg/dL and (ii) the diabetes risk score is in the fourth quartile or fifth quintile range.

9. The method of claim 1, further comprising programmatically evaluating a fasting blood glucose measurement of the subject, wherein the diabetes risk index score is a numerical score within a defined score range, with scores associated with a fourth quartile or fifth quintile of a population norm reflecting an increased or high risk of developing type 2 diabetes within 5-7 years, the method further comprising programmatically identifying respective subjects that are at increased risk of developing type 2 diabetes prior to onset of type-2 diabetes when fasting blood glucose levels are between 90-125 mg/dL, wherein the programmatically identifying is carried out to stratify risk in subjects having the same fasting blood glucose and a different diabetes risk score.

10. The method of claim 1, wherein the defined mathematical risk model includes only Nuclear Magnetic Resonance derived measurements of a subject's in vitro blood plasma or serum biosample.

11. The method of claim 1, further comprising, before the programmatic calculation, placing a blood plasma or serum sample of the subject in an Nuclear Magnetic Resonance spectrometer;
  obtaining at least one Nuclear Magnetic Resonance spectrum of the sample;
  deconvolving the obtained at least one Nuclear Magnetic Resonance spectrum; and
  calculating the Nuclear Magnetic Resonance levels of GlycA and the at least one lipoprotein component based on the deconvolved spectrum.

12. The method of claim 11, further comprising calculating the level of valine as the at least one branched chain amino acid.

13. The method of claim 1, wherein the diabetes risk index score has a defined numerical range, and wherein the method further comprises programmatically generating a report that identifies a respective subject as at risk of developing prediabetes if a fasting blood plasma or serum glucose value is between about 90-99 mg/dl and the diabetes risk index is in a fourth quartile or fifth quintile of a population norm.

14. The method of claim 1, wherein the at least one branched chain amino acid is valine.

15. The method of claim 14, further comprising, before the programmatic calculation;
  electronically obtaining a Nuclear Magnetic Resonance spectrum of a valine fitting region of the biosample of the subject;
  electronically identifying a valine signal as located upstream or downstream a defined number of data points of a peak of a defined diluent in the biosample;
  electronically deconvolving the composite Nuclear Magnetic Resonance spectrum using a defined deconvolution model; and
  electronically quantifying valine using the deconvolved Nuclear Magnetic Resonance spectrum for the Nuclear Magnetic Resonance measurement of valine.

16. The method of claim 1, wherein the at least one defined mathematical model includes a ratio of medium High Density Lipoprotein Particle number to total High Density Lipoprotein Particle number.

17. The method of claim 1, wherein the at least one defined mathematical model includes Very Low Density Lipoprotein subclass particle size, a ratio of medium High Density Lipoprotein Particle number to total High Density Lipoprotein Particle number multiplied by GlycA and a ratio of Very Low Density Lipoprotein size by a sum of large Very Low Density Lipoprotein Particle number and medium Very Low Density Lipoprotein Particle number.

18. The method of claim 1, wherein the at least one defined mathematical model includes a plurality of different defined models, including one that includes lipoprotein components that are insensitive to statin therapy, one that includes lipoprotein components that are sensitive to statin therapy, one that is for fasting biosamples and one that is for non-fasting biosamples.

19. The method of claim 1, wherein the generated report comprises:
  the diabetes risk index score calculated based on a defined mathematical model of risk of progression to type 2 diabetes within the next 5-7 years, with values above a population norm associated with increased risk; and
  a graph showing a percentage in a range of risk of diabetes conversion over a 1, 2, 3, 4, 5, 6, or 7 year risk window versus glucose level and an associated quartile or quintile of the patient's DRI risk score relative to a defined population.

20. The method of claim 19, wherein the generated report further comprises a comparative risk of a population with a lower or higher quartile or quintile DRI score and the same glucose measurement.

21. A method of evaluating a subject's risk of developing type 2 diabetes and/or of having prediabetes, comprising:
  performing Nuclear Magnetic Resonance measurements to electronically obtain a composite Nuclear Magnetic Resonance spectrum of at least one lipoprotein component, at least one branched chain amino acid and a GlycA fitting region of at least one biosample of the subject, wherein the GlycA fitting region extends from 1.845 ppm to 2.080 ppm, wherein GlycA is a composite Nuclear Magnetic Resonance signal from carbohydrate portions of acute phase reactant glycoproteins containing N-acetylglucosamine and/or N-acetylgalactosamine moieties that is detectable at about 2.00 ppm when the Nuclear Magnetic Resonance measurements are performed at about 47 degrees C.;
  electronically deconvolving the composite Nuclear Magnetic Resonance spectrum using a deconvolution model with high density lipoprotein components, low density lipoprotein components, very low density lipoprotein components, and curve fit functions associated with at least a GlycA peak region;
  programmatically generating a measure of GlycA using the curve fit functions; and
  programmatically calculating a diabetes risk index score of a subject using at least one defined mathematical model of risk of developing type 2 diabetes that includes the at least one lipoprotein component, the at least one branched chain amino acid and the measure of GlycA obtained from at least one biosample of the subject, wherein the method is carried out using a circuit with at least one processor in communication with at least one Nuclear Magnetic Resonance spectrometer.

22. The method of claim 21, wherein the at least one branched chain amino acid is valine.

23. The method of claim 21, wherein the curve fit functions are overlapping curve fit functions, and wherein the measure of GlycA is generated by summing a defined number of curve fit functions, and wherein the deconvolution model further comprises a protein signal component for protein having a density greater than 1.21 g/L.

24. A circuit configured to determine whether a patient is at-risk for developing type 2 diabetes within the next 5-7 years and/or whether a patient has prediabetes, comprising:
  at least one processor configured to electronically calculate a diabetes risk index based on at least one mathematical model of risk to convergence to type 2 diabetes within 5-7 years that considers at least one lipoprotein component, at least one branched chain amino acid and GlycA from at least one in vitro biosample of the subject, wherein GlycA is a composite Nuclear Magnetic Resonance signal from carbohydrate portions of acute phase reactant glycoproteins containing N-acetylglucosamine and/or N-acetylgalactosamine moieties that is detectable at about 2.00 ppm when Nuclear Magnetic Resonance measurements are performed at about 47 degrees C.

25. The circuit of claim 24, wherein the at least one processor is configured to define at least two different mathematical models of risk of developing type 2 diabetes, the at least two different mathematical models including a first model for subjects on a statin therapy that includes lipoprotein components that are statin insensitive and a second model for subjects not on a statin therapy, wherein the second model includes at least some lipoprotein components that are different from the first model, and wherein the circuit is configured to identify subject characteristics to select the appropriate first or second model of risk for the calculation of the diabetes risk index score.

26. The circuit of claim 24, wherein the at least one processor is configured to define at least two different mathematical models of risk of developing type 2 diabetes with different lipoprotein components, the at least two different mathematical models including one for fasting biosamples, and one for non-fasting biosamples, and wherein the circuit identifies subject characteristics to select the appropriate mathematical model of risk for calculation of the diabetes risk index score.

27. The circuit of claim 24, wherein the at least one processor is configured to generate a report with a graph of risk of progression to type 2 diabetes in the future over a 1-7 year period versus ranges of fasting glucose levels and a quartile of risk associated with the diabetes risk index score.

28. The circuit of claim 27, wherein the graph includes visual references of at least first (low) and fourth (high) quartile DRI scores based on a defined population to thereby allow for ease of identifying or understanding risk stratification.

29. The circuit of claim 24, wherein the at least one processor is configured to evaluate a fasting blood glucose measurement of the subject, wherein the diabetes risk index score is a numerical score within a defined score range, with scores associated with a fourth quartile or fifth quintile of a population norm reflecting an increased or high risk of developing type 2 diabetes within 5-7 years, and wherein the at least one processor is configured to identify respective subjects that are at increased risk of developing type 2 diabetes prior to onset of type-2 diabetes when fasting blood glucose levels are between 90-110 mg/dL and the diabetes risk score is in the fourth quartile or fifth quintile range.

30. The circuit of claim 24, wherein the at least one processor is configured to evaluate a fasting blood glucose measurement of the subject, wherein the diabetes risk index score is a numerical score within a defined score range, with scores associated with a fourth quartile or fifth quintile of a population norm reflecting an increased or high risk of developing type 2 diabetes within 5-7 years, the at least one processor configured to identify respective subjects that are at increased risk of developing type 2 diabetes prior to onset of type-2 diabetes when fasting blood glucose levels are between 90-125 mg/dL, and wherein the at least one processor is configured to generate a report that can stratify risk in subjects having the same fasting blood glucose and a different diabetes risk score.

31. The circuit of claim 24, wherein the at least one mathematical model includes a plurality of lipoprotein components comprising at least two of the following: large very low density lipoprotein subclass particle number, medium very low density lipoprotein subclass particle number, total high density lipoprotein subclass particle number, medium high density lipoprotein subclass particle number and very low density lipoprotein particle size.

32. The circuit of claim 24, wherein the at least one branched chain amino acid is valine.

33. A computer program product for evaluating in vitro patient biosamples, the computer program product comprising:
a non-transitory computer readable storage medium having computer readable program code stored on the medium, the computer-readable program code comprising:

computer readable program code that provides at least one mathematical model of risk to progression to type 2 diabetes over a defined time period of between 1-7 years, wherein the at least one mathematical model of risk to progression to type 2 diabetes includes a plurality of components, including NMR derived measurements of GlycA and valine, wherein GlycA is a composite Nuclear Magnetic Resonance signal from carbohydrate portions of acute phase reactant glycoproteins containing N-acetylglucosamine and/or N-acetylgalactosamine moieties that is detectable at about 2.00 ppm when Nuclear Magnetic Resonance measurements are performed at about 47 degrees C.; and computer readable program code that calculates a diabetes risk index associated with a patient's biosample based on the at least one mathematical model of a risk of developing type 2 diabetes.

34. The computer program product of claim 33, further comprising computer readable program code configured to evaluate a glucose measurement of the patient, wherein the computer readable program code that calculates a diabetes risk index as a numerical score within a defined score range, with scores associated with a fourth quartile or fifth quintile of a population norm reflecting an increased or high risk of developing type 2 diabetes within 5-7 years.

35. The computer program product of claim 34, wherein the computer program product further comprises computer readable program code configured to identify respective patients that are at increased risk of developing type 2 diabetes prior to onset of type-2 diabetes when fasting blood glucose levels are between 90-110 mg/dL and the diabetes risk score is in the fourth quartile or fifth quintile range.

36. The computer program product of claim 34, wherein the computer program product is configured to generate a report that identifies respective subjects that are at increased risk of developing type 2 diabetes prior to onset of type-2 diabetes when fasting blood glucose levels are between 90-125 mg/dL, wherein the mathematical model stratifies risk in subjects having the same fasting blood glucose and a different diabetes risk score.

37. The computer program product of claim 34, wherein the at least one mathematical model includes a plurality of lipoprotein components comprising at least two of the following: large very low density lipoprotein subclass particle number, medium very low density lipoprotein subclass particle number, total high density lipoprotein subclass particle number, medium high density lipoprotein subclass particle number and very low density lipoprotein particle size.

38. The computer program product of claim 37, wherein the at least one branched chain amino acid is valine.

39. The computer program product of claim 33, further comprising:
computer readable program code that identifies and deconvolves a valine fitting region of a composite Nuclear Magnetic Resonance spectrum blood serum or plasma sample of a subject and generates a calculated measurement of valine for the Nuclear Magnetic Resonance derived measurement of valine; and
computer readable program code that deconvolves a GlycA fitting region of the composite Nuclear Magnetic Resonance spectrum, wherein the computer readable program code deconvolves the composite Nuclear Magnetic Resonance spectrum using a defined GlycA deconvolution model with (i) high density lipoprotein components, (ii) low density lipoprotein components, (iii) very low density lipoprotein components, (iv) another defined protein signal component and (v) curve fitting functions applied to at least a GlycA peak region and generates a calculated measurement of GlycA for the Nuclear Magnetic Resonance derived measurement of GlycA.

40. A system, comprising:
an NMR spectrometer for acquiring at least one NMR spectrum of an in vitro biosample; and
at least one processor in communication with the NMR spectrometer, the at least one processor configured to determine for a respective biosample using the at least one NMR spectrum a diabetes risk index score based on at least one defined mathematical model of risk to convergence to type 2 diabetes within 5-7 years that considers at least one lipoprotein component, at least one branched chain amino acid and GlycA obtained from at least one in vitro biosample of the subject, wherein GlycA is a composite Nuclear Magnetic Resonance signal from carbohydrate portions of acute phase reactant glycoproteins containing N-acetylglucosamine and/or N-acetylgalactosamine moieties that is detectable at about 2.00 ppm when Nuclear Magnetic Resonance measurements are performed at about 47 degrees C.

41. The system of claim 40, wherein the at least one processor is configured to define at least two different mathematical models of risk of developing type 2 diabetes, the at least two different mathematical models including one for subjects on a statin therapy that includes lipoprotein components that are statin insensitive and one for subjects not on a statin therapy with at least one different lipoprotein component.

42. The system of claim 40, wherein the at least one processor is configured to define at least two different mathematical models of risk of developing type 2 diabetes with different lipoprotein components, the at least two different mathematical models including one for fasting biosamples and one for non-fasting biosamples.

43. The system of claim 40, wherein the at least one processor is configured to generate a report with a graph of risk of progression to type 2 diabetes in the future over a 1-7 year period versus ranges of fasting glucose levels and a quartile of risk associated with the diabetes risk index score.

44. The system of claim 43, wherein the graph includes visual references of at least first (low) and fourth (high) quartile DRI scores based on a defined population to thereby allow for ease of identifying or understanding risk stratification.

45. The system of claim 40, wherein the at least one defined mathematical model includes selected lipoprotein components comprising at least two of the following: large very low density lipoprotein subclass particle number, medium very low density lipoprotein subclass particle number, total high density lipoprotein subclass particle number, medium high density lipoprotein subclass particle number and very low density lipoprotein particle size.

46. The system of claim 43, wherein the at least one branched chain amino acid is valine.

47. A Nuclear Magnetic Resonance system comprising:
a Nuclear Magnetic Resonance spectrometer;
a flow probe in communication with the spectrometer; and
at least one processor in communication with the spectrometer configured to:
(a) obtain
(i) a Nuclear Magnetic Resonance signal of a defined GlycA fitting region of NMR spectra associated with GlycA of a blood plasma or serum specimen in the flow probe, wherein GlycA is a composite Nuclear Magnetic Resonance signal from carbohydrate portions of acute phase reactant glycoproteins containing N-acetylglucosamine and/or N-acetylgalactosamine moieties that is detectable at about 2.00 ppm when Nuclear Magnetic Resonance measurements are performed at about 47 degrees C.;
(ii) Nuclear Magnetic Resonance signal of a defined valine fitting region of Nuclear Magnetic Resonance spectra associated with the specimen in the flow probe; and
(iii) Nuclear Magnetic Resonance signal of at least one lipoprotein component of the blood plasma or serum sample in the flow probe;
(b) calculate measurements of GlycA, valine and the at least one lipoprotein component; and
(c) calculate a diabetes risk index using a defined mathematical model of risk of developing type 2 diabetes and/or having prediabetes that uses the calculated measurements of GlycA, valine and the at least one lipoprotein component.

48. The system of claim 47, wherein the at least one processor comprises at least one local or remote processor and/or at least one processor onboard the Nuclear Magnetic Resonance analyzer, wherein the at least one processor is configured to deconvolve at least one composite Nuclear Magnetic Resonance spectrum of the specimen to generate the calculated measurements of GlycA, valine and the lipoprotein parameters.

49. A method of monitoring a patient to evaluate a therapy or determine whether the patient is at-risk of developing type 2 diabetes or has prediabetes, comprising:
performing Nuclear Magnetic Resonance measurements to measure selected lipoprotein subclasses, valine and GlycA, wherein GlycA is a composite Nuclear Magnetic Resonance signal from carbohydrate portions of acute phase reactant glycoproteins containing N-acetylglucosamine and/or N-acetylgalactosamine moieties that is detectable at about 2.00 ppm when the Nuclear Magnetic Resonance measurements are performed at about 47 degrees C.;
programmatically providing at least one defined mathematical model of risk of progression to type 2 diabetes that includes a plurality of components including Nuclear Magnetic Resonance derived measurements of selected lipoprotein subclasses, valine and GlycA;
programmatically deconvolving at least one Nuclear Magnetic Resonance spectrum of respective in vitro patient blood plasma or serum samples and determining measurements of lipoprotein subclasses, GlycA and valine;
programmatically calculating a diabetes risk index score of the respective patients using the at least one defined model and corresponding patient sample measurements;
electronically generating a patient report providing the diabetes index risk score; and
evaluating at least one of (i) whether the diabetes risk index is above a defined level of a population norm associated with increased risk of developing type 2 diabetes, and/or (ii) whether the diabetes risk index is increasing or decreasing over time in response to a therapy.

50. A circuit configured to determine whether a patient is at-risk for developing type 2 diabetes within the next 5-7 years and/or whether a patient has prediabetes, comprising:
at least one processor configured to electronically calculate a diabetes risk index based on at least one mathematical model of risk to convergence to type 2 diabetes within 5-7 years using Nuclear Magnetic Resonance derived measurements of GlycA, valine and a plurality of lipoprotein components, wherein GlycA is a composite Nuclear Magnetic Resonance signal from carbohydrate portions of acute phase reactant glycoproteins containing N-acetylglucosamine and/or N-acetylgalactosamine moieties that is detectable at about 2.00 ppm when Nuclear Magnetic Resonance measurements are performed at about 47 degrees C.

51. A system, comprising:
a Nuclear Magnetic Resonance spectrometer for acquiring at least one Nuclear Magnetic Resonance spectrum of an in vitro biosample; and
at least one processor in communication with the Nuclear Magnetic Resonance spectrometer, the at least one processor configured to determine for a respective biosample, using the at least one Nuclear Magnetic Resonance spectrum, a diabetes risk index score based on at least one defined mathematical model of risk to convergence to type 2 diabetes within 5-7 years that considers at least one lipoprotein component, at least one branched chain amino acid and GlycA as at least one inflammatory biomarker obtained from at least one in vitro biosample of the subject, wherein GlycA is a composite Nuclear Magnetic Resonance signal from carbohydrate portions of acute phase reactant glycoproteins containing N-acetylglucosamine and/or N-acetylgalactosamine moieties that is detectable at about 2.00 ppm when Nuclear Magnetic Resonance measurements are performed at about 47 degrees C.; and
wherein the at least one processor is configured to deconvolve the at least one Nuclear Magnetic Resonance spectrum and generate:
 (i) a Nuclear Magnetic Resonance measurement of GlycA:
 (ii) a Nuclear Magnetic Resonance measurement of valine;
 (iii) Nuclear Magnetic Resonance measurements of lipoprotein parameters; and
 (iv) the diabetes risk index
using the Nuclear Magnetic Resonance measurements of GlycA, valine and the lipoprotein parameters as components of the at least one defined mathematical model.

52. A system, comprising:
a Nuclear Magnetic Resonance spectrometer for acquiring at least one Nuclear Magnetic Resonance spectrum of an in vitro biosample; and
at least one processor in communication with the Nuclear Magnetic Resonance spectrometer, the at least one processor configured to determine for a respective biosample using the at least one Nuclear Magnetic Resonance spectrum a diabetes risk index score based on at least one defined mathematical model of risk to convergence to type 2 diabetes within 5-7 years that considers at least one lipoprotein component, at least one branched chain amino acid and GlycA as an inflammatory biomarker obtained from at least one in vitro biosample of the subject,
wherein GlycA is a composite Nuclear Magnetic Resonance signal from carbohydrate portions of acute phase reactant glycoproteins containing N-acetylglucosamine and/or N-acetylgalactosamine moieties that is detectable at about 2.00 ppm when Nuclear Magnetic Resonance measurements are performed at about 47 degrees C.; and
wherein the defined at least one mathematical model includes Nuclear Magnetic Resonance measurements of GlycA and a plurality of selected lipoprotein components using lipoprotein subclasses, sizes and concentrations measured from an in vitro blood plasma or serum biosample.

* * * * *